US008049777B2

(12) United States Patent
Akimoto et al.

(10) Patent No.: US 8,049,777 B2
(45) Date of Patent: Nov. 1, 2011

(54) INSERTION SUPPORT SYSTEM FOR SPECIFYING A LOCATION OF INTEREST AS AN ARBITRARY REGION AND ALSO APPROPRIATELY SETTING A NAVIGATION LEADING TO THE SPECIFIED REGION

(75) Inventors: Shunya Akimoto, Kawasaki (JP); Junichi Ohnishi, Hachioji (JP); Fumihiro Asano, Gifu (JP); Hiroshi Moriya, Fukushima (JP); Koichi Yamazaki, Sapporo (JP); Takashi Ishida, Fukushima (JP)

(73) Assignee: Olympus Corporation, Tokyo (JP)

( * ) Notice: Subject to any disclaimer, the term of this patent is extended or adjusted under 35 U.S.C. 154(b) by 1588 days.

(21) Appl. No.: 11/412,397

(22) Filed: Apr. 27, 2006

(65) Prior Publication Data
US 2006/0195033 A1 Aug. 31, 2006

Related U.S. Application Data

(63) Continuation of application No. PCT/JP2004/016034, filed on Oct. 28, 2004.

(30) Foreign Application Priority Data

Oct. 31, 2003 (JP) ................................. 2003-373808
Apr. 23, 2004 (JP) ................................. 2004-128489
Apr. 23, 2004 (JP) ................................. 2004-128490

(51) Int. Cl.
*A62B 1/04* (2006.01)
(52) U.S. Cl. .......................................................... 348/65

(58) Field of Classification Search ...................... 348/65
See application file for complete search history.

(56) References Cited

U.S. PATENT DOCUMENTS

| 5,954,650 | A | 9/1999 | Saito et al. |
| 6,064,904 | A | 5/2000 | Yanof et al. |
| 6,346,940 | B1 | 2/2002 | Fukunaga |
| 2003/0174872 | A1 | 9/2003 | Chalana et al. |
| 2005/0107679 | A1* | 5/2005 | Geiger et al. ................. 600/407 |

FOREIGN PATENT DOCUMENTS

| JP | 08016813 | 1/1996 |
| JP | 10-137190 | 5/1998 |

(Continued)

OTHER PUBLICATIONS

Partial European Search Report dated Apr. 22, 2010.

*Primary Examiner* — Jayanti K Patel
*Assistant Examiner* — Richard Torrente
(74) *Attorney, Agent, or Firm* — Scully, Scott, Murphy & Presser, P.C.

(57) ABSTRACT

According to an insertion support system of the present invention, when a biopsy area is specified at a periphery of the bronchi, the barycenter of the biopsy area is extracted. A circle centering on the barycenter is determined as a search area. The search area is expanded until the bronchi are located within the search area. A point in the search area to which the bronchi first reach is determined as an end point. A first route choice connecting the end point and a start point is determined. If the first route choice has not been registered yet, the first route choice is registered as a first registered route. Accordingly, a location of interest can be specified as an arbitrary region, and navigation leading to the specified region is appropriately set.

23 Claims, 56 Drawing Sheets

FOREIGN PATENT DOCUMENTS

| | | |
|---|---|---|
| JP | 11-076228 | 3/1999 |
| JP | 2000-135215 | 5/2000 |
| JP | 2002-150311 | 5/2002 |
| JP | 2002200030 | 7/2002 |
| JP | 2002-306403 | 10/2002 |
| WO | WO 03/086498 A2 | 10/2003 |
| WO | WO 2004/010857 A1 | 2/2004 |

\* cited by examiner

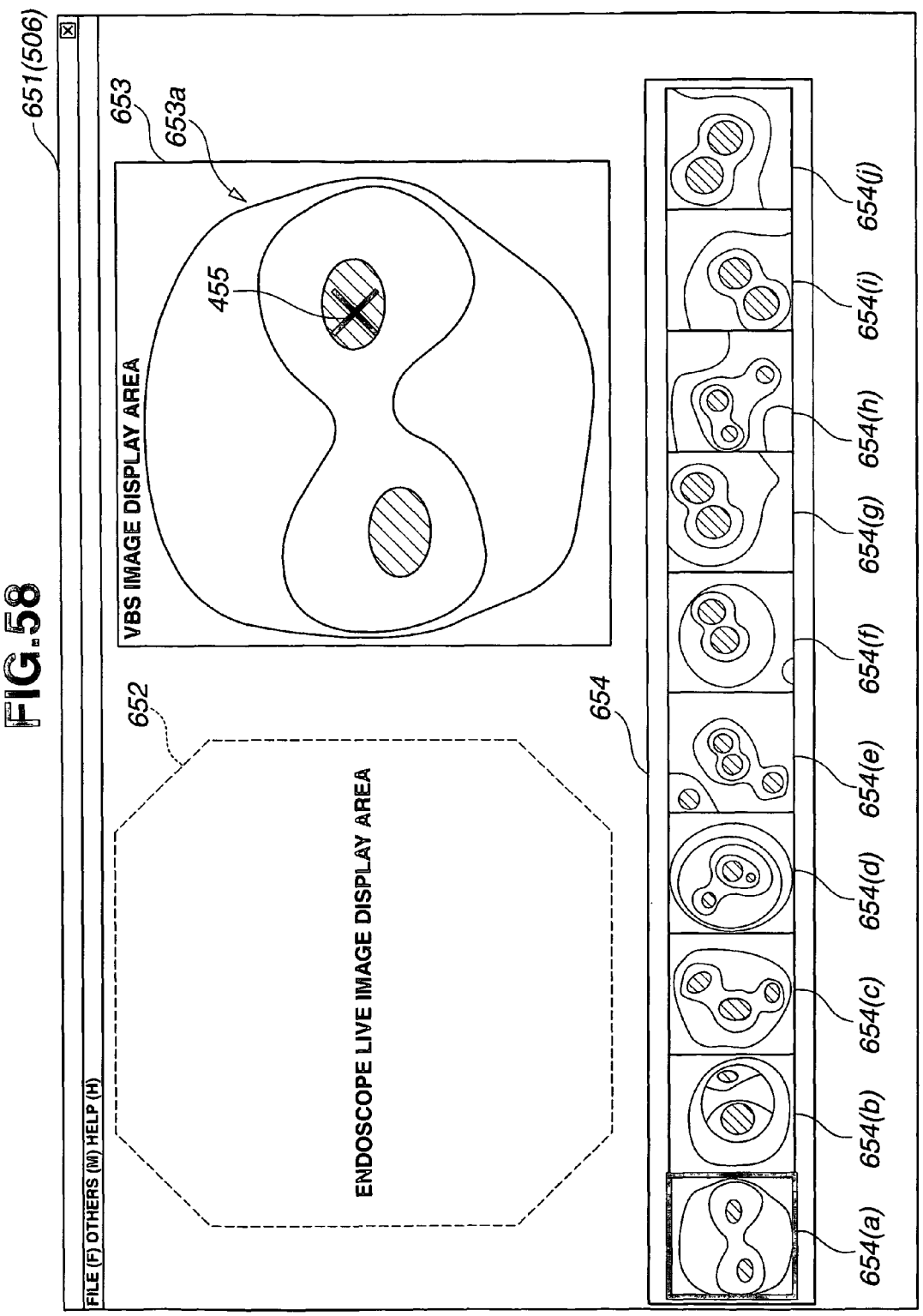

INSERTION SUPPORT SYSTEM FOR SPECIFYING A LOCATION OF INTEREST AS AN ARBITRARY REGION AND ALSO APPROPRIATELY SETTING A NAVIGATION LEADING TO THE SPECIFIED REGION

CROSS REFERENCE TO RELATED APPLICATION

This application is a continuation application of PCT/JP2004/016034 filed on Oct. 28, 2004 and claims the benefit of Japanese Applications No. 2003-373808 filed in Japan on Oct. 31, 2003, No. 2004-128489 filed in Japan on Apr. 23, 2004, and No. 2004-128490 filed in Japan on Apr. 23, 2004, the entire contents of each of which are incorporated herein by their reference.

BACKGROUND OF THE INVENTION

1. Field of the Invention

The present invention relates to an insertion support system for supporting insertion of an endoscope.

2. Description of the Related Art

In recent years, diagnosis using an image has been widely performed. For example, a cross-sectional image of a subject is captured by using an X-ray CT (Computed Tomography) apparatus or the like to obtain three-dimensional image data of the subject. The obtained three-dimensional image data is then used for diagnosing a target area.

The CT apparatus continuously performs X-ray irradiation and detection in a direction of the body axis of the subject while continuously rotating the subject. Thereby, spiral and continuous scanning (i.e., helical scanning) is performed for a three-dimensional region in the subject, and a three-dimensional image is produced from successive cross-sectional slice images of the three-dimensional region.

Such three-dimensional images include a three-dimensional image of the bronchi of the lungs. The three-dimensional image of the bronchi is used for three-dimensionally locating the position of an abnormal area suspected to contain lung cancer, for example. Then, to examine the abnormal area through a biopsy, a bronchoscope is inserted and a tissue sample is obtained by using a biopsy needle, biopsy forceps, or the like which is projected from a distal end of the bronchoscope.

In a duct within the body that branches in multiple stages, such as the bronchi, if the abnormal area is located near a periphery of a branch, it is difficult to make the distal end of the endoscope correctly reach a target location within a short time period. Therefore, Japanese Unexamined Patent Application Publication No. 2000-135215, for example, proposes an apparatus which navigates the bronchoscope to the target location by producing a three-dimensional image of the duct within the subject on the basis of image data of the three-dimensional region in the subject, determining a route leading to a target point along the duct on the three-dimensional image, producing a virtual endoscope image of the duct along the route based on the image data, and then displaying the virtual endoscope image.

SUMMARY OF THE INVENTION

An insertion support system according to the present invention includes: virtual image generating means for generating virtual images of a duct in a body cavity in a subject on the basis of image data of a three-dimensional region in the subject; route start point setting means for setting a start point of an insertion route for inserting an endoscope into the duct in the body cavity in the subject; interest region setting means for setting a region of interest location in the subject; and route end point extracting means for extracting an end point of the insertion route for inserting the endoscope into the duct in the body cavity in the subject, on the basis of the region of interest location.

BRIEF DESCRIPTION OF THE DRAWINGS

FIG. 58 is a diagram showing an insertion support screen generated by the insertion support apparatus of FIG. 39.

DETAILED DESCRIPTION OF THE PREFERRED EMBODIMENT(S)

With reference to the drawings, embodiments of the present invention will now be described below.

Embodiment 1

Figure 1:
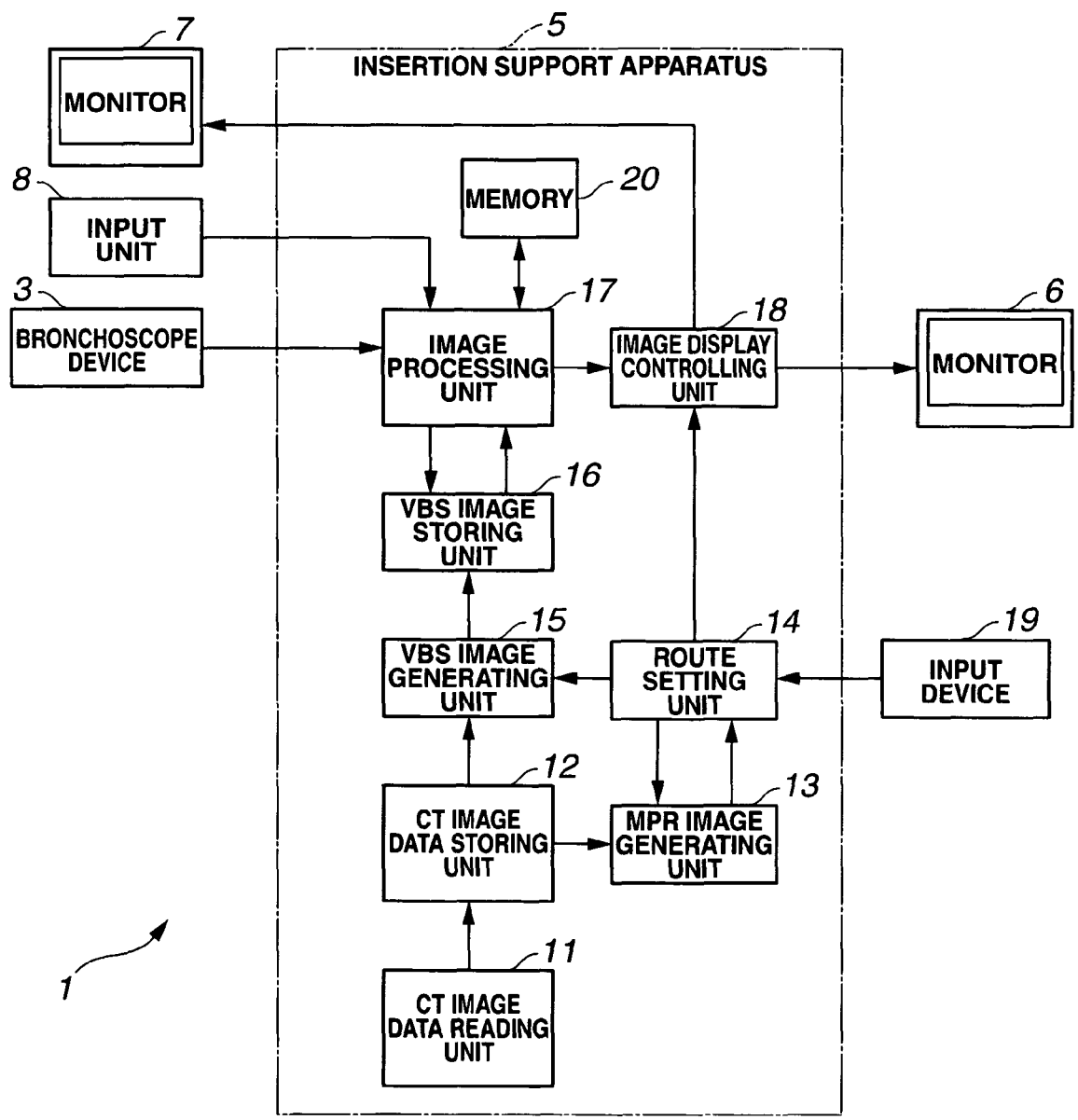
FIG. 1 is a configuration diagram illustrating a configuration of a bronchi insertion support system according to Embodiment 1 of the present invention.

As illustrated in FIG. 1, a bronchi insertion support system 1 according to the present Embodiment 1 includes a bronchoscope device 3 and an insertion support apparatus 5.

The insertion support apparatus 5 supports insertion of the bronchoscope device 3 into the bronchi by generating a virtual endoscope image (hereinafter referred to as a VBS image) of the interior of the bronchi on the basis of CT image data, combining the VBS image with an endoscope image (hereinafter referred to as a live image) obtained by the bronchoscope device 3, and displaying a resultant image on a monitor 6.

The bronchoscope device 3 includes a bronchoscope having image picking-up means, a light source for supplying illuminating light to the bronchoscope, a camera controlling unit for performing signal processing on an image pickup signal sent by the bronchoscope, and the like, which are not illustrated in the figure. The bronchoscope device 3 inserts the bronchoscope into the bronchi of a patient, captures images of the interior of the bronchi, performs a biopsy to examine target tissue located at a periphery of the bronchi, combines the live image with the VBS image, and displays a resultant image on a monitor 7.

The monitor 7 includes an input unit 8 having a touch screen so that a user can easily operate the input unit 8 including the touch screen while performing an insertion procedure.

The insertion support apparatus 5 includes a CT image data reading unit 11 which reads three-dimensional image data generated by a known CT apparatus (not illustrated) that captures X-ray cross-sectional images of a patient, through a portable data storage medium, such as an MO (Magnetic Optical disk) device, a DVD (Digital Versatile Disk) device, or the like, for example; and a CT image data storing unit 12 which stores the CT image data read by the CT image data reading unit 11. The insertion support apparatus 5 further includes an MPR image generating unit 13 which generates an MPR image (a multi-planar reformatted image) on the basis of the CT image data stored in the CT image data storing unit 12, and a route setting unit 14 which generates a route setting screen (later described) including the MPR image generated by the MPR image generating unit and which sets a support route (hereinafter simply referred to as a route) leading to the bronchi for supporting the bronchoscope device 3. The insertion support apparatus 5 further includes a VBS image generating unit 15 which serves as virtual image generating means for generating successive VBS images of the route set by the route setting unit 14 in frame units on the basis of the CT image data stored in the CT image data storing unit 12; and a VBS image storing unit 16 which stores the VBS images generated by the VBS image generating unit 15. The insertion support apparatus 5 further includes an image processing unit 17 serving as navigation screen generating means, which receives inputs of the image pickup signal sent by the bronchoscope device 3 and an input signal sent by the input unit 8 and which generates an insertion support screen (later described) including the live image, the VBS image, and a plurality of thumbnail VBS images; and an image display controlling unit 18 which displays, on the monitor 6, the route setting screen generated by the route setting unit 14 and the insertion support screen generated by the image processing unit 17. The insertion support apparatus 5 further includes an input device 19 which includes a keyboard and a pointing device for inputting set information in the route setting unit 14.

The bronchoscope device 3 receives the VBS image and the thumbnail VBS images from the image processing unit 17 of the insertion support apparatus 5, combines the received VBS image and thumbnail VBS images with the live image, and displays, on the monitor 7, a screen similar to the insertion support screen displayed on the monitor 6 by the insertion support apparatus 5. Further, the bronchoscope device 3 outputs input information sent by the input unit 8 which includes the touch screen of the monitor 7, to the image processing unit 17 of the insertion support apparatus 5.

The CT image data storing unit 12 and the VBS image storing unit 16 may be formed by one hard disk. Further, the MPR image generating unit 13, the route setting unit 14, the VBS image generating unit 15, and the image processing unit 17 may be formed by one arithmetic processing circuit. The CT image data reading unit 11 described above reads the CT image data through the portable data storage medium, such as the MO, the DVD, or the like. If a CT apparatus or an in-house server which stores the CT image data is connected to an in-house LAN, the CT image data reading unit 11 may be formed by an interface circuit connectable to the in-house LAN so that the CT image data is read through the in-house LAN.

Operations according to the thus configured present embodiment will now be described.

Figure 2:
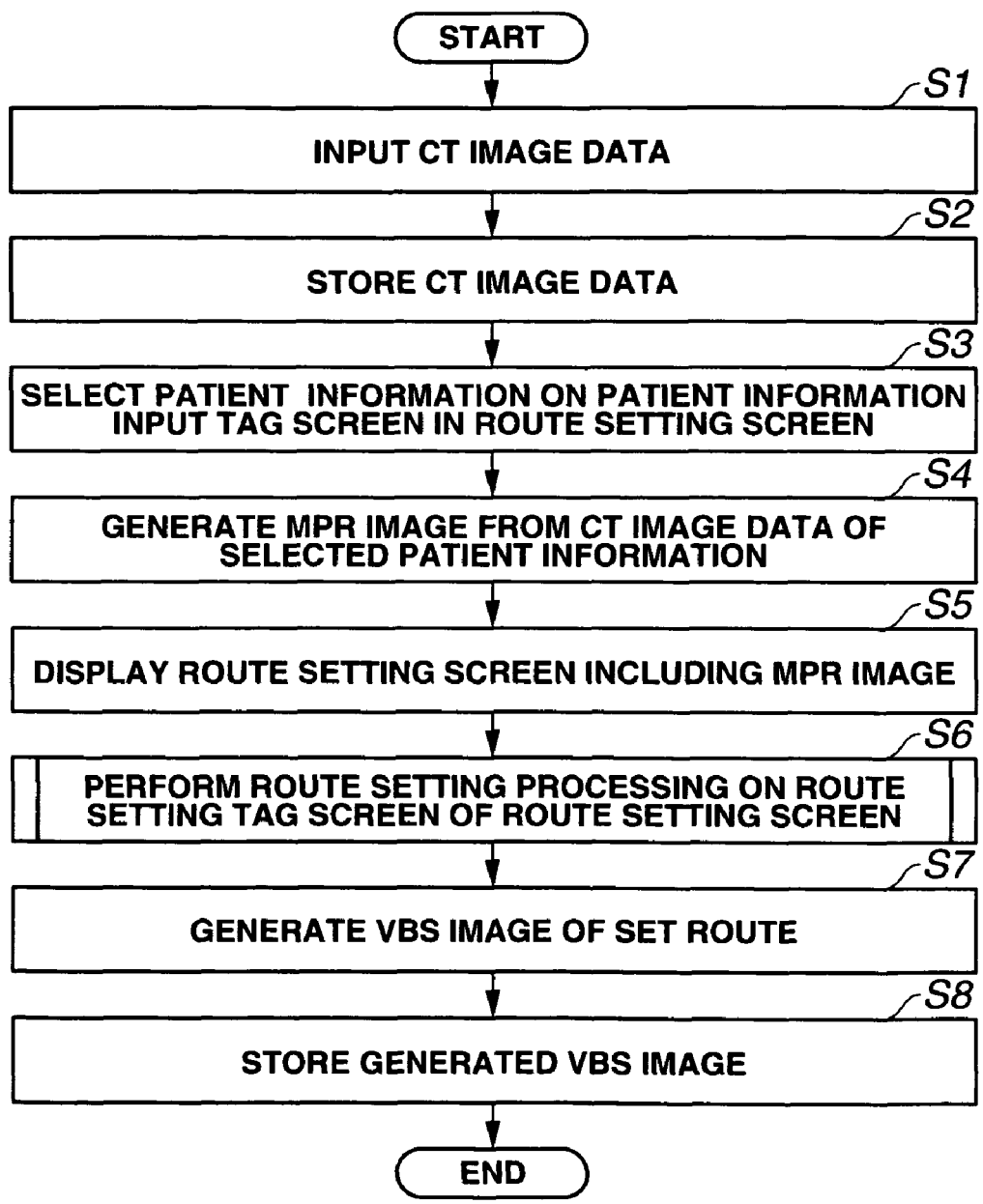
FIG. 2 is a flowchart illustrating a flow of a navigation data generating processing performed by the insertion support apparatus of FIG. 1.

As illustrated in FIG. 2, prior to observation and treatment using the bronchoscope device 3, in the insertion support apparatus 5, the CT image data reading unit 11 reads the CT image data of the patient generated by the CT apparatus at Step S1. The thus read CT image data is stored in the CT image data storing unit 12 at Step S2.

Figure 3:
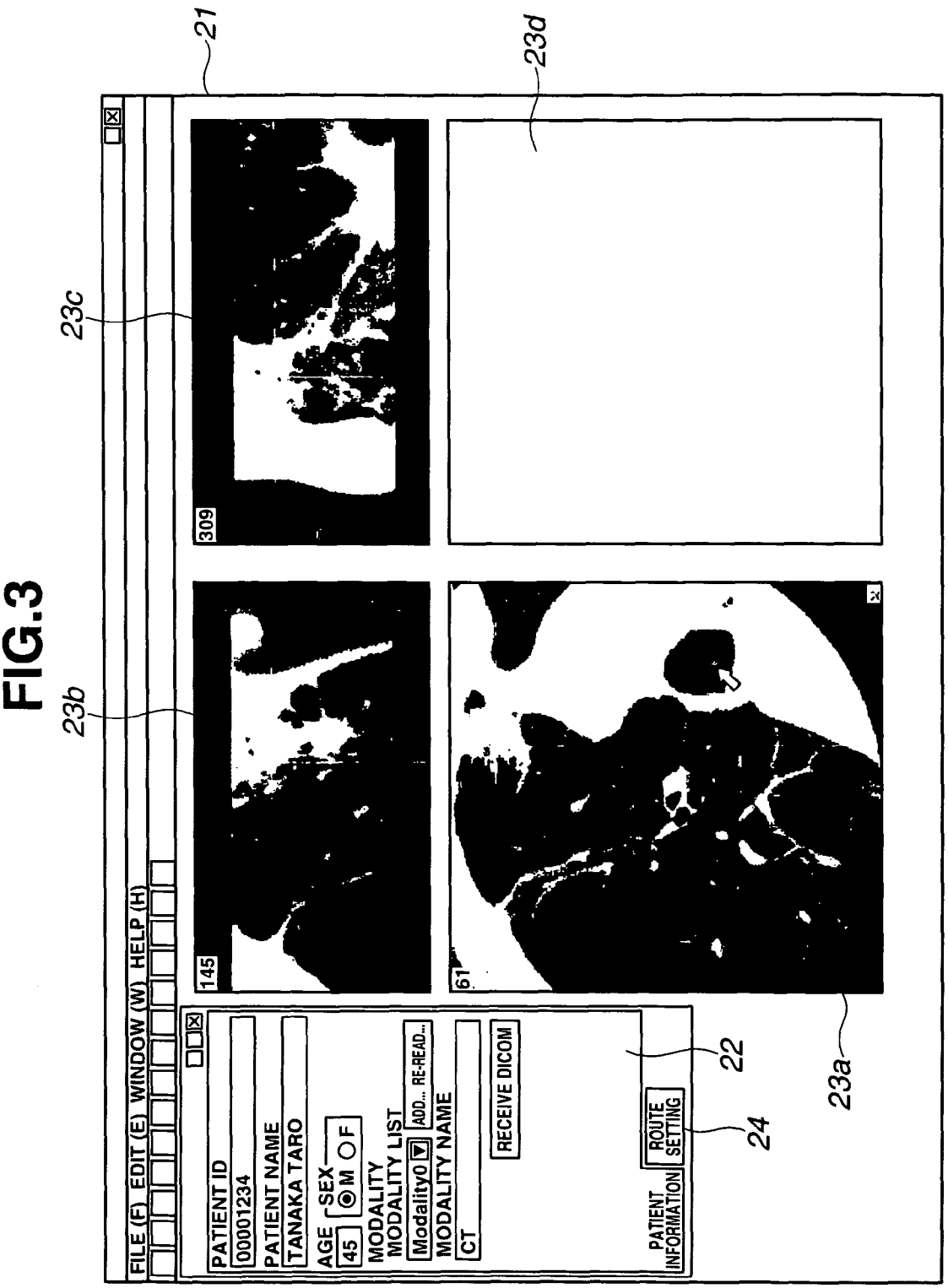
FIG. 3 is a first diagram showing a route setting screen appearing in the processing of FIG. 2.

At Step S3, the route setting unit 14 displays a route setting screen 21 as shown in FIG. 3 on the monitor 6, and patient information is selected in a patient information tag screen 22 on the route setting screen 21. Upon this selection, MPR images including, for example, three different multi-planar images of the selected patient are generated at Step S4. The thus generated MPR images 23*a*, 23*b*, and 23*c* are displayed on the route setting screen 21 at Step S5. The route setting screen 21 includes a VBS image display area 23*d* for displaying the VBS image.

The selection of the patient information on the patient information tag screen 22 is made by inputting through the input device 19 a patient ID which identifies one of the patients.

Figure 4:
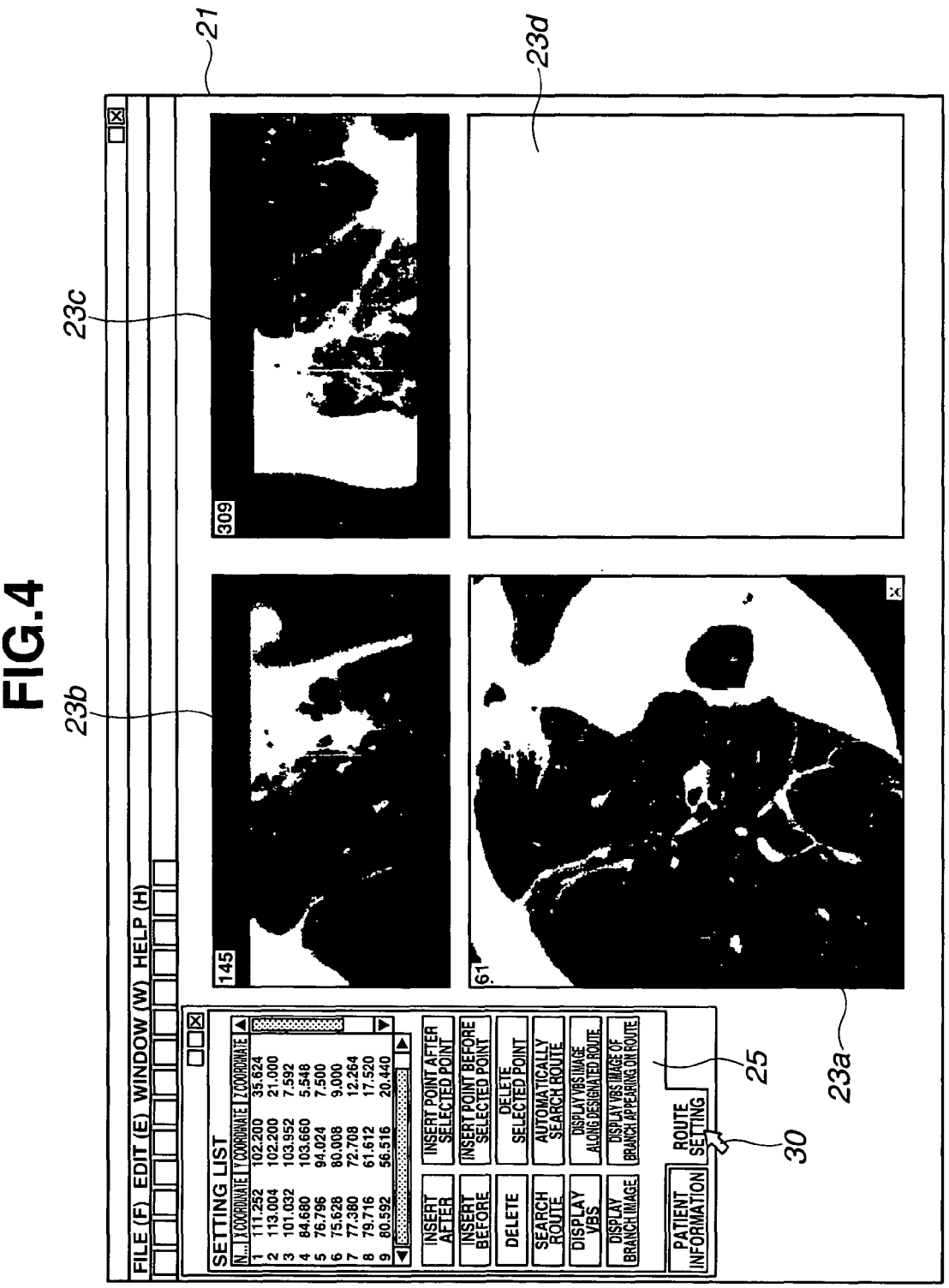
FIG. 4 is a second diagram showing the route setting screen appearing in the processing of FIG. 2.

Then, at Step S6, a route setting tag 24 (refer to FIG. 3) on the route setting screen 21 is selected by using the input device 19. Thereby, a route setting tag screen 25 as shown in FIG. 4 is displayed on the route setting screen 21, and a route setting processing (later described) is performed to set a route in the bronchi for supporting insertion of the bronchoscope.

When the route for supporting the insertion has been set, successive VBS images of the entirety of the set route are generated in frame units by the VBS image generating unit 15 at Step S7. The generated VBS images are stored in the VBS image storing unit 16 at Step S8.

As the above processings of Steps S1 to S8 are performed, preparation for the insertion support performed by the insertion support apparatus 5 in the observation and treatment using the bronchoscope is completed.

With reference to FIGS. 5 to 8, the route setting processing performed at Step S6 will now be described.

Figure 5:
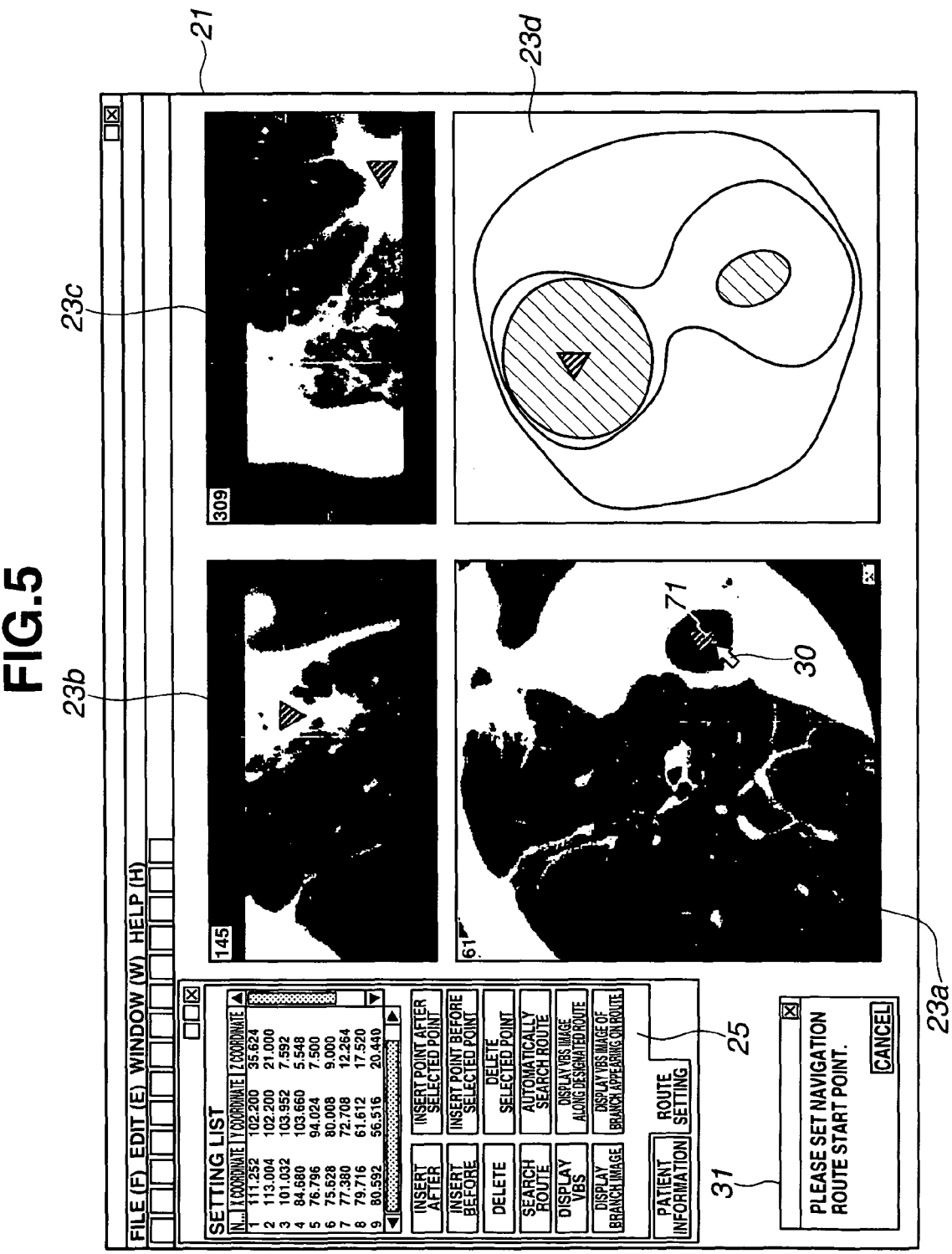
FIG. 5 is a third diagram showing the route setting screen appearing in the processing of FIG. 2.

When a route search button is selected on the route setting screen 21, the route setting processing of Step S6 is started. Specifically, a start point input command window 31 as shown in FIG. 5, which prompts input of a route start point, is displayed on the route setting screen 21. Then, a start point 71 is set on one of the cross-sectional images forming the MPR images 23*a*, 23*b* and 23*c* by using a cursor 30 on the route setting screen 21. Upon setting of the start point 71, the start point 71 is also set at a corresponding position in each of the other two cross-sectional images forming the MPR images 23*a*, 23*b* and 23*c*. Further, the VBS image of the start point 71 is displayed in the VBS image display area 23*d*. Furthermore, a biopsy area input command window 32 as shown in FIG. 6, which prompts setting of a biopsy area 72, i.e., a route end point, is displayed on the route setting screen 21.

Figure 6:
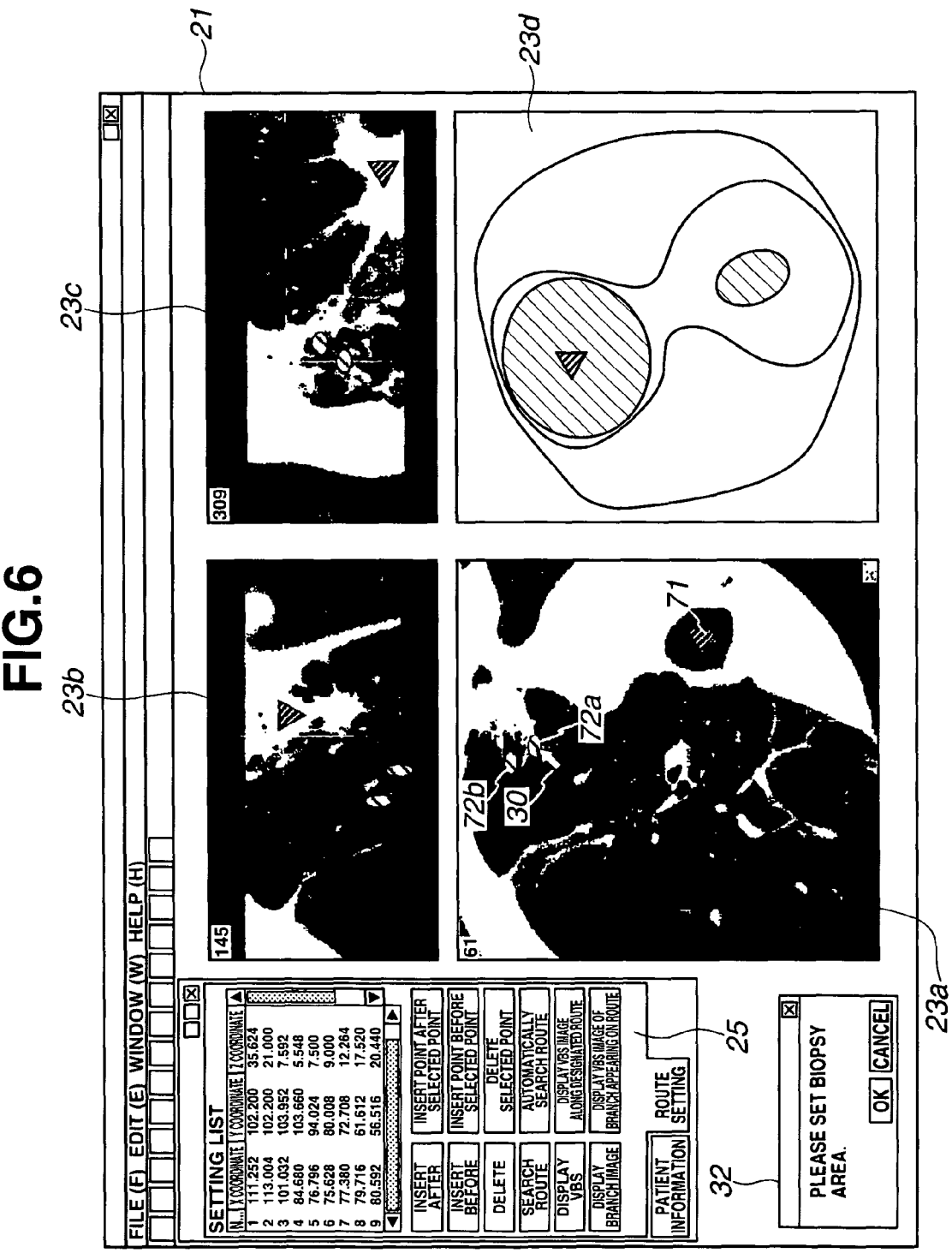
FIG. 6 is a fourth diagram showing the route setting screen appearing in the processing of FIG. 2.

Then, the biopsy area 72 is set by tracing it two-dimensionally on one of the cross-sectional images forming the MPR image 23 by using the cursor 30 on the route setting screen 21 shown in FIG. 6. The number of the thus set biopsy area 72 is not limited to one, but a plurality of the biopsy areas 72 can be specified. FIG. 6 illustrates a state in which two biopsy areas 72*a* and 72*b* are specified.

Figure 7:
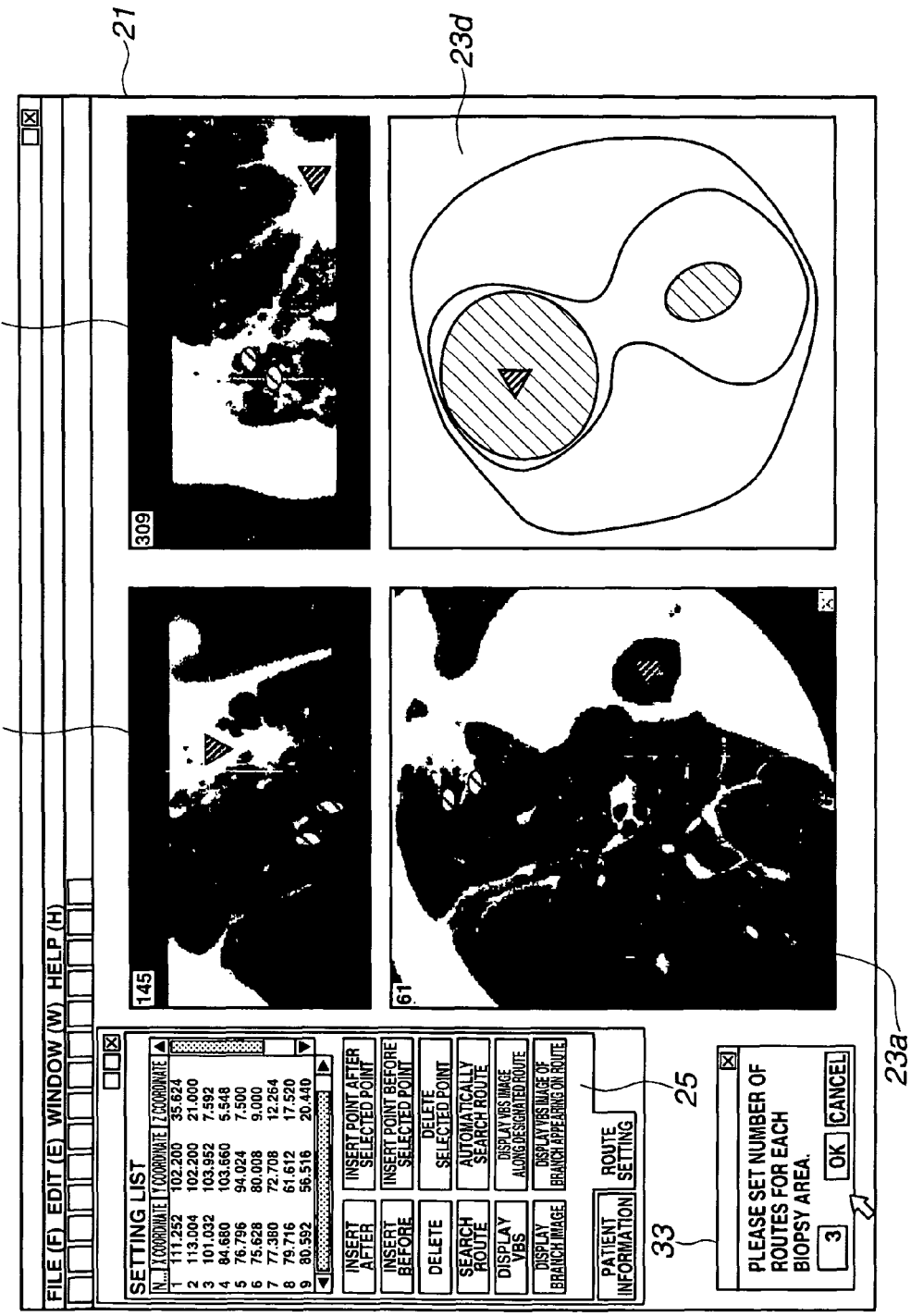
FIG. 7 is a fifth diagram showing the route setting screen appearing in the processing of FIG. 2.

Then, upon completion of the setting of the biopsy areas 72, a route number setting window 33 as shown in FIG. 7, which is used for setting the number of search routes for each of the biopsy areas 72, is displayed on the route setting screen 21. By setting the number of search routes for each of the biopsy areas 72, a plurality of approach routes are searched for each of the biopsy areas 72 of the navigation target.

Figure 8:
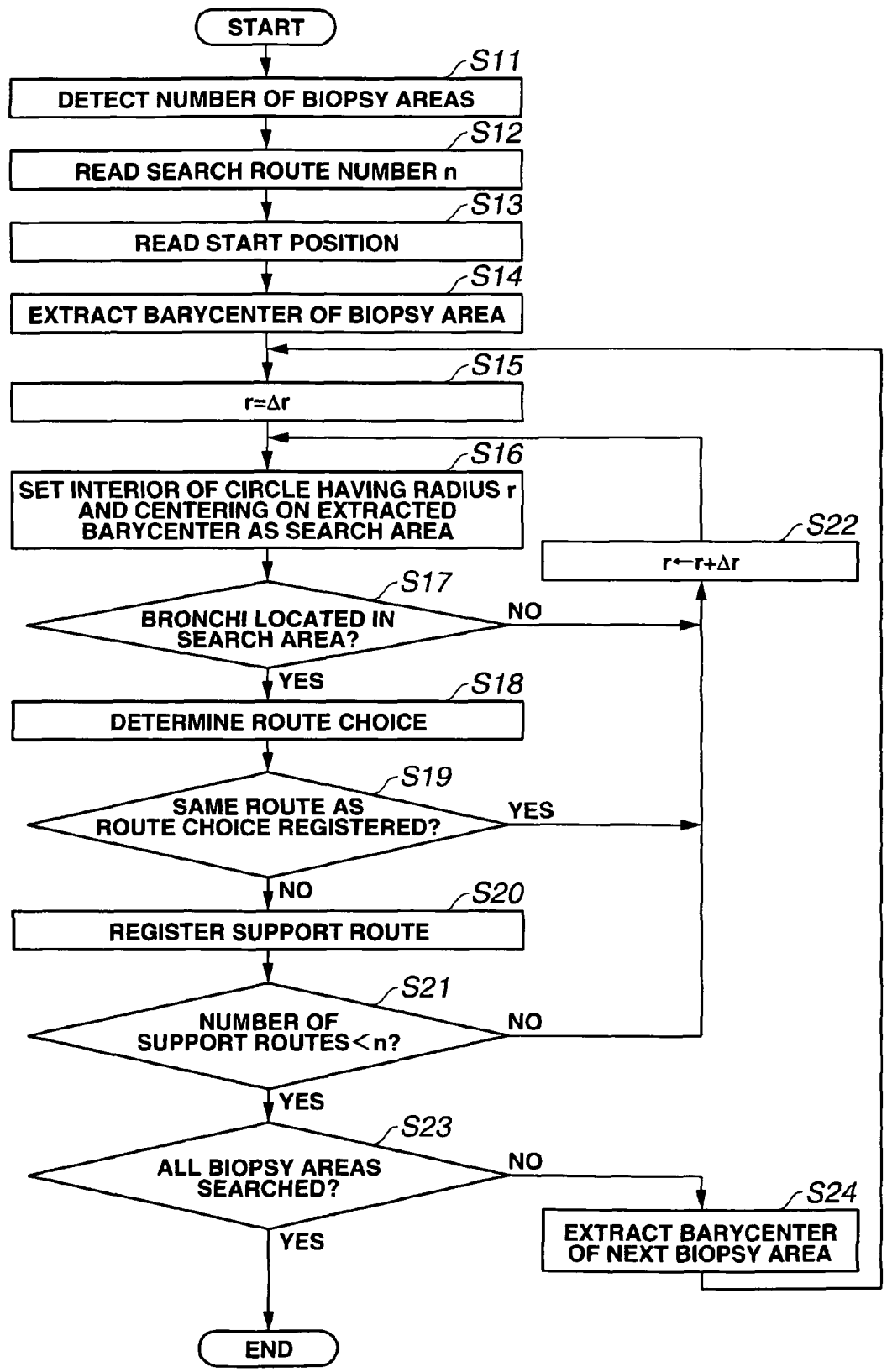
FIG. 8 is a flowchart illustrating a flow of the route setting processing of FIG. 2.

After the start point, the biopsy areas 72, and the number of search routes have been set as illustrated in FIGS. 5 to 7, the routes are searched in accordance with the processing of FIG. 8.

That is, as illustrated in FIG. 8, the set number of the biopsy areas 72 is detected at Step S1, and a search route number n is read at Step S12. Then, the position of the start point 71 is read at Step S13.

Then, the barycentric position of one of the biopsy areas 72 is extracted at Step S14, and a value r is adjusted to a value Δr at Step S15. Thereafter, at Step S16, the interior of a circle having a radius r and centering on the barycentric position is specified as a search area.

At Step S17, it is determined whether the bronchi are located within the search area. If it is determined that the bronchi are located within the search area, a route choice having the position as the end point is determined at Step S18.

After the route choice has been determined, it is determined at Step S19 whether the route choice determined at Step S19 has already been registered. If it is determined that the route choice determined at Step S19 has not been registered yet, at Step S20, a route name is generated on the basis of the name of a branch point connecting the start point and the end point, and the route choice is registered as a support route.

Then, at Step S21, it is determined whether the number of the registered routes is smaller than the route number n read at Step S12.

If it is determined at Step S17 that the bronchi are not located within the search area, if it is determined at Step S19 that the determined route choice has already been registered, or if it is determined at Step S21 that the number of the registered routes is smaller than the route number n, the value r is adjusted to a value r+Δr to expand the search area. Then, the flow returns to Step S16.

If the number of the registered routes reaches the route number n read at Step S12, it is determined at Step S23 whether all of the set biopsy areas have been searched. If it is determined that all of the set biopsy areas have been searched, the processing ends. If it is determined that there is any unsearched biopsy area, the barycentric position of a next biopsy area is extracted at Step S24, and the flow returns to Step S15.

Figure 9:
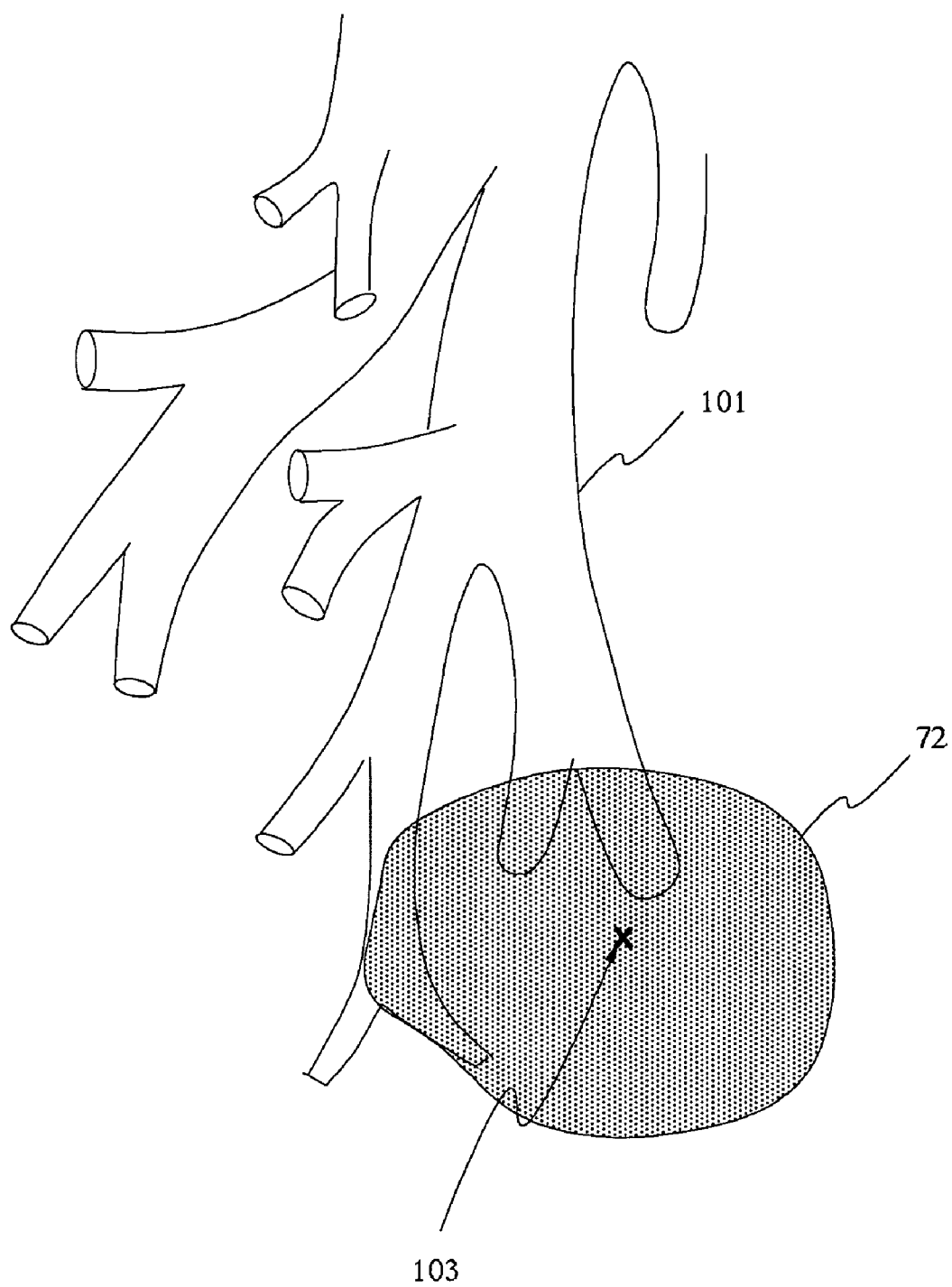
FIG. 9 is a first diagram illustrating the processing of FIG. 8.

Specifically, as illustrated in FIG. 9, if the biopsy area 72 is specified in a periphery of the bronchi 101, the barycenter 103 of the biopsy area 72 is extracted.

Figure 10:
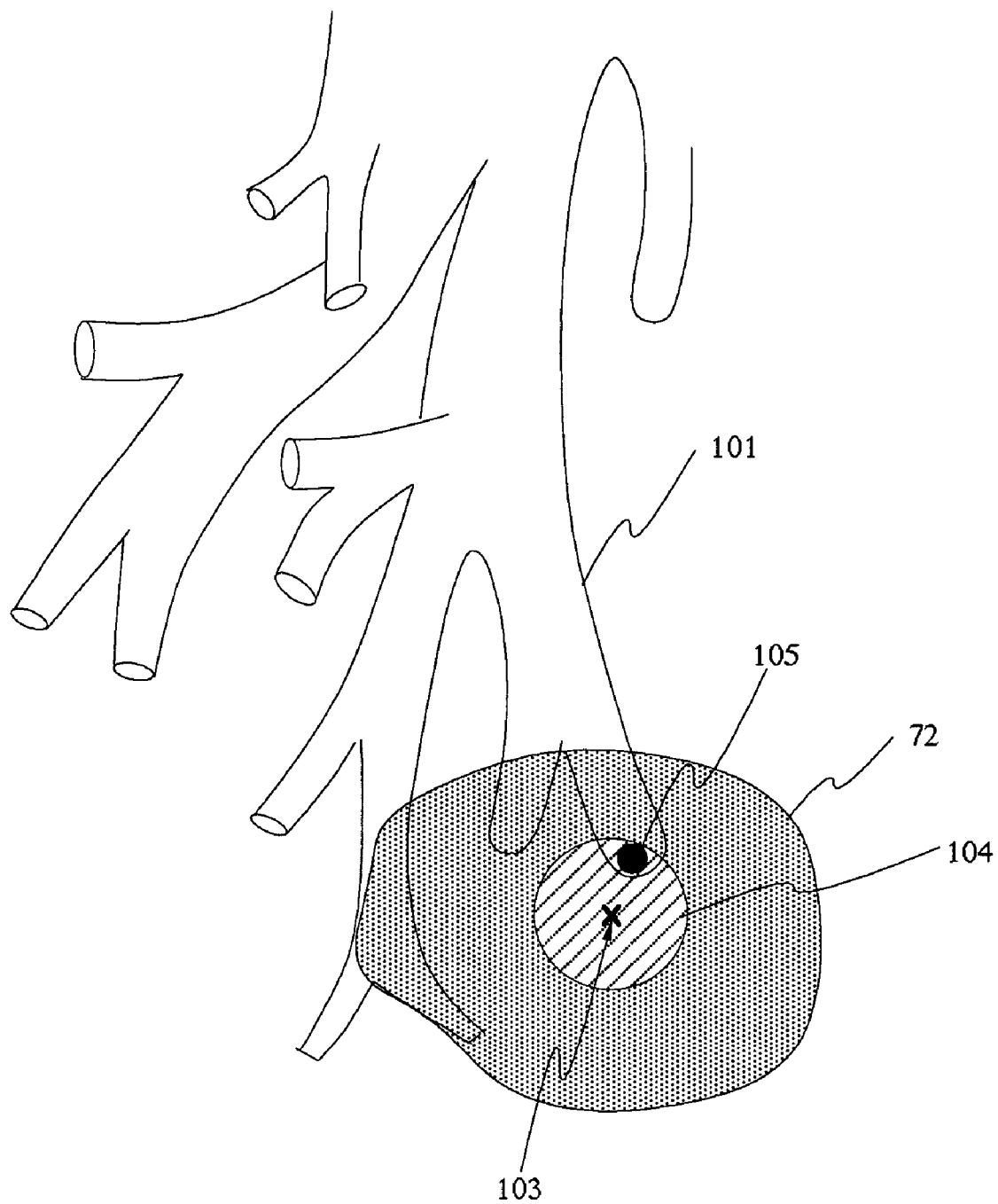
FIG. 10 is a second diagram illustrating the processing of FIG. 8.
Figure 11:
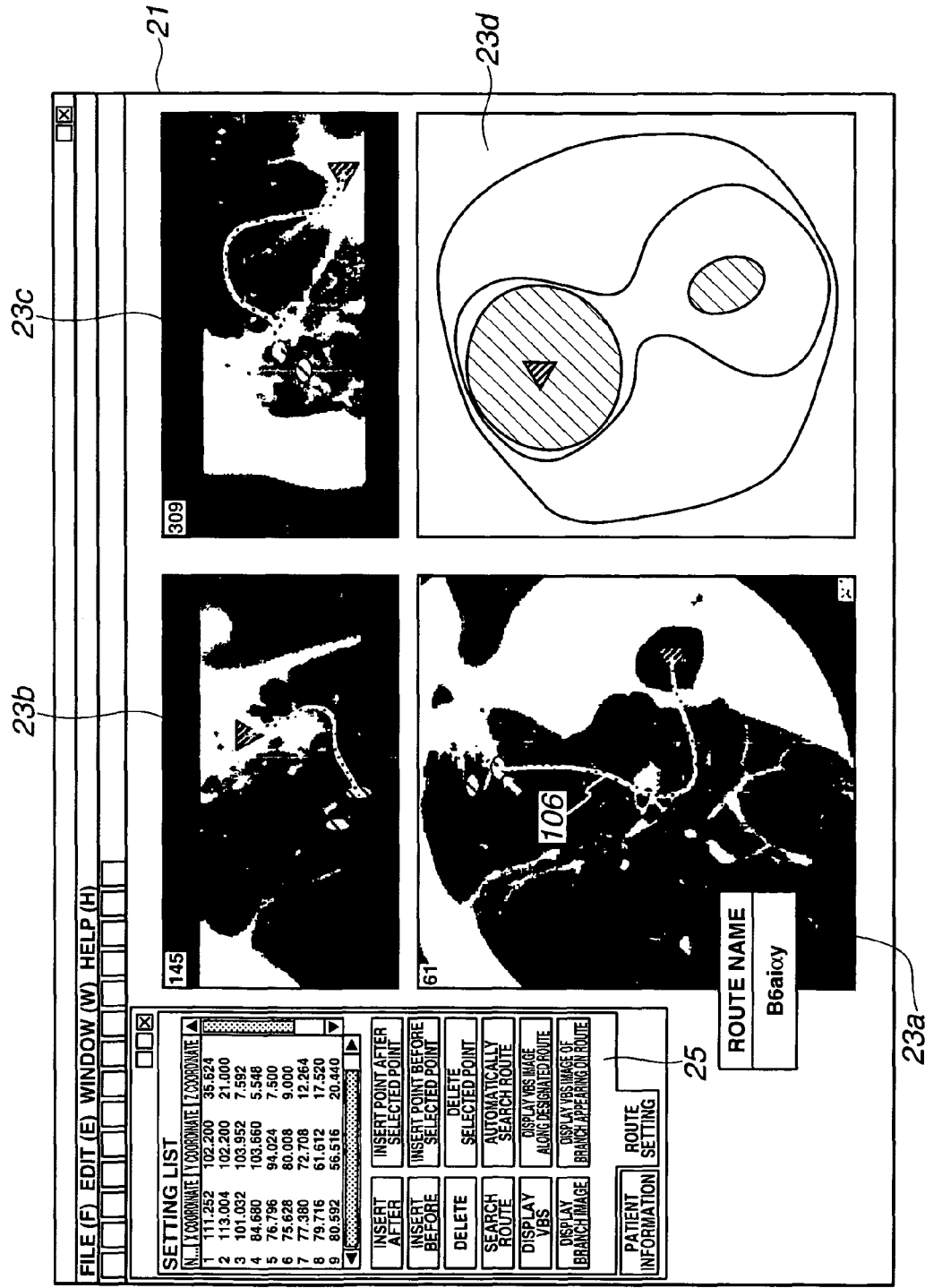
FIG. 11 is a first diagram showing a route setting screen appearing in the processing of FIG. 8.

Then, as illustrated in FIG. 10, a circle centering on the barycenter 103 is determined as a search area 104, and the search area 104 is expanded until the bronchi are located within the search area 104. A point in the search area 104 to which the bronchi first reach is determined as an end point 105. Then, as illustrated in FIG. 11, a first route choice 106 connecting the start point 71 and the end point 105 is determined. If the first route choice 106 has not been registered yet, the first route choice 106 is registered as a support route. The name of the support route is determined on the basis of the name of a branch point through which the support route passes.

Figure 12:
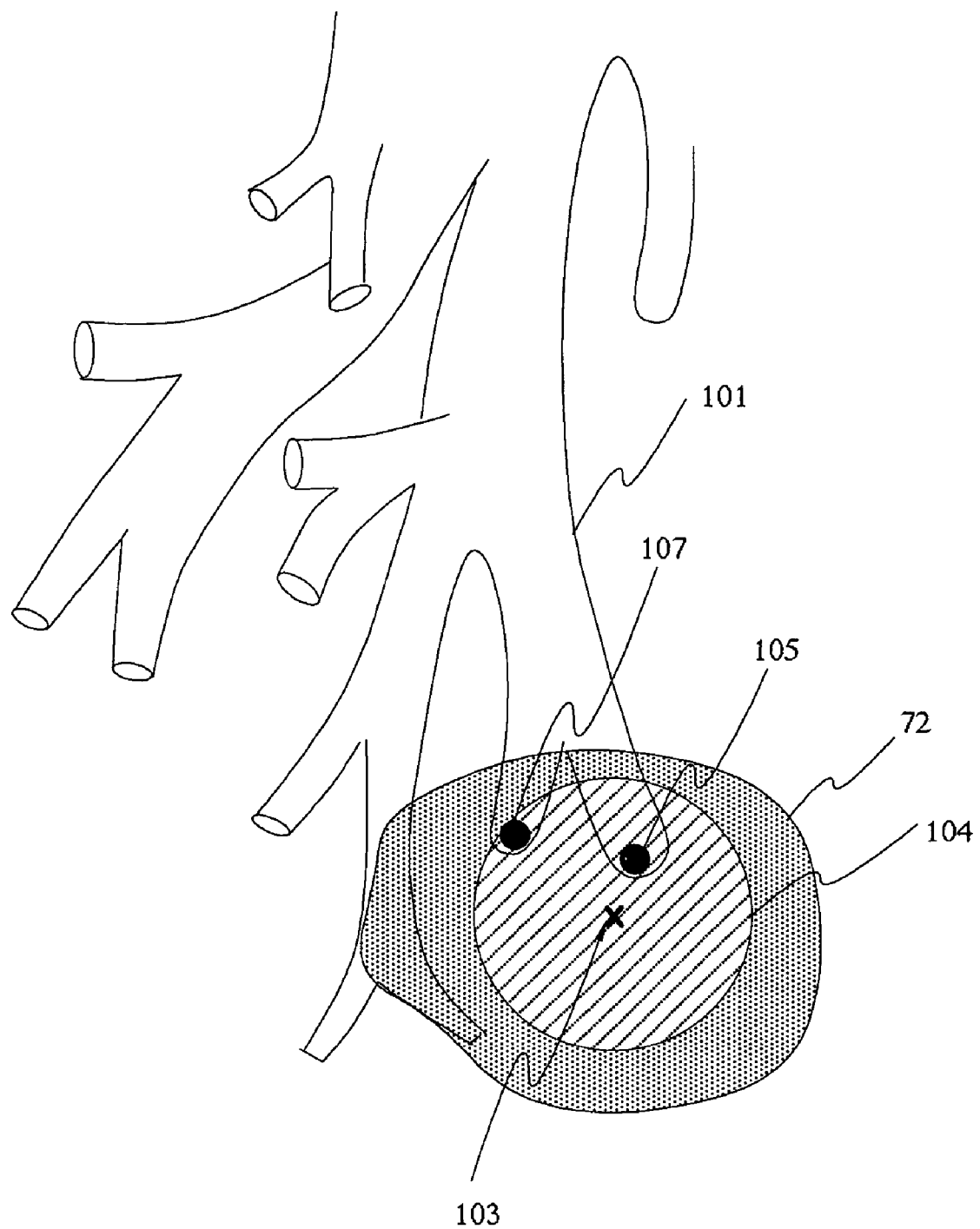
FIG. 12 is a third diagram illustrating the processing of FIG. 8.
Figure 13:
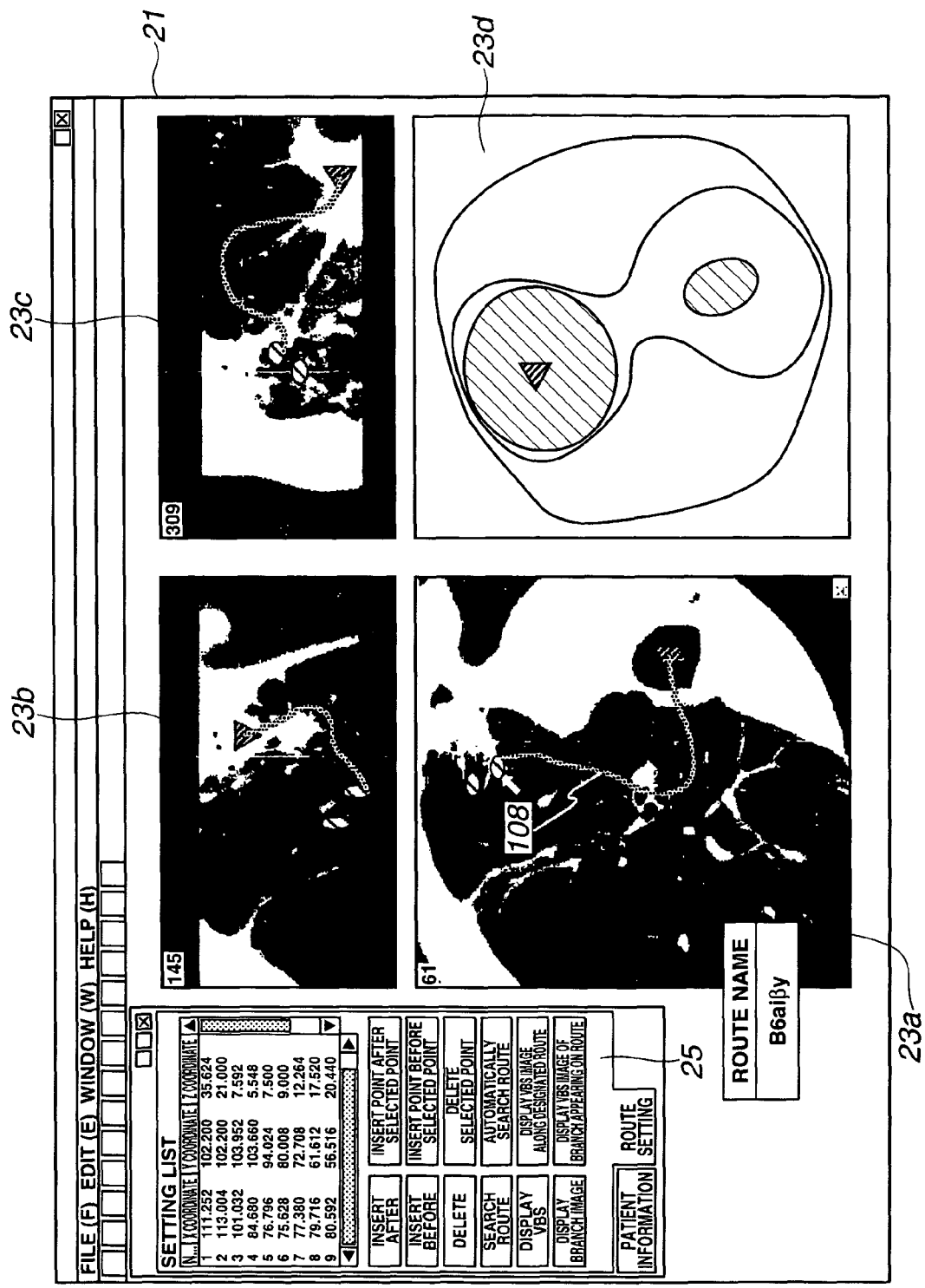
FIG. 13 is a second diagram showing the route setting screen appearing in the processing of FIG. 8.

As the first support route has been determined, as illustrated in FIG. 12, the radius of the search area 104 centering on the barycenter 103 is increased to expand the search area 104. Then, a position in the search area 104 to which the bronchi next reach is determined as an end point 107. Thereby, a second route choice 108 connecting the start point 71 and the end point 107 is determined, as illustrated in FIG. 13. If it is determined that the second route choice 108 has not been registered yet, the second route choice 108 is registered as a support route. In FIG. 13, the second route choice 108 is different from the first support route shown in FIG. 11. Therefore, the second route choice 108 forms the second support route. The name of the support route is also determined on the basis of the name of a branch point through which the support route passes.

Figure 14:
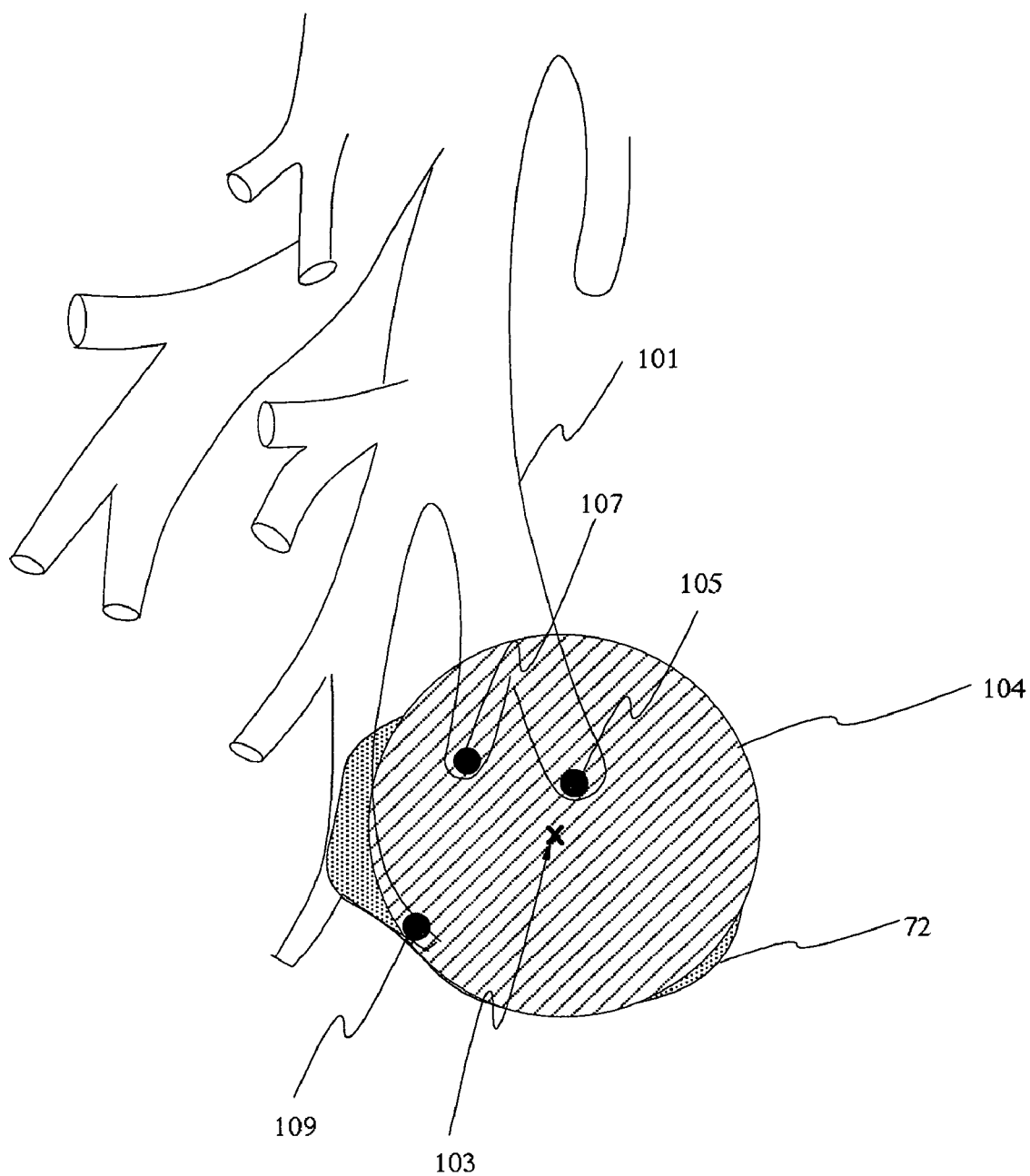
FIG. 14 is a fourth diagram illustrating the processing of FIG. 8.
Figure 15:
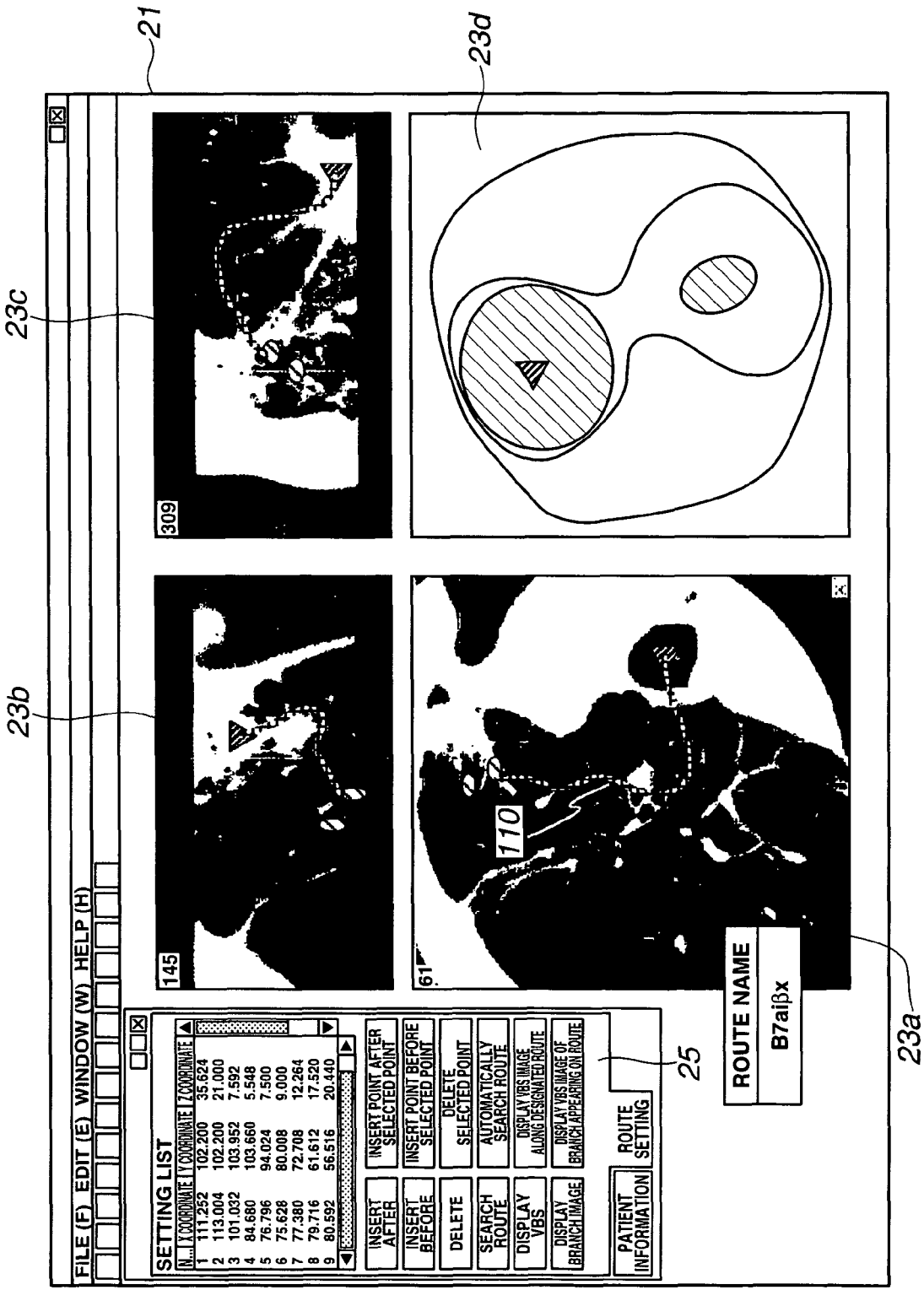
FIG. 15 is a third diagram showing the route setting screen appearing in the processing of FIG. 8.

In the present embodiment, the route number is three. Therefore, in an exactly similar manner as described above, after the second support route has been determined, as illustrated in FIG. 14, the radius of the search area 104 centering on the barycenter 103 is further increased to expand the search area 104. Then, a position in the search area 104 to which the bronchi next reach is determined as an end point 109. Thereby, a third route choice 110 connecting the start point 71 and the end point 109 is determined, as illustrated in FIG. 15. If it is determined that the third route choice 110 has not been registered yet, the third route choice 110 is registered as a support route. In FIG. 15, the third route choice 110 is different from the first and second support routes. Therefore, the third route choice 110 forms the third support route. The name of the support route is also determined on the basis of the name of a branch point through which the support route passes.

In this way, the specified number of support routes can be set. The above processings are performed for all of the biopsy areas 72, and thus the specified route number of support routes are set for each of the biopsy areas 72.

Figure 16:
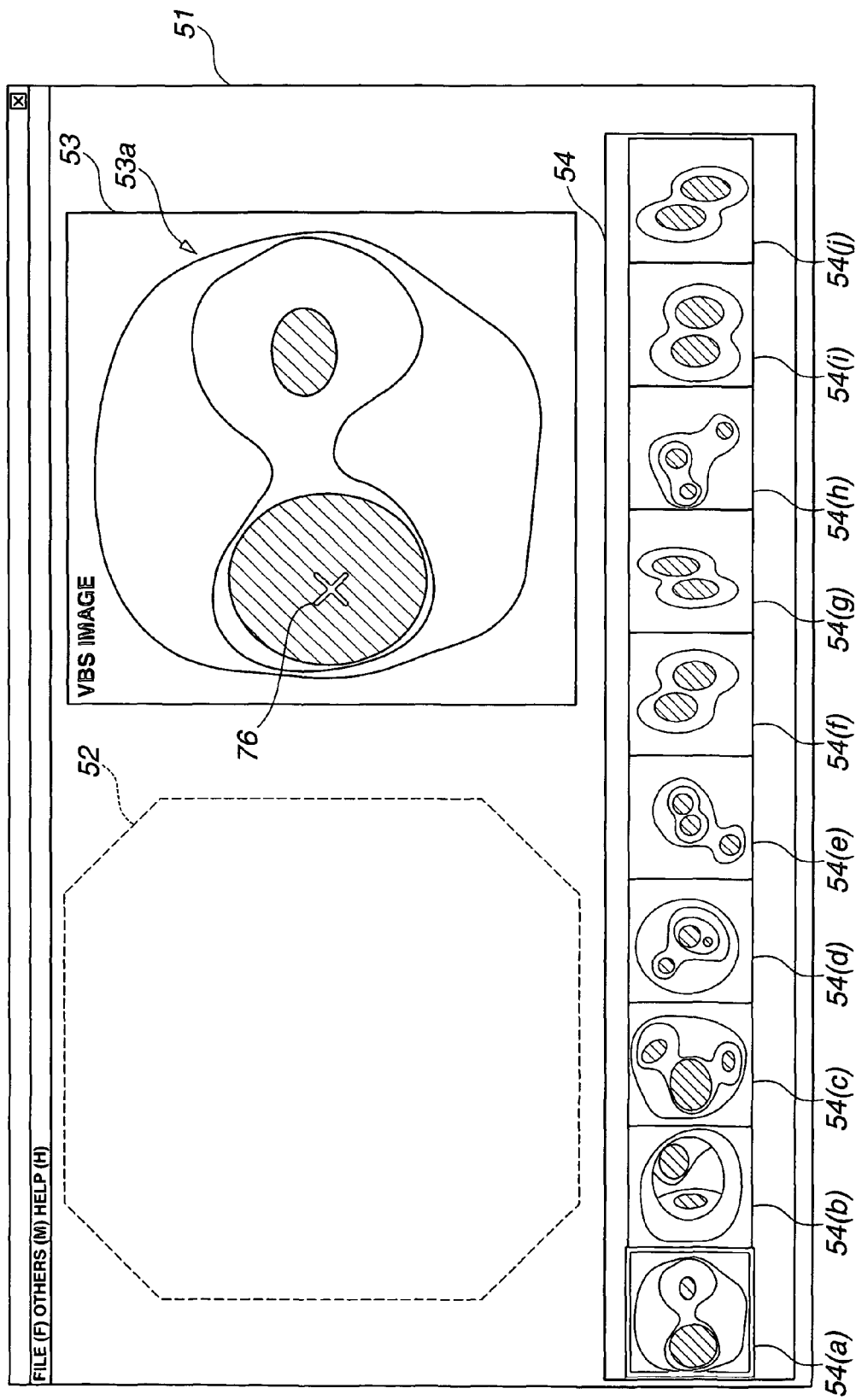
FIG. 16 is a diagram showing an insertion support screen appearing in the processing of FIG. 2.

When a bronchoscopic examination is started under the insertion support performed by the insert support apparatus 5 along the thus set support route, an insertion support screen 51 as shown in FIG. 16 is displayed on the monitor 7. Further, another insertion support screen 51 similar to the insertion support screen 51 displayed on the monitor 7 is also displayed on the monitor 6.

The insertion support screen 51 includes an endoscope live image display area 52 for displaying the live image sent by the bronchoscope device 3, a VBS image display area 53 for displaying a VBS image 53a, and a branch thumbnail VBS image area 54 for displaying branch thumbnail VBS images 54(a) to 54(j) which are reduced size images of the VBS image 53a at all of the branch points on the route. The VBS image 53a is displayed in the VBS image display area 53 as a virtual image corresponding to one of the branch points at which the live image is located.

One of the branch thumbnail VBS images similar to the VBS image 53a displayed in the VBS image display area 53 is framed in color or by a bold line to be distinguished from the other branch thumbnail VBS images. Accordingly, a surgeon can easily recognize which one of the branch images corresponds to the VBS image displayed in the VBS image display area 53.

Figure 17:
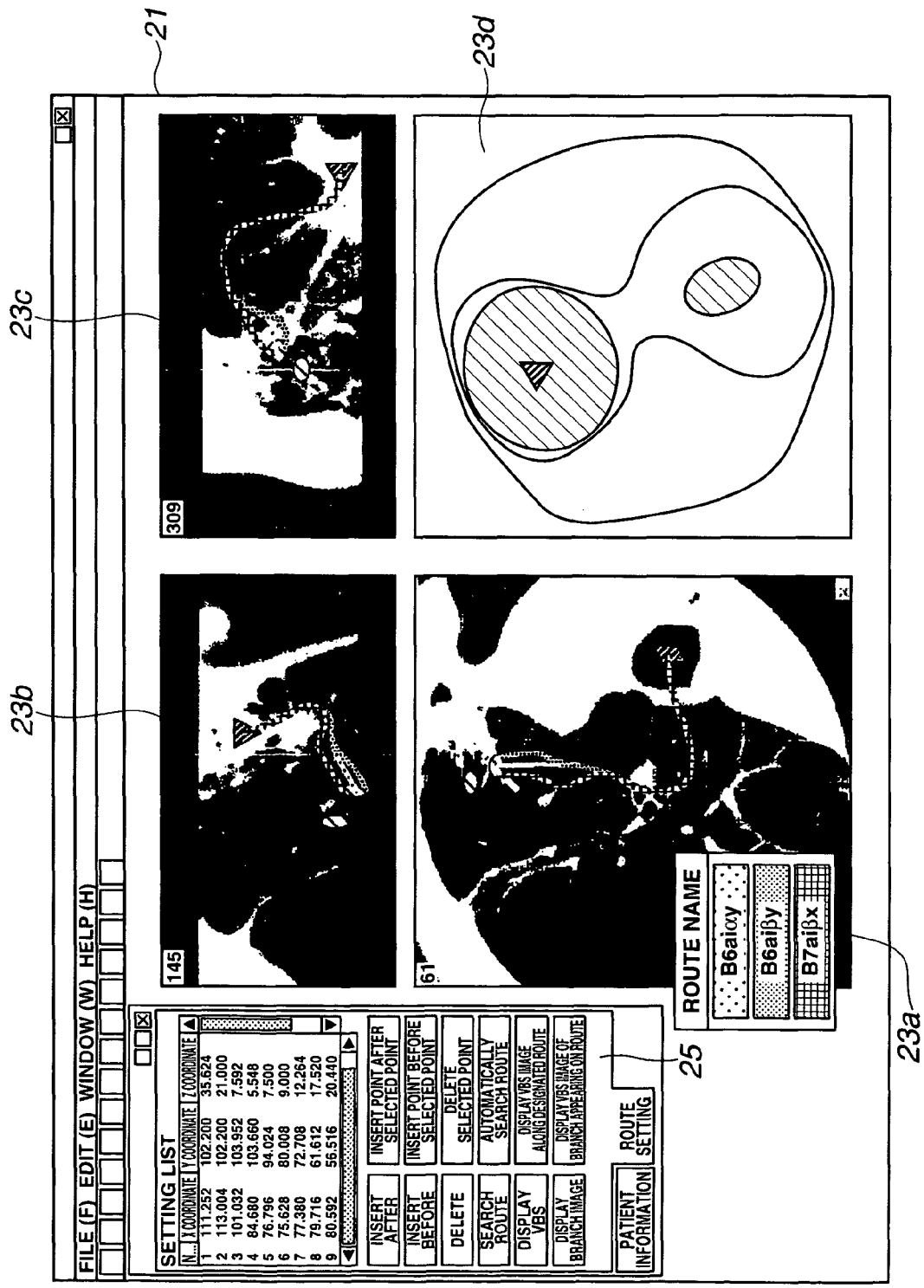
FIG. 17 is a diagram showing a second modified example of the route setting screen appearing in the processing of FIG. 8.
Figure 18:
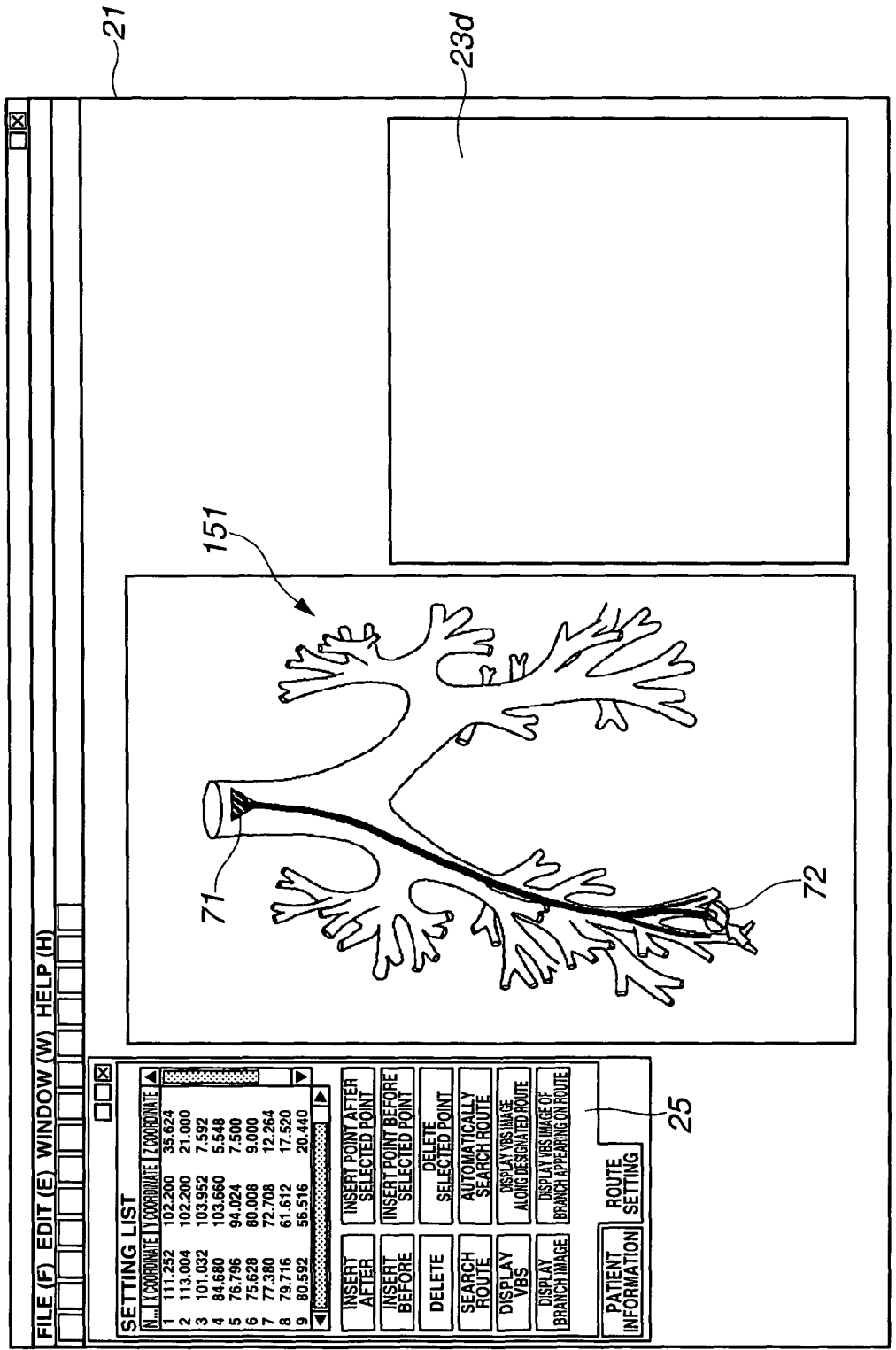
FIG. 18 is a diagram showing a first modified example of the route setting screen appearing in the processing of FIG. 8.

As illustrated in FIG. 17, all of the support routes may be displayed on the MPR images 23a, 23b and 23c at the same time, with the respective support routes marked with different colors. As described above, the start point and the biopsy areas are specified on the MPR image 23. However, the specification of the start point and the biopsy areas is not limited thereto. Therefore, as illustrated in FIG. 18, a three-dimensional image 151 of the bronchi may be displayed on the route setting screen 21 so that the start point 71 and the biopsy area 72 are specified on the three-dimensional image 151 to perform the route search.

Embodiment 2

Figure 19:
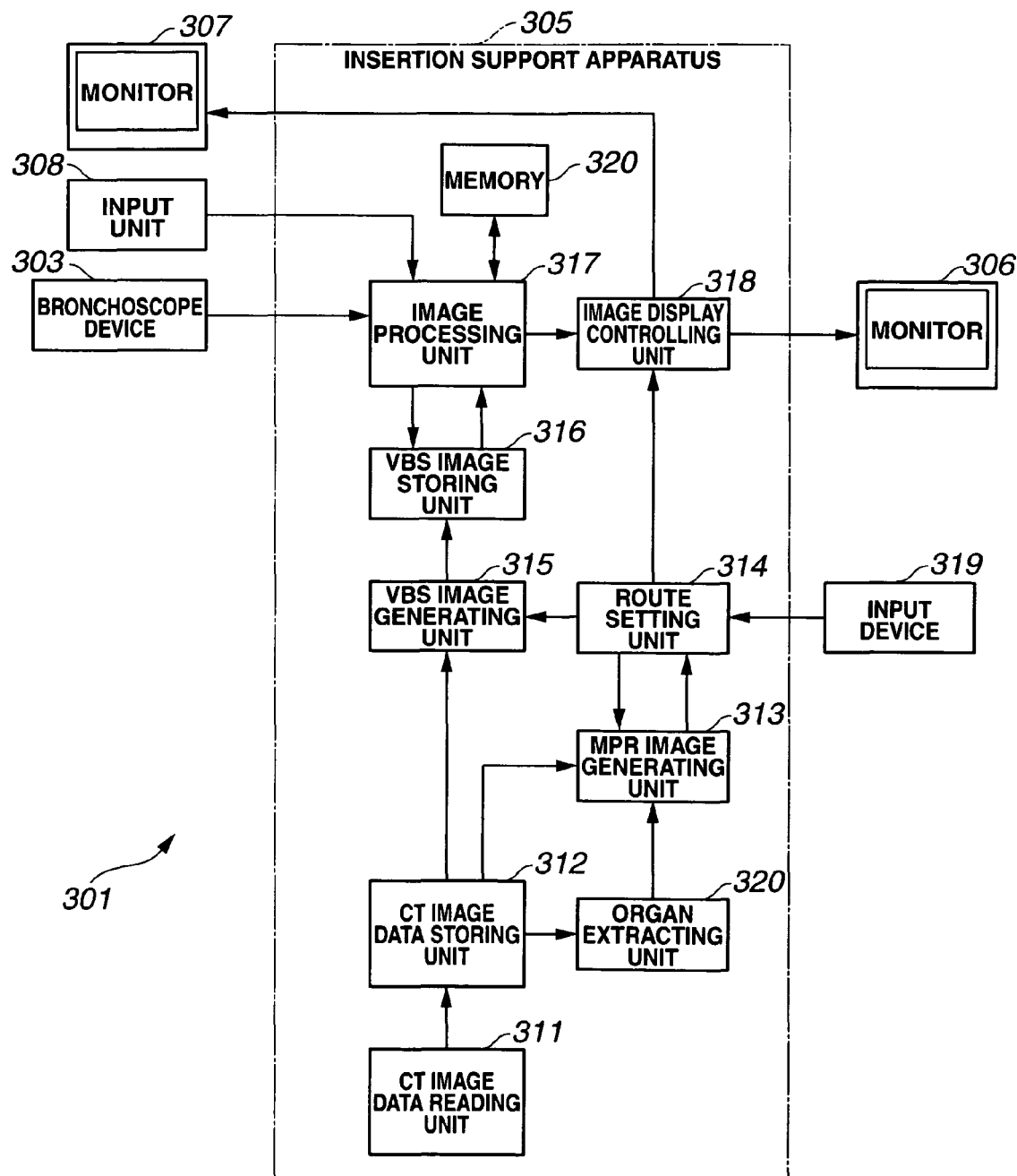
FIG. 19 is a configuration diagram illustrating a configuration of a bronchi insertion support system according to Embodiment 2 of the present invention.

As illustrated in FIG. 19, a bronchi insertion support system 301 according to the present Embodiment 2 includes a bronchoscope device 303 and an insertion support apparatus 305.

The insertion support apparatus 305 supports insertion of the bronchoscope device 303 into the bronchi by generating a virtual endoscope image (hereinafter referred to as a VBS image) of the interior of the bronchi on the basis of CT image data, combining the VBS image with an endoscope image (hereinafter referred to as a live image) obtained by the bronchoscope device 303, and displaying a resultant image on a monitor 306.

The bronchoscope device 303 includes a bronchoscope having image picking-up means, a light source for supplying illuminating light to the bronchoscope, a camera controlling unit for performing signal processing on an image pickup signal sent by the bronchoscope, and the like, which are not illustrated in the figure. The bronchoscope device 303 inserts the bronchoscope into the bronchi of a patient, captures images of the interior of the bronchi, performs a biopsy to examine target tissue located at a periphery of the bronchi, combines the live image with the VBS image, and displays a resultant image on a monitor 307.

The monitor 307 includes an input unit 308 having a touch screen so that a user can easily operate the input unit 308 including the touch screen while performing an insertion procedure.

The insertion support apparatus 305 includes a CT image data reading unit 311 which reads three-dimensional image data generated by a known CT apparatus (not illustrated) that captures X-ray cross-sectional images of a patient, through a portable data storage medium, such as an MO (Magnetic Optical disk) device, a DVD (Digital Versatile Disk) device, or the like, for example; and a CT image data storing unit 312 which stores the CT image data read by the CT image data reading unit 311. The insertion support apparatus 305 further includes an organ extracting unit 320 which extracts segmentation, i.e., three-dimensional information of the bronchi that is a predetermined organ from the CT image data stored in the CT image data storing unit 312; and an MPR image generating unit 313 which generates an MPR image (a multi-planar reformatted image) on the basis of the CT image data stored in the CT image data storing unit 312 and which displays a bronchi cross-sectional image of the bronchi extracted by the organ extracting unit 320 by superimposing the bronchi cross-sectional image on the MPR image. The insertion support apparatus 305 further includes a route setting unit 314 which generates a route setting screen (later described) including the MPR image generated by the MPR image generating unit 313 and which sets a support route (hereinafter simply referred to as a route) for guiding the bronchoscope device 303 to the bronchi. The insertion support apparatus 305 further includes a VBS image generating unit 315 which generates successive VBS images of the route set by the route setting unit 314 in frame units on the basis of the CT image data stored in the CT image data storing unit 312; and a VBS image storing unit 316 which stores the VBS images generated by the VBS image generating unit 315. The insertion support apparatus 305 further includes an image processing unit 317 which receives inputs of the image pickup signal sent by the bronchoscope device 303 and an input signal sent by the input unit 308 and which generates an insertion support screen (later described) including the live image, the VBS image, and a plurality of thumbnail VBS images; and an image display controlling unit 318 which displays, on the monitor 306, the route setting screen generated by the route setting unit 314 and the insertion support screen generated by the image processing unit 317. The insertion support apparatus 305 further includes an input device 319 which includes a keyboard and a pointing device for inputting set information in the route setting unit 314.

The bronchoscope device 303 receives the VBS image and the thumbnail VBS images from the image processing unit 317 of the insertion support apparatus 305, combines the received VBS image and thumbnail VBS images with the live image, and displays a resultant image on the monitor 307. Further, the bronchoscope device 303 outputs input information sent by the input unit 308 which includes the touch screen of the monitor 307, to the image processing unit 317 of the insertion support apparatus 305.

The CT image data storing unit 312 and the VBS image storing unit 316 may be formed by one hard disk. Further, the MPR image generating unit 313, the route setting unit 314, the VBS image generating unit 315, and the image processing unit 317 may be formed by one arithmetic processing circuit. The CT image data reading unit 311 described above reads the CT image data through the portable data storage medium, such as the MO, the DVD, or the like. If a CT apparatus or an in-house server which stores the CT image data is connected to an in-house LAN, the CT image data reading unit 311 may be formed by an interface circuit connectable to the in-house LAN so that the CT image data is read through the in-house LAN.

Operations according to the thus configured present embodiment will now be described.

Figure 20:
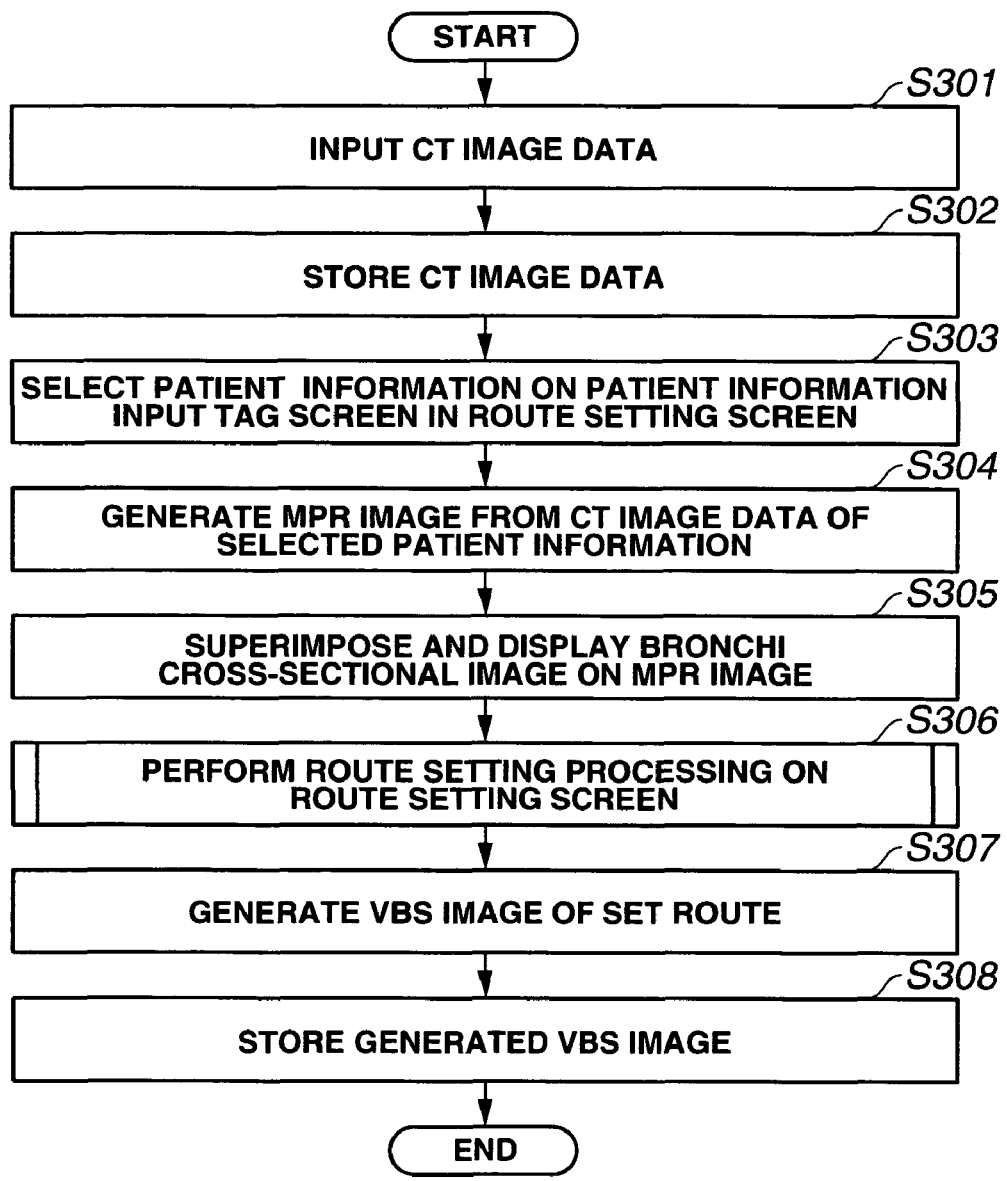
FIG. 20 is a flowchart illustrating a flow of an insertion support data generating processing performed by the insertion support apparatus of FIG. 19.

As illustrated in FIG. 20, prior to observation and treatment using the bronchoscope device 303, in the insertion support apparatus 305, the CT image data reading unit 311 reads the CT image data of the patient generated by the CT apparatus at Step S301. The thus read CT image data is stored in the CT image data storing unit 312 at Step S302.

Figure 21:
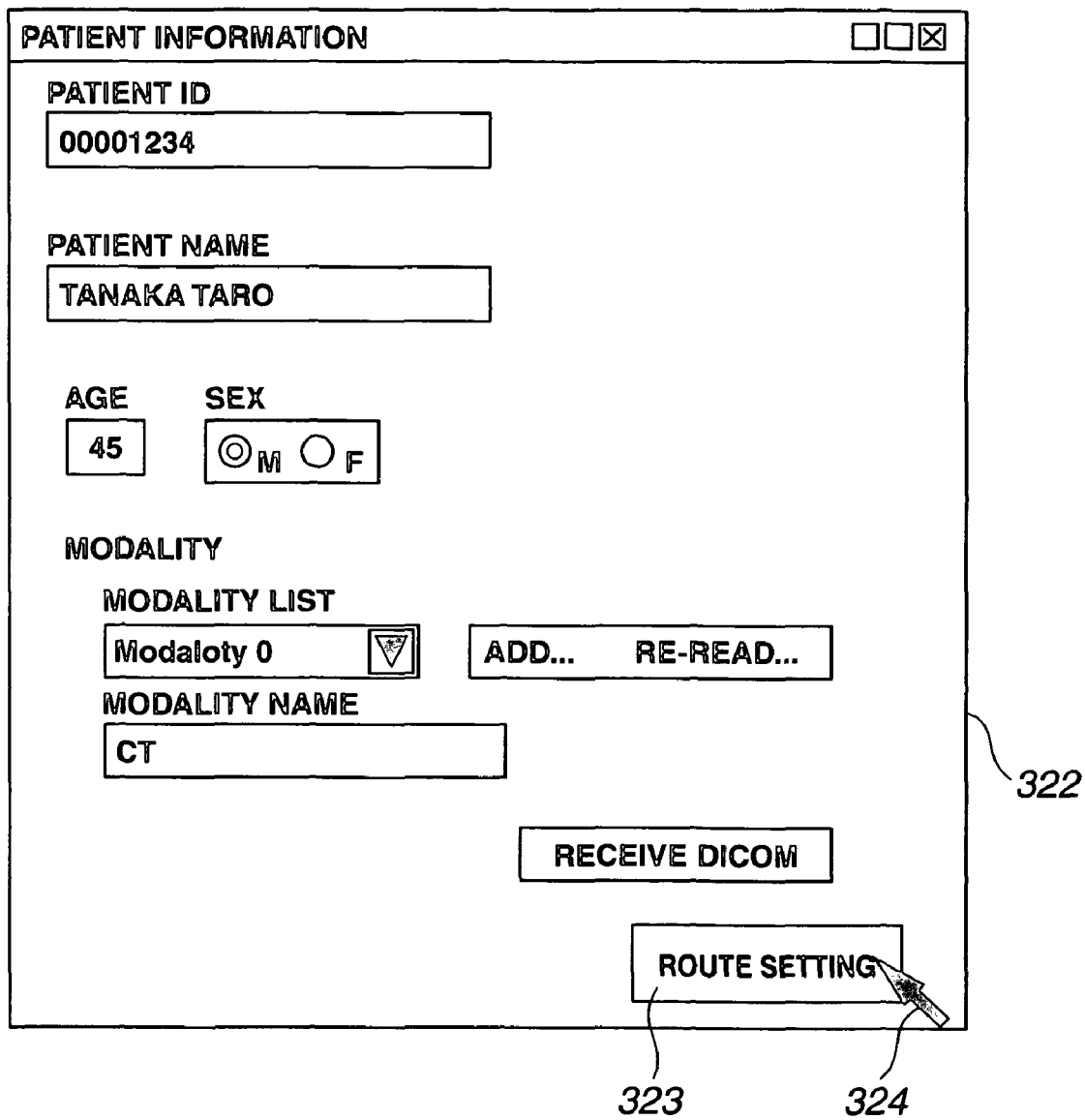
FIG. 21 is a diagram showing a patient information selection screen appearing in the processing of FIG. 20.
Figure 22:
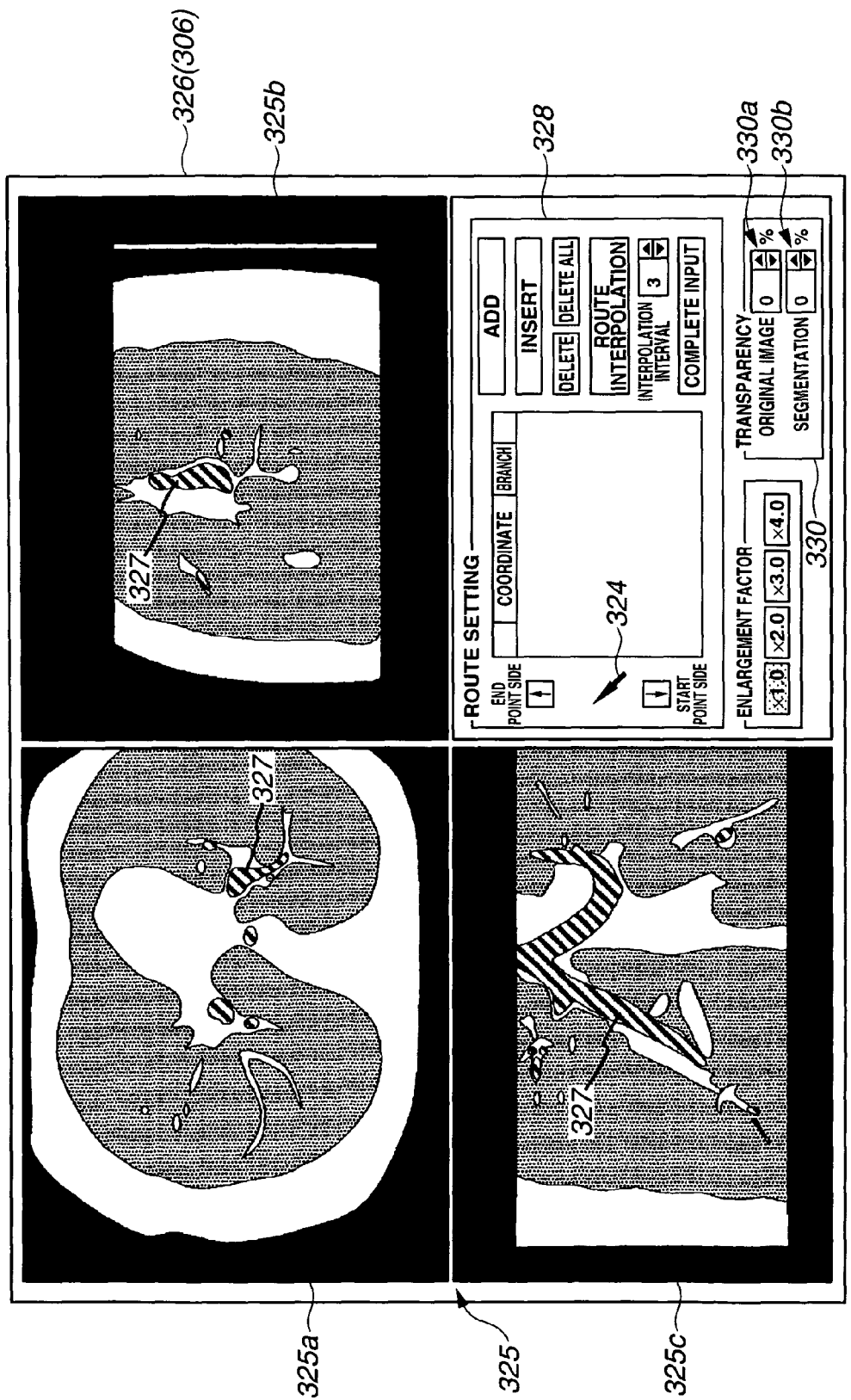
FIG. 22 is a diagram showing a route setting screen appearing in the processing of FIG. 20.

At Step S303, the route setting unit 314 displays a patient information selection screen 322 as shown in FIG. 21 on the monitor 306, and patient information is selected on the patient information selection screen 322. As a route setting button 323 on the patient information selection screen 322 is selected with a pointer 324 through the operation of the input device 319, the MPR image generating unit 313 generates MPR image 325 including, for example, three different multi-planar images of the selected patient at Step S304. Thereby, a route setting screen 326 as shown in FIG. 22 is displayed on the monitor 306. The route setting screen 326 includes an MPR image 325 which includes an axial image 325a, a coronal image 325b, and a sagittal image 325c, and a route information screen 328 which displays route information.

The selection of the patient information by the route setting unit 314 on the patient information selection screen 322 is performed by inputting through the input device 319 a patient ID which identifies one of the patients.

Then, at Step S305, the organ extracting unit 320 extracts the bronchi that is a predetermined organ from the CT image data stored in the CT image data storing unit 312, and bronchi cross-sectional images 327 of the extracted bronchi are generated and output to the MPR image generating unit 313. Then, as illustrated in FIG. 22, the bronchi cross-sectional images 327 of the extracted bronchi are superimposed and displayed on the MPR image 325.

The axial image 325a, the coronal image 325b, and the sagittal image 325c forming the MPR image 325 are monochrome images, for example. Meanwhile, the bronchi cross-sectional images 327 superimposed on the MPR image 325 are blue images (i.e., hatched images in FIG. 22), for example. Thereby, the axial image 325a, the coronal image 325b, and the sagittal image 325c forming the MPR image 325 are displayed to be visually distinguished from the bronchi cross-sectional images 327.

Then, at Step S306, the route setting processing (later described) is performed on a route setting screen 321 to set a route for supporting insertion of the bronchoscope in the bronchi.

When the route for supporting the insertion has been set, successive VBS images of the entirety of the set route are generated in frame units by the VBS image generating unit 315 at Step S307. The generated VBS images are stored in the VBS image storing unit 316 at Step S308.

As the above processings of Steps S301 to S308 are performed, preparation for the insertion support performed by the insertion support apparatus 305 in the observation and treatment using the bronchoscope is completed.

With reference to FIGS. 22 to 26, a characteristic of a method of displaying the MPR image 325 and the bronchi cross-sectional images 327 superimposed thereon will now be described.

On the route setting screen 326 shown in FIG. 22, a transparency setting box 330 on the route information area 328 is operated with the pointer 324 by using the input device 319. Thereby, the transparency on the monitor 306 can be set for each of the MPR image 325 and the bronchi cross-sectional images 327 which are extracted luminal organ images superimposed on the MPR image 325. FIG. 22 illustrates an example display of the MPR image 325 and the bronchi cross-sectional images 327, in which the transparency is set to be 0% for both of the MPR image 325 and the bronchi cross-sectional images 327.

Specifically, the transparency setting box 330 includes an MPR image transparency adjusting button 330a and an extracted luminal organ image transparency adjusting button 330b. As the MPR image transparency adjusting button 330a and the extracted luminal organ image transparency adjusting button 330b are operated with the pointer 324 by using the input device 319, the transparency of the MPR image 325 and the bronchi cross-sectional images 327 can be increased or decreased.

Figure 23:
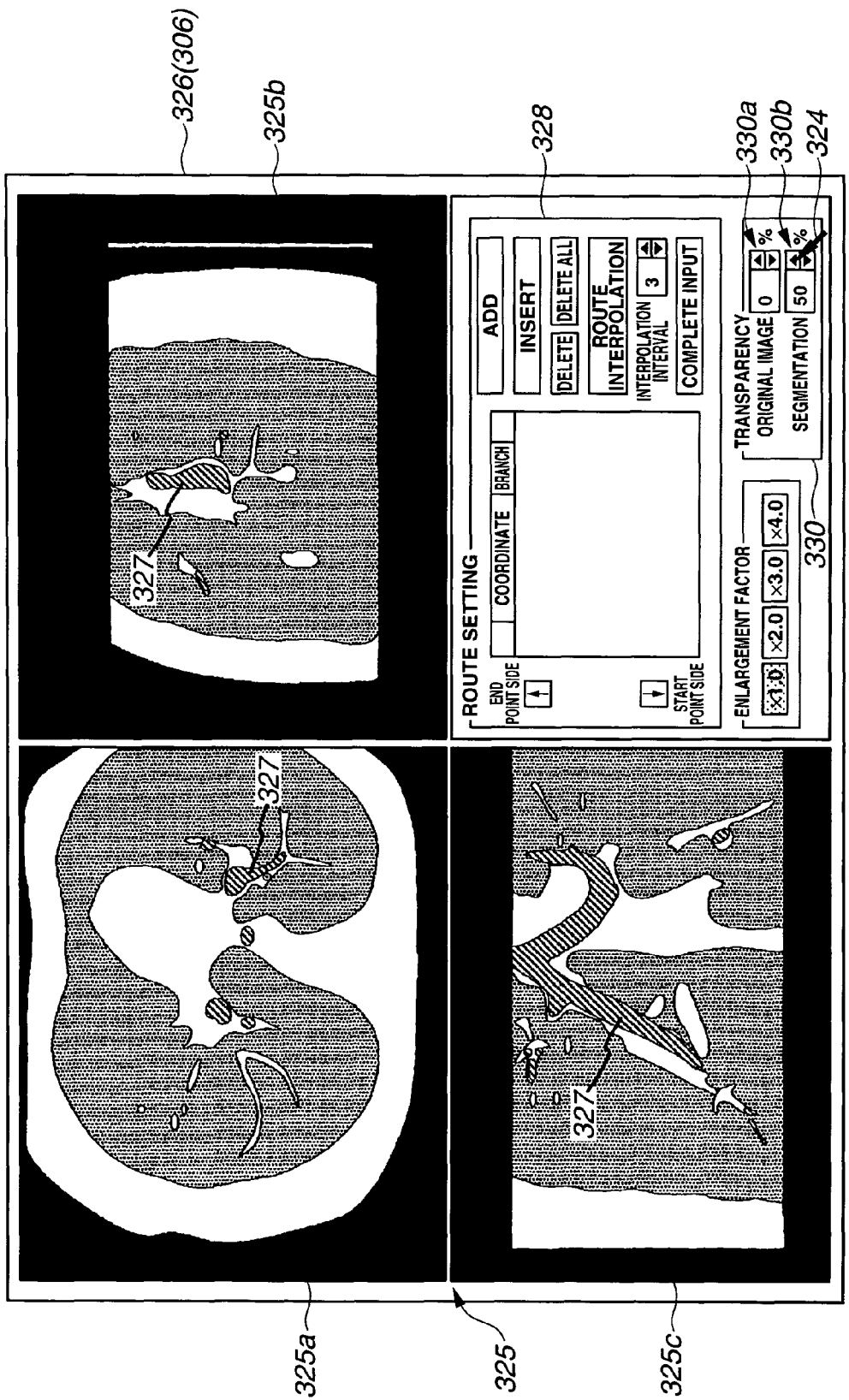
FIG. 23 is a first diagram illustrating a characteristic of a method of displaying the bronchi cross-sectional images and the MPR image of FIG. 22.
Figure 24:
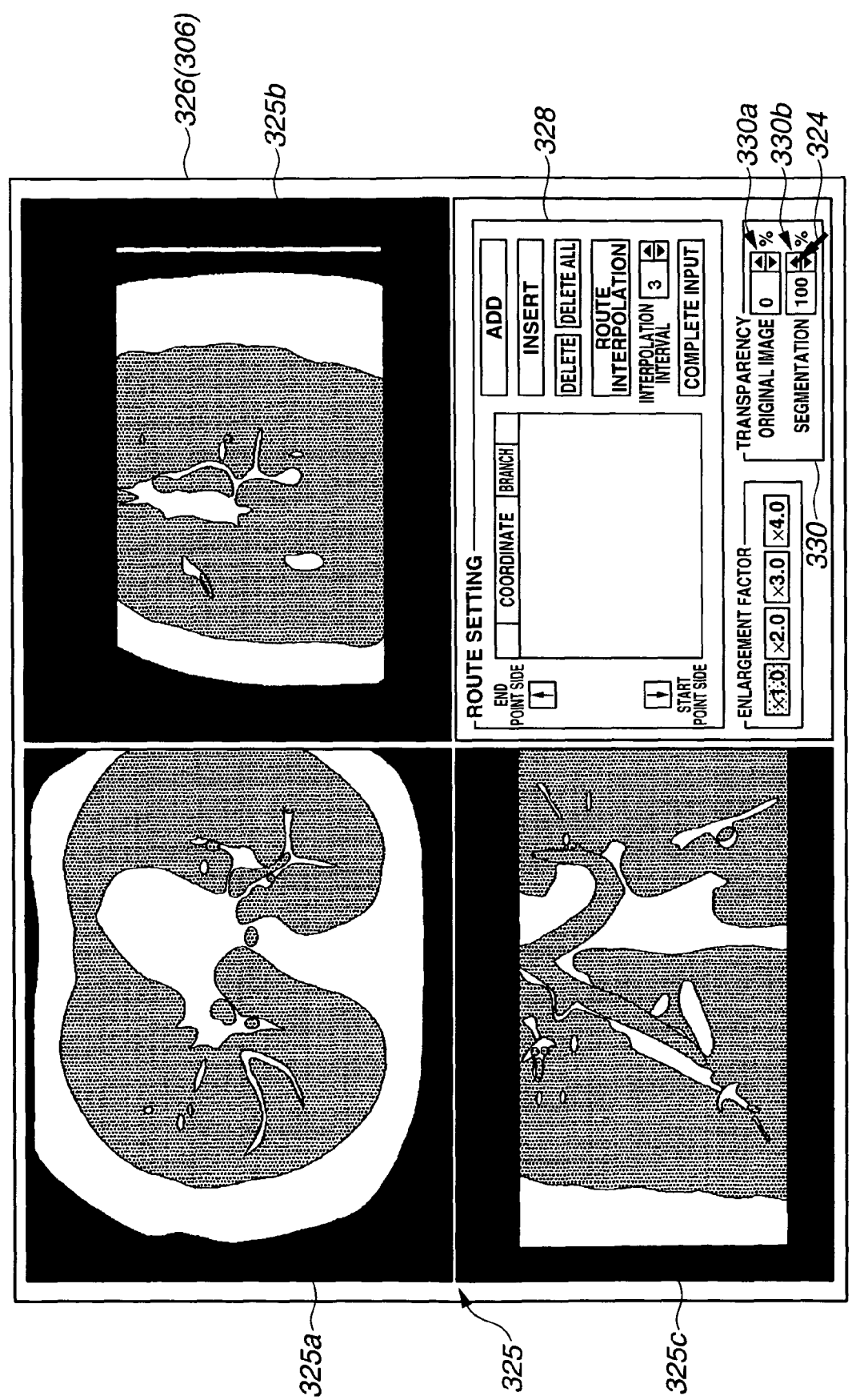
FIG. 24 is a second diagram illustrating the characteristic of the method of displaying the bronchi cross-sectional images and the MPR image of FIG. 22.

FIG. 23 illustrates an example display in which the transparency of the MPR image 325 is set to be 0% and the transparency of the bronchi cross-sectional images 327 is set to be 50%. FIG. 24 illustrates an example display in which the transparency of the MPR image 325 is set to be 0% and the transparency of the bronchi cross-sectional images 327 is set to be 100%. As illustrated in FIGS. 22 to 24, enhanced display of the bronchi cross-sectional images 327 against the MPR image 325 (FIGS. 22 and 23) and assimilation display of assimilating the bronchi cross-sectional images 327 into the MPR image 325 (FIG. 24) can be performed by changing the transparency of the bronchi cross-sectional images 327.

Figure 25:
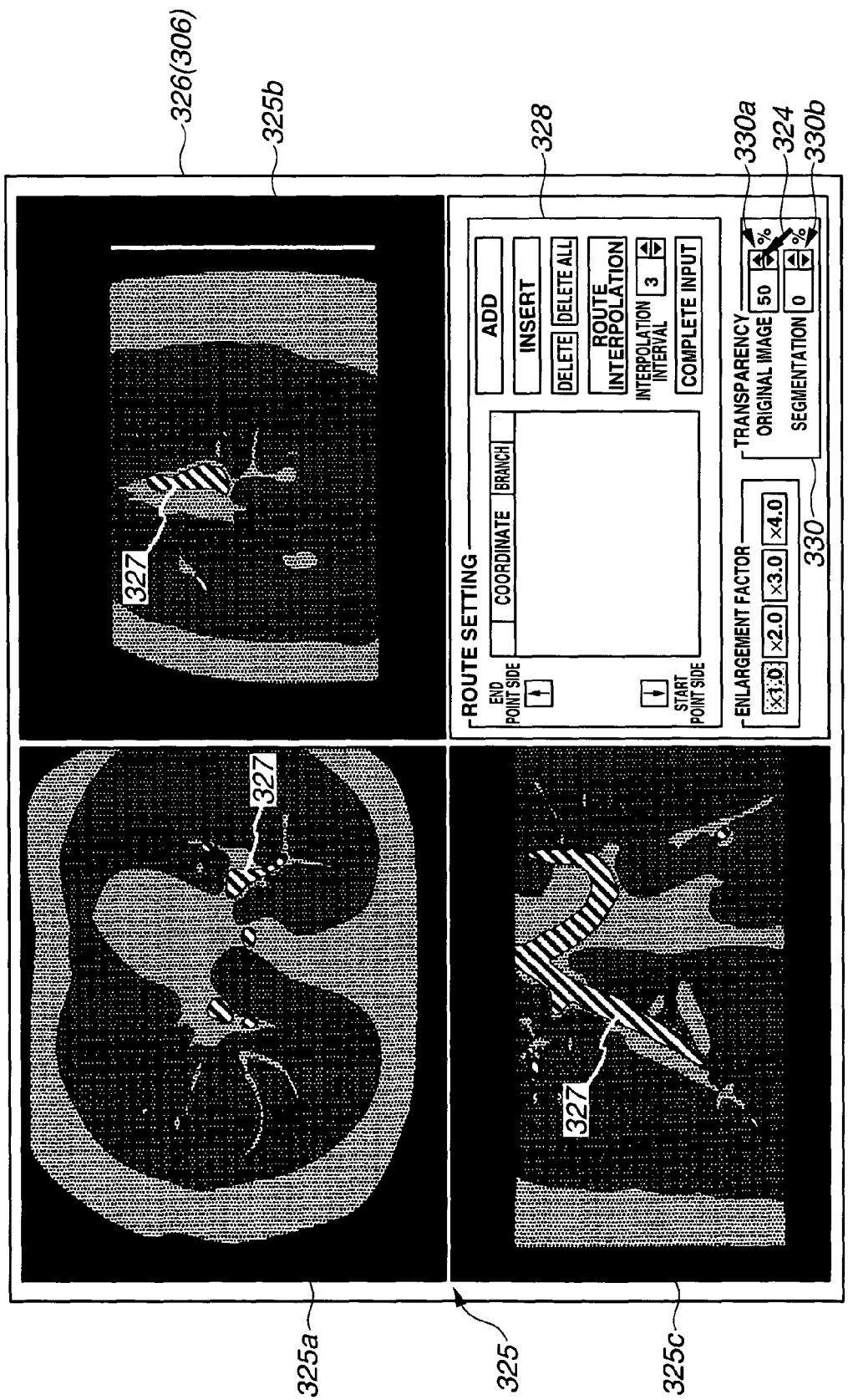
FIG. 25 is a third diagram illustrating the characteristic of the method of displaying the bronchi cross-sectional images and the MPR image of FIG. 22.
Figure 26:
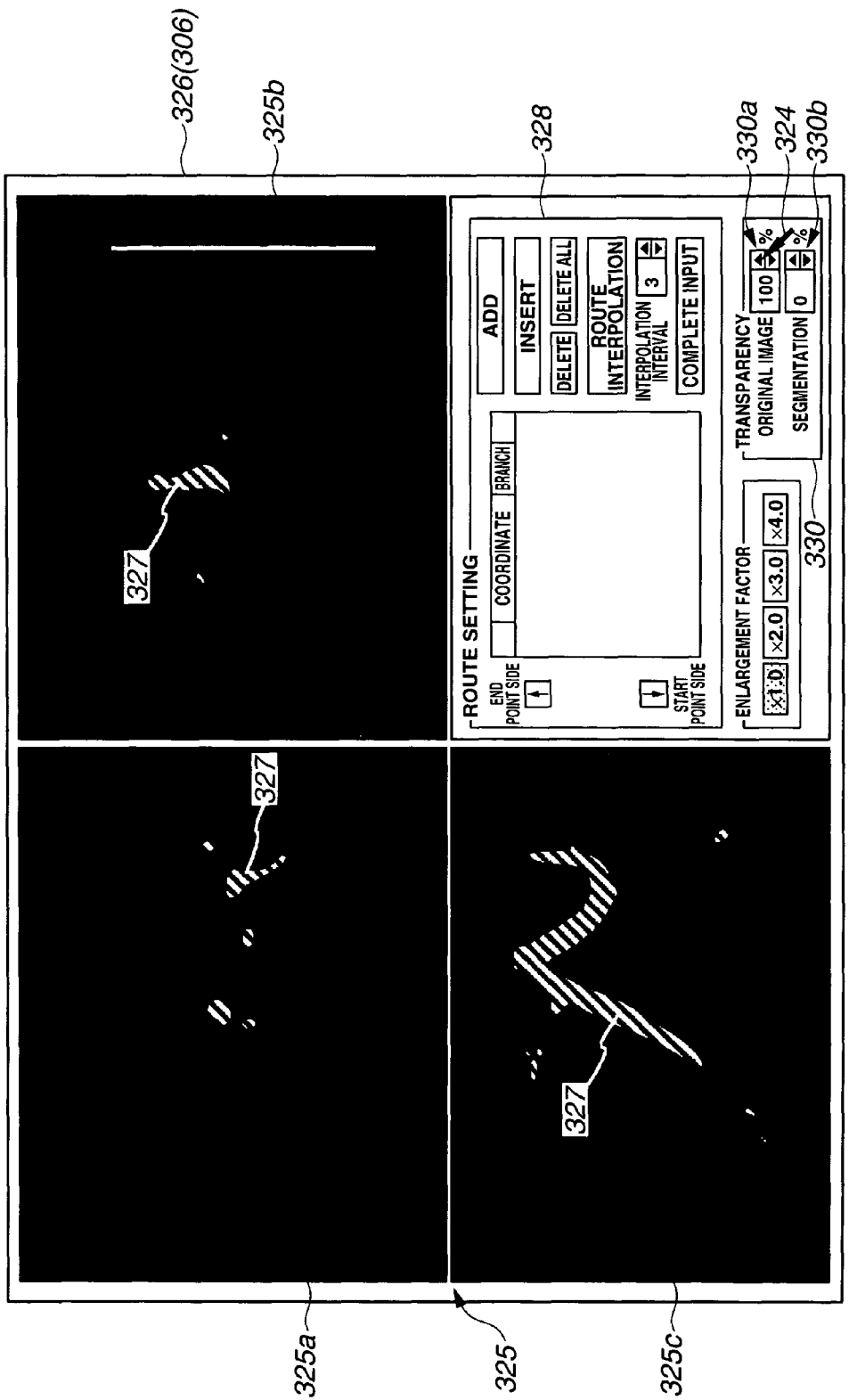
FIG. 26 is a fourth diagram illustrating the characteristic of the method of displaying the bronchi cross-sectional images and the MPR image of FIG. 22.

FIG. 25 illustrates an example display in which the transparency of the MPR image 325 is set to be 50% and the transparency of the bronchi cross-sectional images 327 is set to be 0%. FIG. 26 illustrates an example display in which the transparency of the MPR image 325 is set to be 100% and the transparency of the bronchi cross-sectional images 327 is set to be 0%. As illustrated in FIGS. 22, 25, and 26, the enhanced display of the bronchi cross-sectional images 327 against the MPR image 325 (FIGS. 22 and 25) and bronchi isolation display of only displaying the bronchi cross-sectional images 327 (FIG. 26) can be performed by changing the transparency of the MPR image 325.

As described above, as the MPR image transparency adjusting button 330a and the extracted luminal organ image transparency adjusting button 330b are operated, the transparency of the MPR image 325 and the bronchi cross-sectional images 327 can be arbitrarily increased or decreased. Further, since the bronchi cross-sectional images 327 obtained by the luminal organ extraction of the bronchi on the basis of the CT image data are superimposed and displayed on the MPR image 325 with a desired enhancement degree, a surgeon can check the location of the bronchi on the MPR image 325 while observing the ordinary MPR image 325.

Needless to say, the above is not limited to the case of the bronchi but can apply to a case in which the location of another luminal organ, such as an intestinal tract and a biliary tract, for example, is checked with the MPR image 325.

The route setting processing of Step S306 performed by the route setting unit 314 will now be described with reference to FIGS. 27 to 37.

Figure 27:
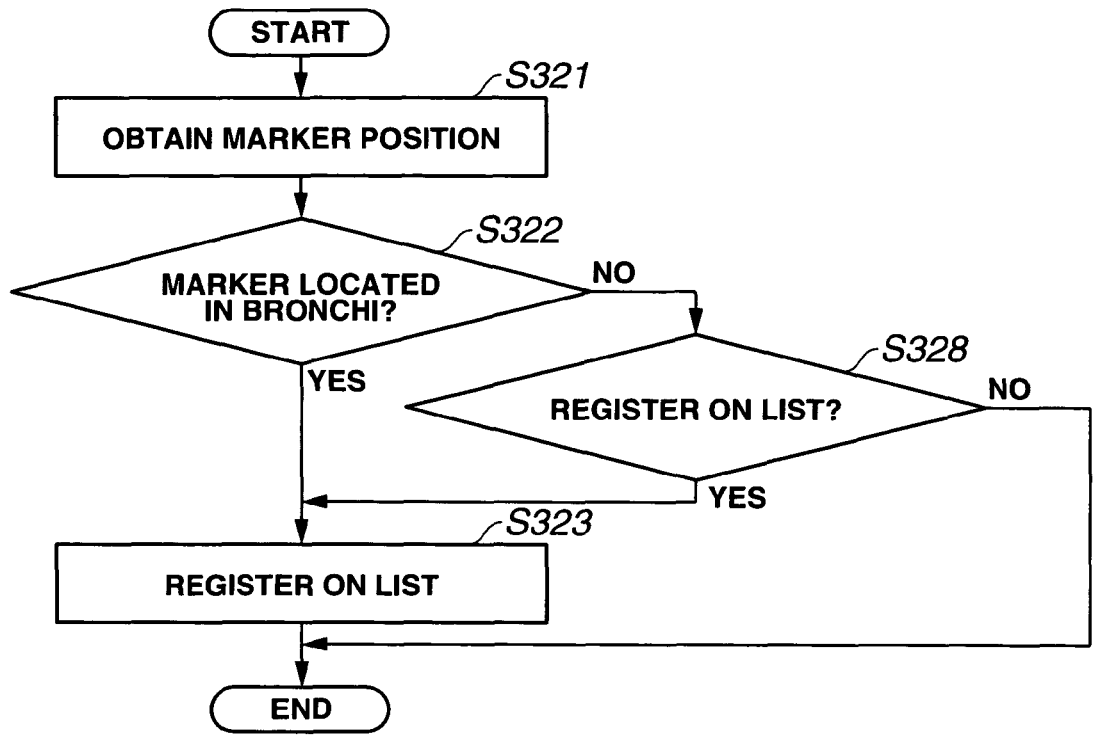
FIG. 27 is a first flowchart illustrating a flow of the route setting processing of FIG. 20.
Figure 29:
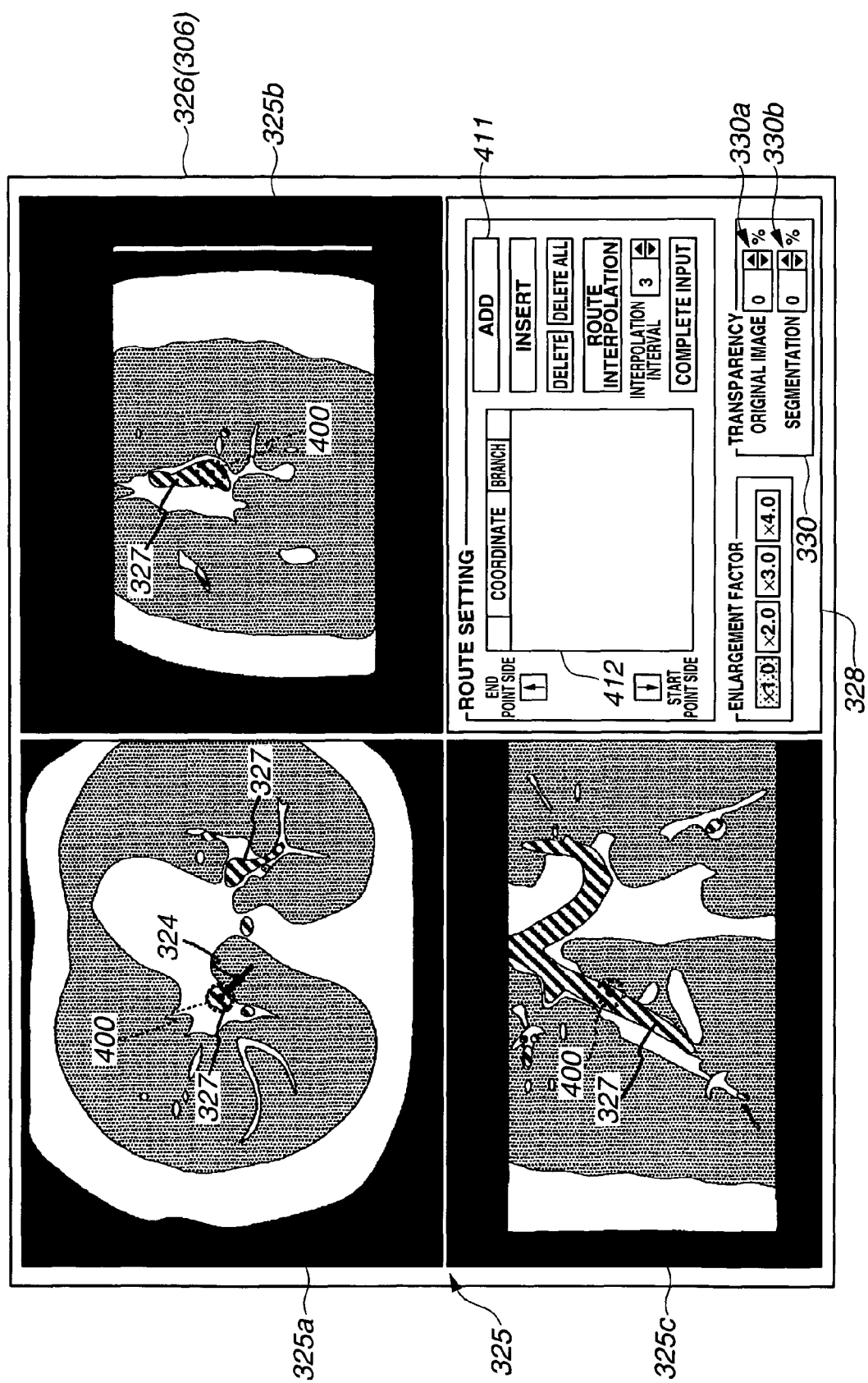
FIG. 29 is a first diagram illustrating the processings of FIGS. 27 and 28.

As illustrated in FIG. 27, a marker indicating the position of the end point of the insertion support into the bronchi is obtained on the MPR image at Step S321. Specifically, as illustrated in FIG. 29, when a position on the axial image 325a of the MPR image 325, for example, is clicked with the pointer 324, a marker 400 is displayed at the position at which the clicking has been performed. At the same time, the marker 400 is also displayed at a corresponding position in each of the coronal image 325b and the sagittal image 325c.

When an add button 411 on the route information area 328 is selected with the pointer 324, the route setting unit 314 obtains a three-dimensional coordinate of the marker 400 specified on the axial screen 325a, the coronal image 325b, and the sagittal image 325c.

Figure 30:
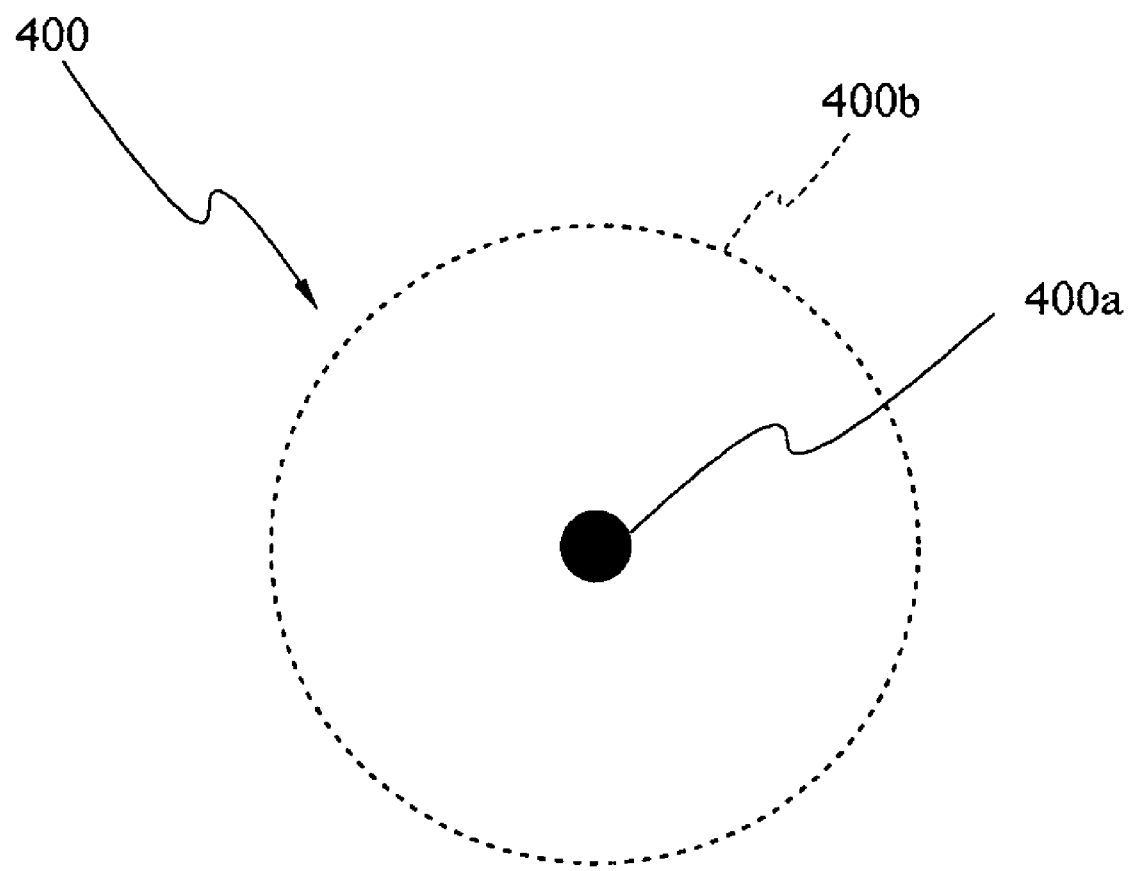
FIG. 30 is a second diagram illustrating the processings of FIGS. 27 and 28.

As illustrated in FIG. 30, the marker 400 includes a mark point 400a which indicates the point at which the clicking has been performed by the pointer 324, and a region line 400b which indicates a predetermined region including the mark point 400a such that the mark point 400a can be visually recognized on the MPR image 325. Therefore, the surgeon can easily check the position of the marker 400 by visually recognizing the region line 400b on the MPR image 325.

Figure 37:
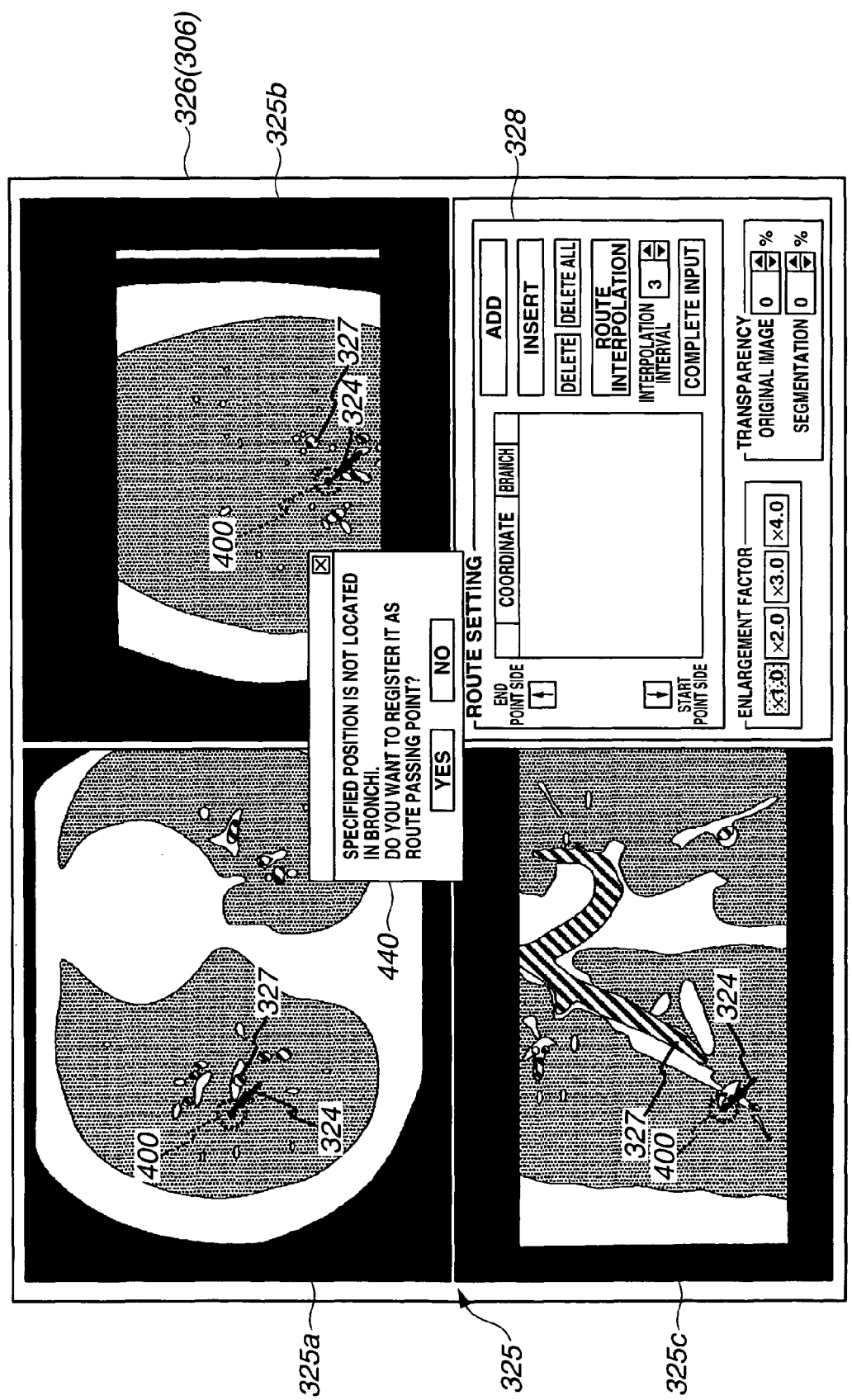
FIG. 37 is a ninth diagram illustrating the processings of FIGS. 27 and 28.

Then, at Step S322, it is determined whether the marker 400 is located within the bronchi. If it is determined that the marker 400 is located within the bronchi, a mark point is registered on a passing point list at Step S323. If it is determined that the marker 400 is not located within the bronchi, a confirmation window 440 as shown in FIG. 37 is displayed at Step S328. If the surgeon has specified the mark point outside the bronchi and selects "YES," the mark point is registered on the passing point list. The three-dimensional coordinate of the marker 400 registered on the passing point list is displayed with a number in a registered information area 412 (refer to FIGS. 29 and 32) on the route information area 328.

Figure 31:
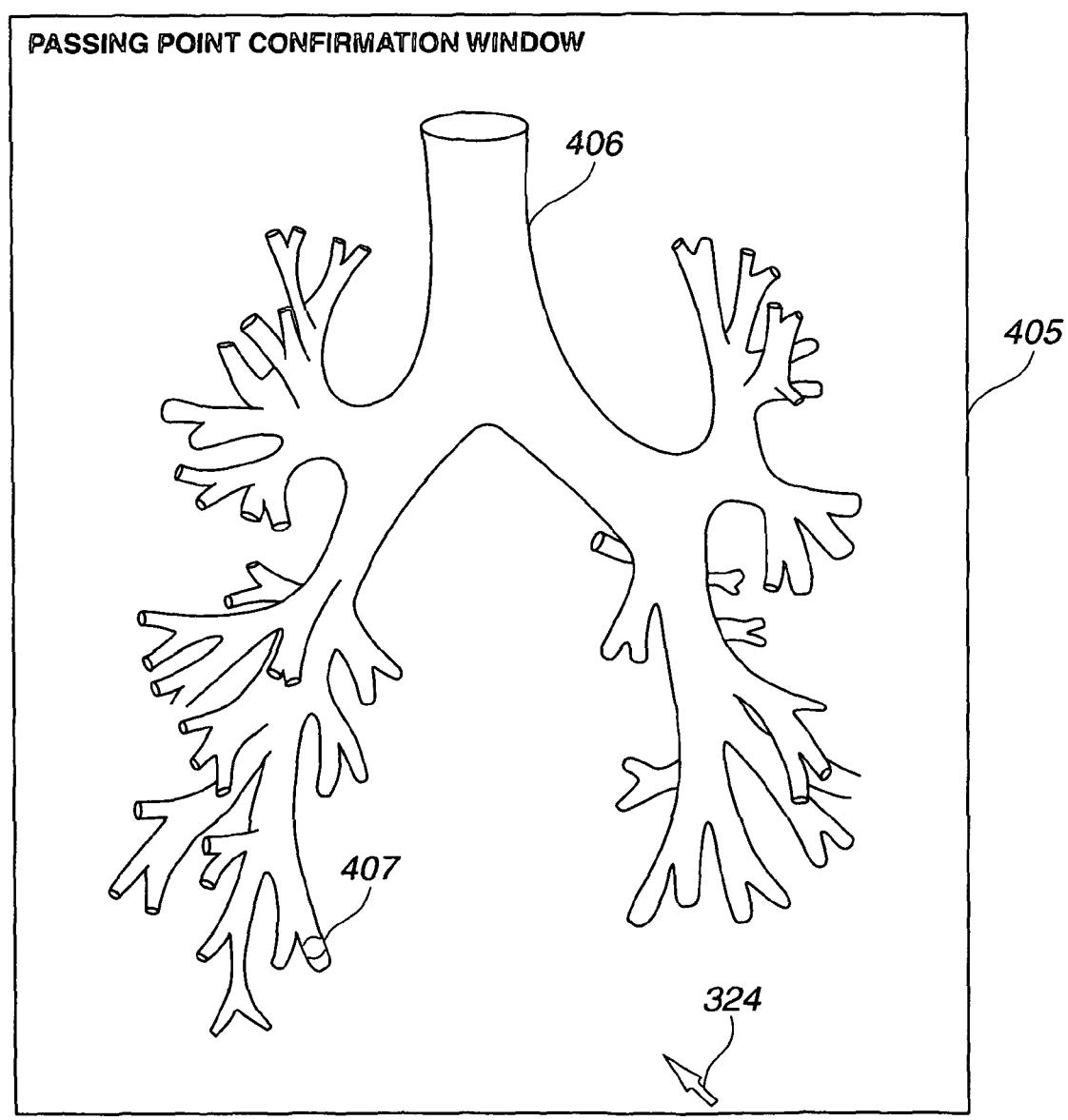
FIG. 31 is a third diagram illustrating the processings of FIGS. 27 and 28.

Further, a passing point confirmation window 405 as shown in FIG. 31 may be displayed. The passing point confirmation window 405 is a window used for confirming the marker 400 on a bronchi image 406 which is displayed three-dimensionally. With the passing point confirmation window 405, the surgeon determines whether the marker 400 has been placed at a predetermined position within the bronchi.

Then, a process of registering the marker 400 on the passing point list is repeated for each of passing points leading to a desired position.

Figure 32:
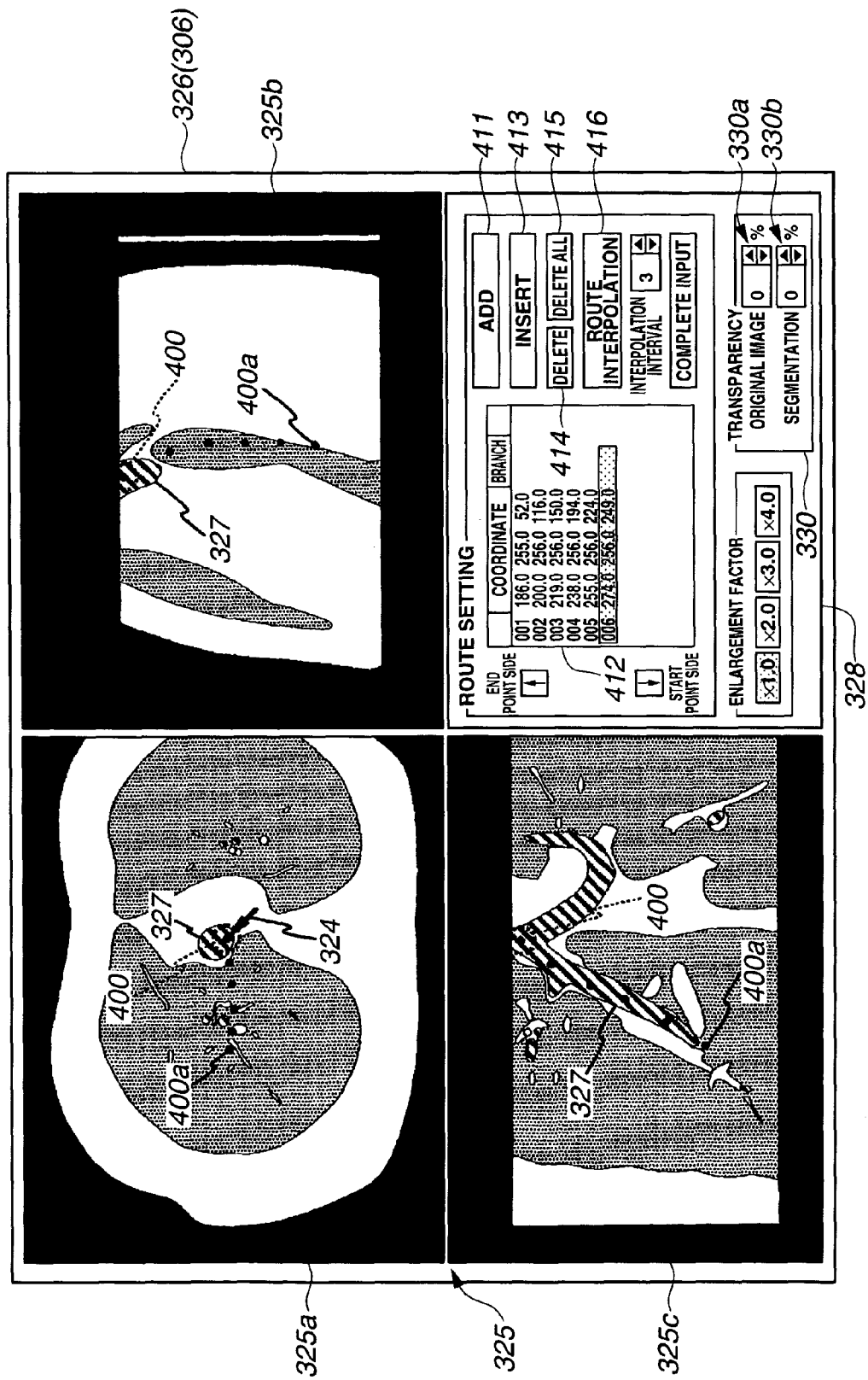
FIG. 32 is a fourth diagram illustrating the processings of FIGS. 27 and 28.
Figure 33:
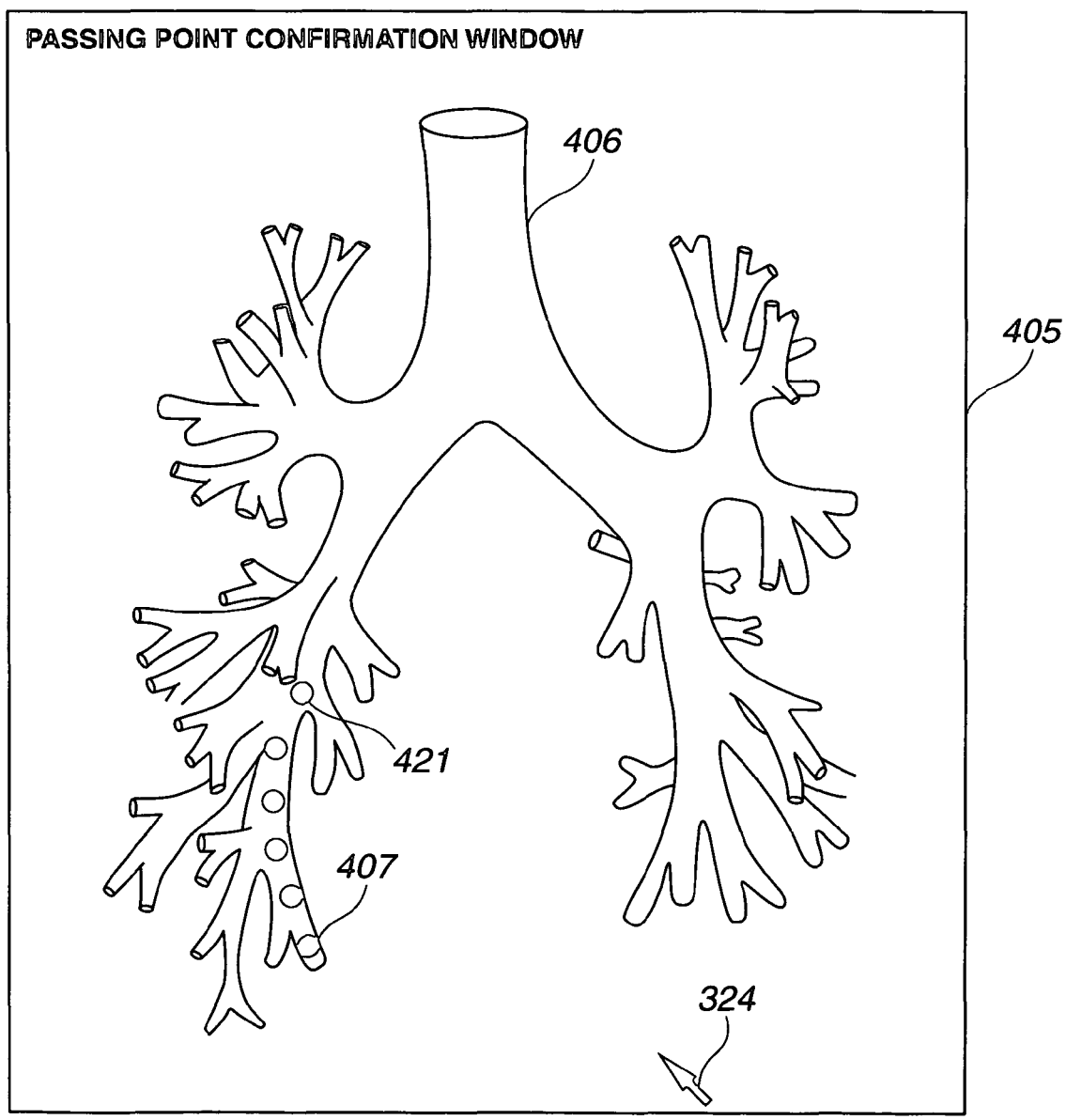
FIG. 33 is a fifth diagram illustrating the processings of FIGS. 27 and 28.

FIG. 32 illustrates a state in which a sixth passing point is newly specified by the marker 400 after five passing points have been registered. As illustrated on the MPR image 325 shown in FIG. 32, the already registered five passing points 400a are displayed as green points, for example. Further, in the passing point confirmation window 405, the already registered five passing points 400a are displayed as green points, while the sixth passing point 421 is displayed as a red point, for example.

Figure 34:
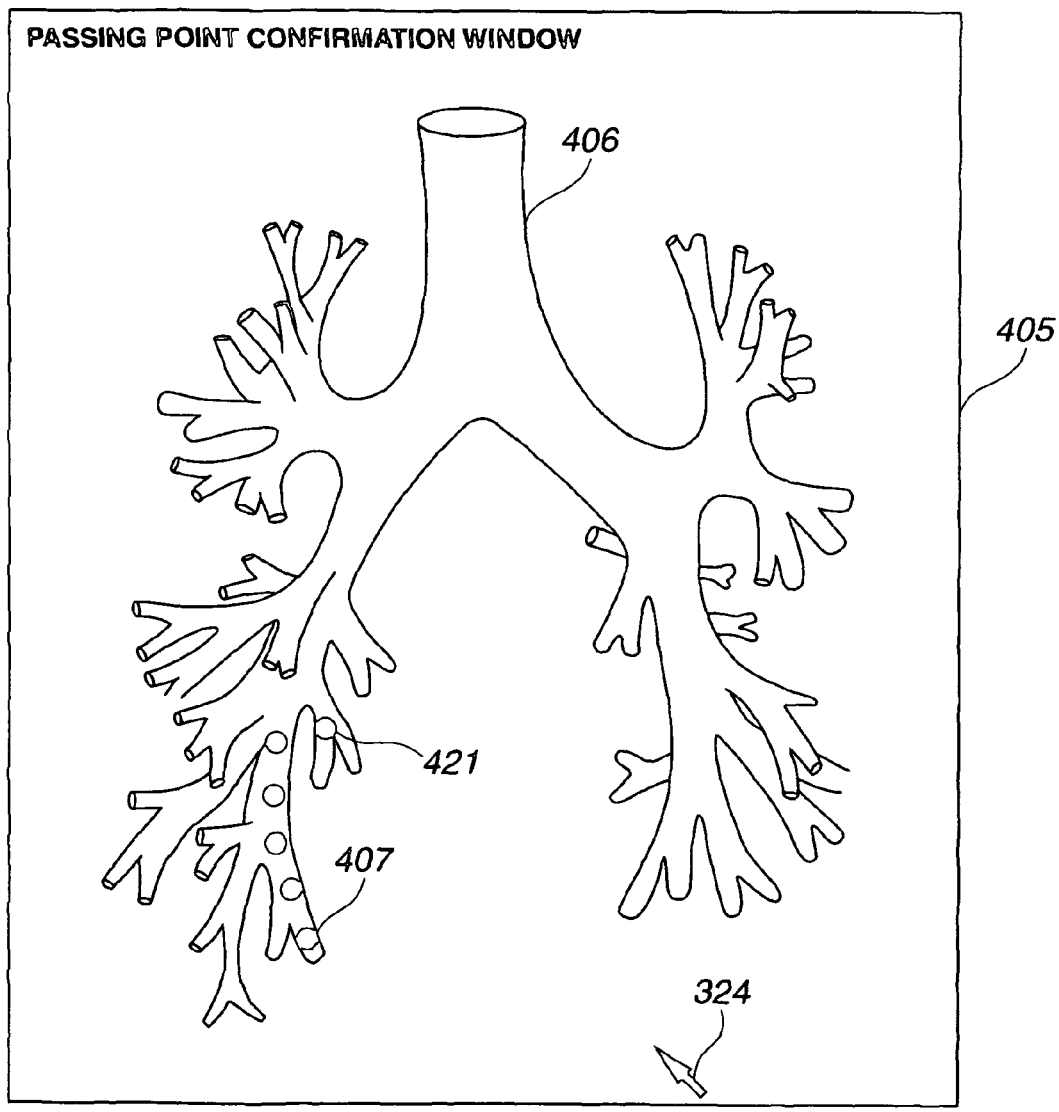
FIG. 34 is a sixth diagram illustrating the processings of FIGS. 27 and 28.

For example, in specifying the sixth passing point with the marker 400 on the MPR image 325 shown in FIG. 32, if it is determined with the passing point confirmation window 405 shown in FIG. 34 that a current passing point 421 has been marked at a position within the bronchi not suitable for the insertion support with respect to the previously specified passing point on the bronchi image 406, the specification of the marker 400 can be cancelled by selecting a delete button 414 on the route information area 328 shown in FIG. 32 with the pointer 324. If a delete-all button 415 is selected, all of the passing points including the current passing point 421 are deleted.

Figure 35:
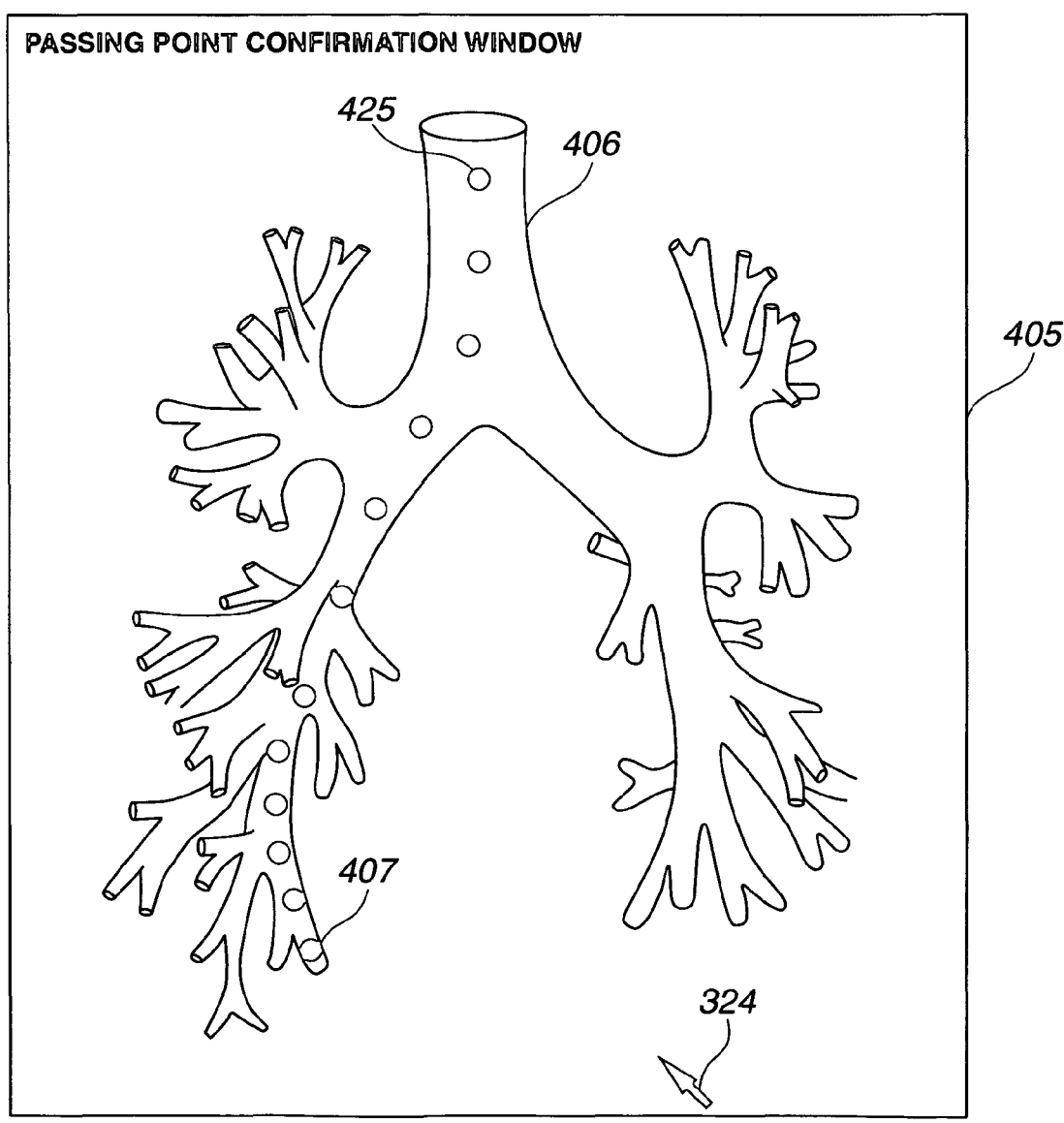
FIG. 35 is a seventh diagram illustrating the processings of FIGS. 27 and 28.
Figure 36:
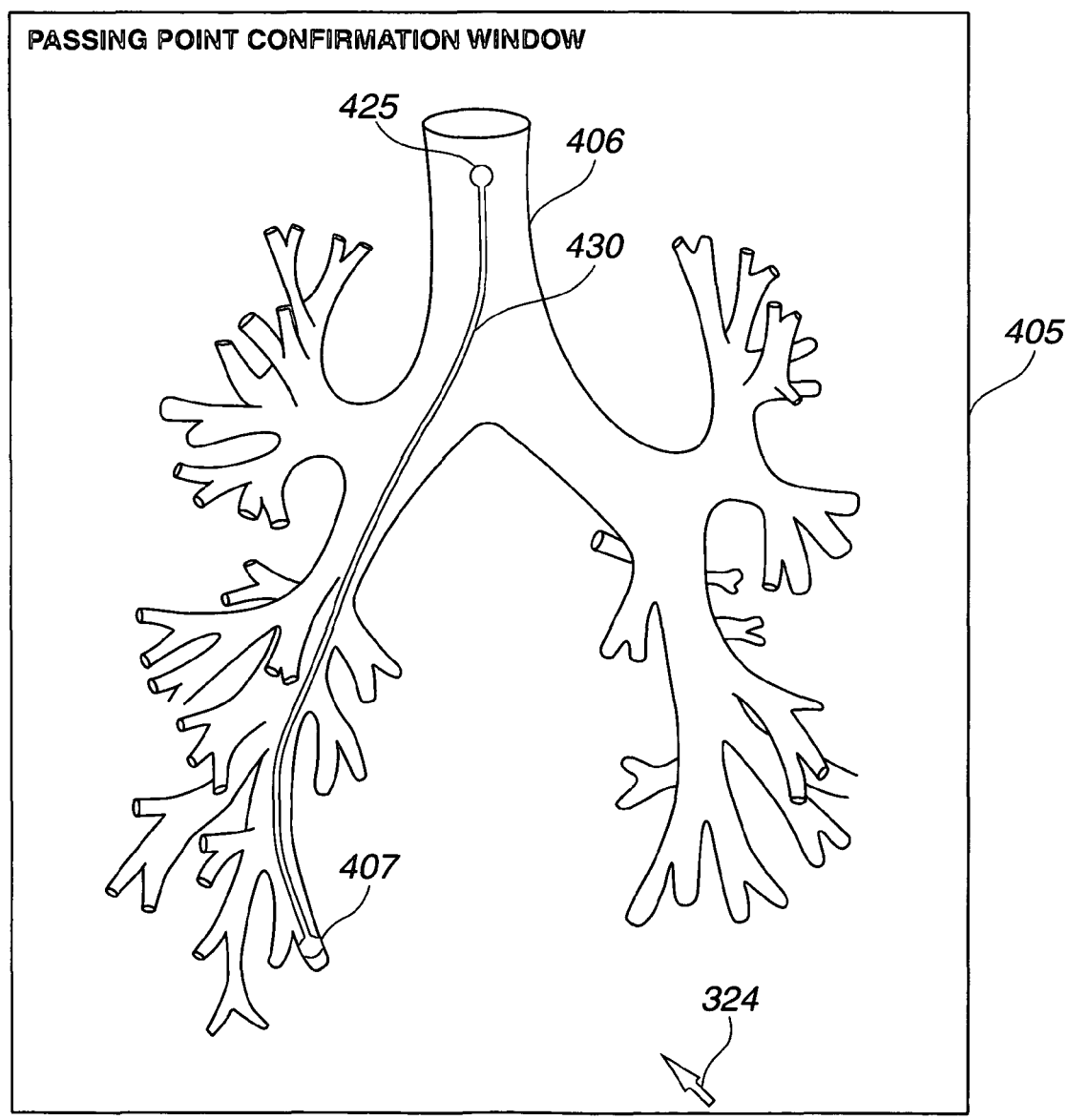
FIG. 36 is an eighth diagram illustrating the processings of FIGS. 27 and 28.

As illustrated in the passing point confirmation window 405 of FIG. 35, after the desired passing points connecting the end point 407 and the desired start point 425 at which the insertion support is started have been thus registered on the passing point list, the surgeon determines whether interpolation of the passing points needs to be performed.

Figure 28:
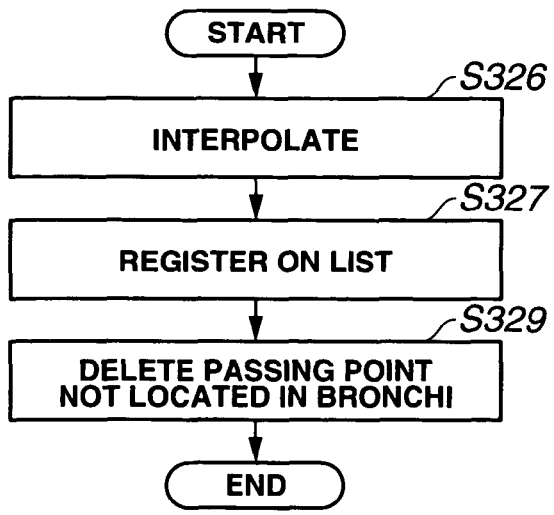
FIG. 28 is a second flowchart illustrating the flow of the route setting processing of FIG. 20.

If a route interpolation button 416 is selected, a predetermined interpolation processing (e.g., linear interpolation between the passing points) is performed at Step S326 of FIG. 28.

This interpolation processing is performed by interpolating a plurality of virtual points at predetermined intervals between the passing points in the bronchi. The interpolation interval of the virtual points can be arbitrarily set with an interpolation interval box on the route information area 328.

Then, a route 430 formed by the passing points including the virtual points is registered on the passing point list at Step S327.

However, the passing points registered at Step S327 are not necessarily located within the bronchi. If the interpolation processing has been performed outside the bronchi, the passing point not located within the bronchi is deleted from the passing point list at Step S329 after the processing of Step S327 has been performed. Then, the interpolation processing is completed, and the route 430 is displayed on the passing point confirmation window 405 shown in FIG. 36.

After the route 430 has been thus set by the route setting unit 314, the flow moves to the processing of Step S307 of FIG. 20. As described above, the VBS image generating unit 315 generates the successive VBS images in frame units along the set route 430 at Step S307, and the thus generated VBS images are stored in the VBS image storing unit 316 at Step S308.

Description will now be made of an insertion support screen used in the insertion support performed, during the observation and the treatment, by the insertion support apparatus 305 and the bronchoscope device 303 for which the route has been set as described above. To simplify explanation, the following description will be made of a case in which the route has ten branch points, as one example.

Figure 38:
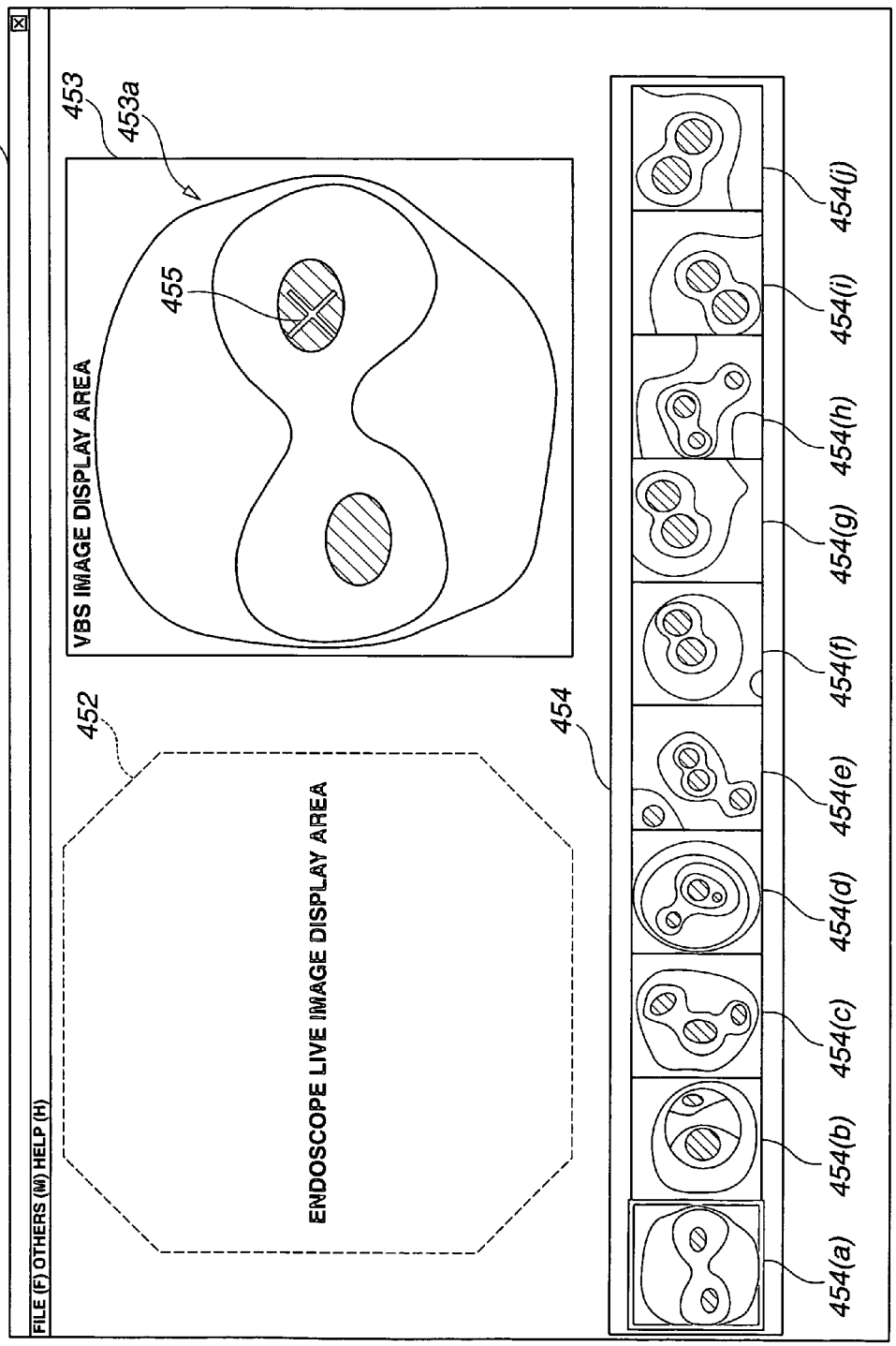
FIG. 38 is a diagram showing an insertion support screen generated by the insertion support apparatus of FIG. 19.

When the bronchoscopic examination is started under the insertion support by the insertion support apparatus 305, an insertion support screen 451 shown in FIG. 38 is displayed on the monitor 306.

The insertion support screen 451 includes an endoscope live image display area 452 for displaying a live image sent by the bronchoscope device 303, a VBS image display area 453 for displaying a VBS image 453a, and a branch thumbnail VBS image area 454 for displaying branch thumbnail VBS images 454(a) to 454(j) which are reduced size images of the VBS image 453a at all of the branch points along the route. The VBS image 453a of the first branch point of the route is displayed in the VBS image display area 453, and the branch thumbnail VBS images 454(a) to 454(j) of all of the branch points are displayed in the branch thumbnail VBS image area 454.

A navigation maker 455 is displayed on the VBS image 453a such that the navigation maker 455 is superimposed on a route hole leading into the route. Further, one of the branch thumbnail VBS images similar to the VBS image 453a displayed in the VBS image display area 453 is framed in color or by a bold line to be distinguished from the other branch thumbnail VBS images. Accordingly, the surgeon can easily recognize which one of the branch images corresponds to the VBS image displayed in the VBS image display area 453. In an initial stage, the branch thumbnail VBS image 454(a) is framed in color or by a bold line.

Embodiment 3

Figure 39:
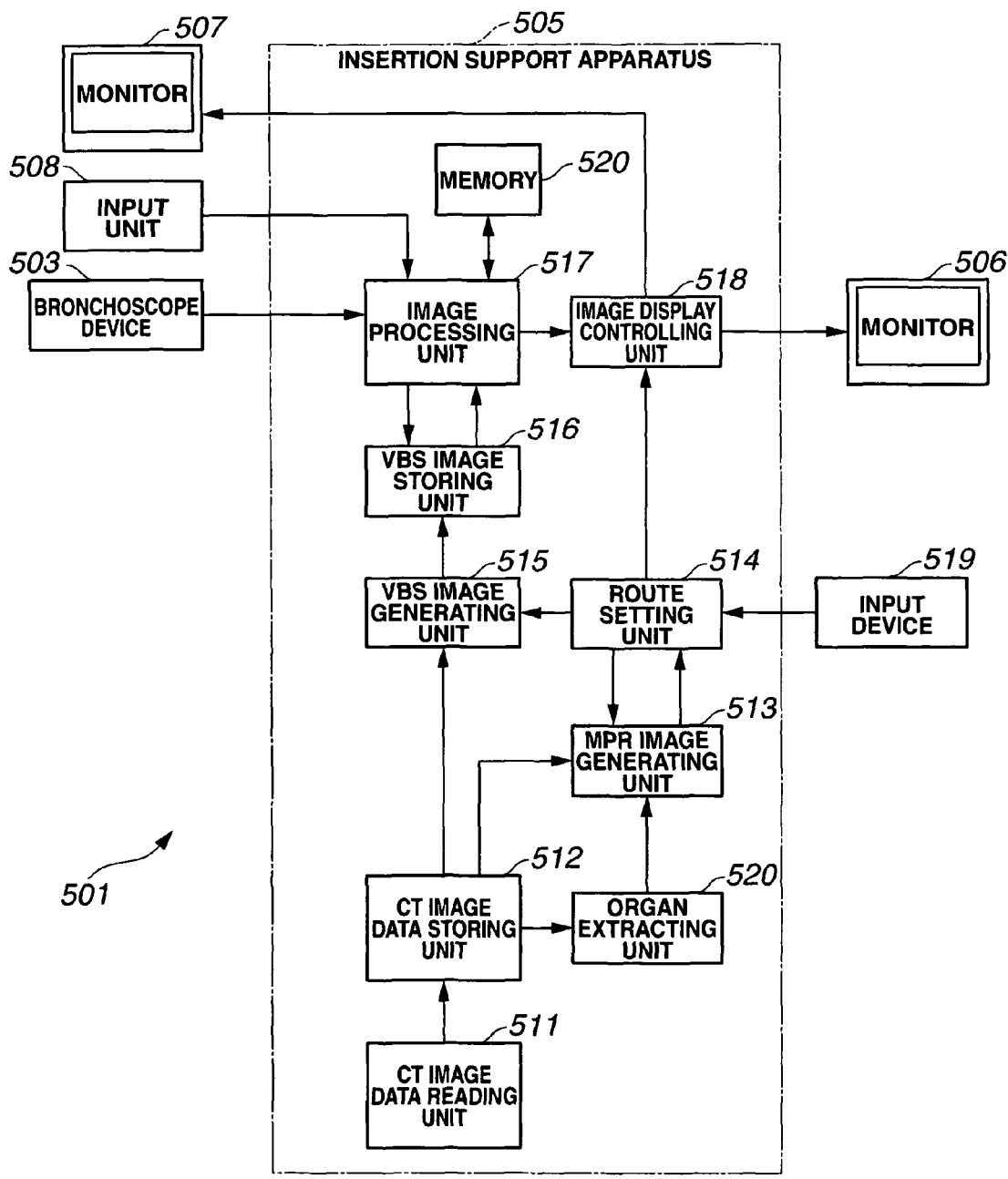
FIG. 39 is a configuration diagram illustrating a configuration of a bronchi insertion support system according to Embodiment 3 of the present invention.

As illustrated in FIG. 39, a bronchi insertion support system 501 according to the present Embodiment 3 includes a bronchoscope device 503 and an insertion support apparatus 505.

The insertion support apparatus 505 supports insertion of the bronchoscope device 503 into the bronchi by generating a virtual endoscope image (hereinafter referred to as a VBS image) of the interior of the bronchi on the basis of CT image data, combining the VBS image with an endoscope image (hereinafter referred to as a live image) obtained by the bronchoscope device 503, and displaying a resultant image on a monitor 506.

The bronchoscope device 503 includes a bronchoscope having image picking-up means, a light source for supplying illuminating light to the bronchoscope, a camera controlling unit for performing signal processing on an image pickup signal sent by the bronchoscope, and the like, which are not illustrated in the figure. The bronchoscope device 503 inserts the bronchoscope into the bronchi of a patient, captures images of the interior of the bronchi, performs a biopsy to examine target tissue located at a periphery of the bronchi, combines the live image with the VBS image, and displays a resultant image on a monitor 507.

The monitor 507 includes an input unit 508 having a touch screen so that a user can easily operate the input unit 508 including the touch screen while performing an insertion procedure.

The insertion support apparatus 505 includes a CT image data reading unit 511 which reads three-dimensional image data generated by a known CT apparatus (not illustrated) that captures X-ray cross-sectional images of a patient, through a portable data storage medium, such as an MO (Magnetic Optical disk) device, a DVD (Digital Versatile Disk) device, or the like, for example; and a CT image data storing unit 512 which stores the CT image data read by the CT image data reading unit 511. The insertion support apparatus 505 further includes an organ extracting unit 520 which extracts segmentation, i.e., three-dimensional information of the bronchi that is a predetermined organ from the CT image data stored in the CT image data storing unit 512; and an MPR image generating unit 513 which generates an MPR image (a multi-planar reformatted image) on the basis of the CT image data stored in the CT image data storing unit 512 and which displays a bronchi cross-sectional image of the bronchi extracted by the organ extracting unit 520 by superimposing the bronchi cross-sectional image on the MPR image. The insertion support apparatus 505 further includes a route setting unit 514 which generates a route setting screen (later described) including the MPR image generated by the MPR image generating unit 513 and which sets a support route (hereinafter simply referred to as a route) for guiding the bronchoscope device 503 to the bronchi. The insertion support apparatus 505 further includes a VBS image generating unit 515 which generates successive VBS images of the route set by the route setting unit 514 in frame units on the basis of the CT image data stored in the CT image data storing unit 512; and a VBS image storing unit 516 which stores the VBS images generated by the VBS image generating unit 515. The insertion support apparatus 505 further includes an image processing unit 517 which receives inputs of the image pickup signal sent by the bronchoscope device 503 and an input signal sent by the input unit 508 and which generates an insertion support screen (later described) including the live image, the VBS image, and a plurality of thumbnail VBS images; and an image display controlling unit 518 which displays, on the monitor 506, the route setting screen generated by the route setting unit 514 and the insertion support screen generated by the image processing unit 517. The insertion support apparatus 505 further includes an input device 519 which includes a keyboard and a pointing device for inputting set information in the route setting unit 514.

The bronchoscope device 503 receives the VBS image and the thumbnail VBS images from the image processing unit 517 of the insertion support apparatus 505, combines the received VBS image and thumbnail VBS images with the live image, and displays a resultant image on the monitor 507.

Further, the bronchoscope device 503 outputs input information sent by the input unit 508 which includes the touch screen of the monitor 507, to the image processing unit 517 of the insertion support apparatus 5.

The CT image data storing unit 512 and the VBS image storing unit 516 may be formed by one hard disk. Further, the MPR image generating unit 513, the route setting unit 514, the VBS image generating unit 515, and the image processing unit 517 may be formed by one arithmetic processing circuit. The CT image data reading unit 511 described above reads the CT image data through the portable data storage medium, such as the MO, the DVD, or the like. If a CT apparatus or an in-house server which stores the CT image data is connected to an in-house LAN, the CT image data reading unit 511 may be formed by an interface circuit connectable to the in-house LAN so that the CT image data is read through the in-house LAN.

Operations according to the thus configured present embodiment will now be described.

Figure 40:
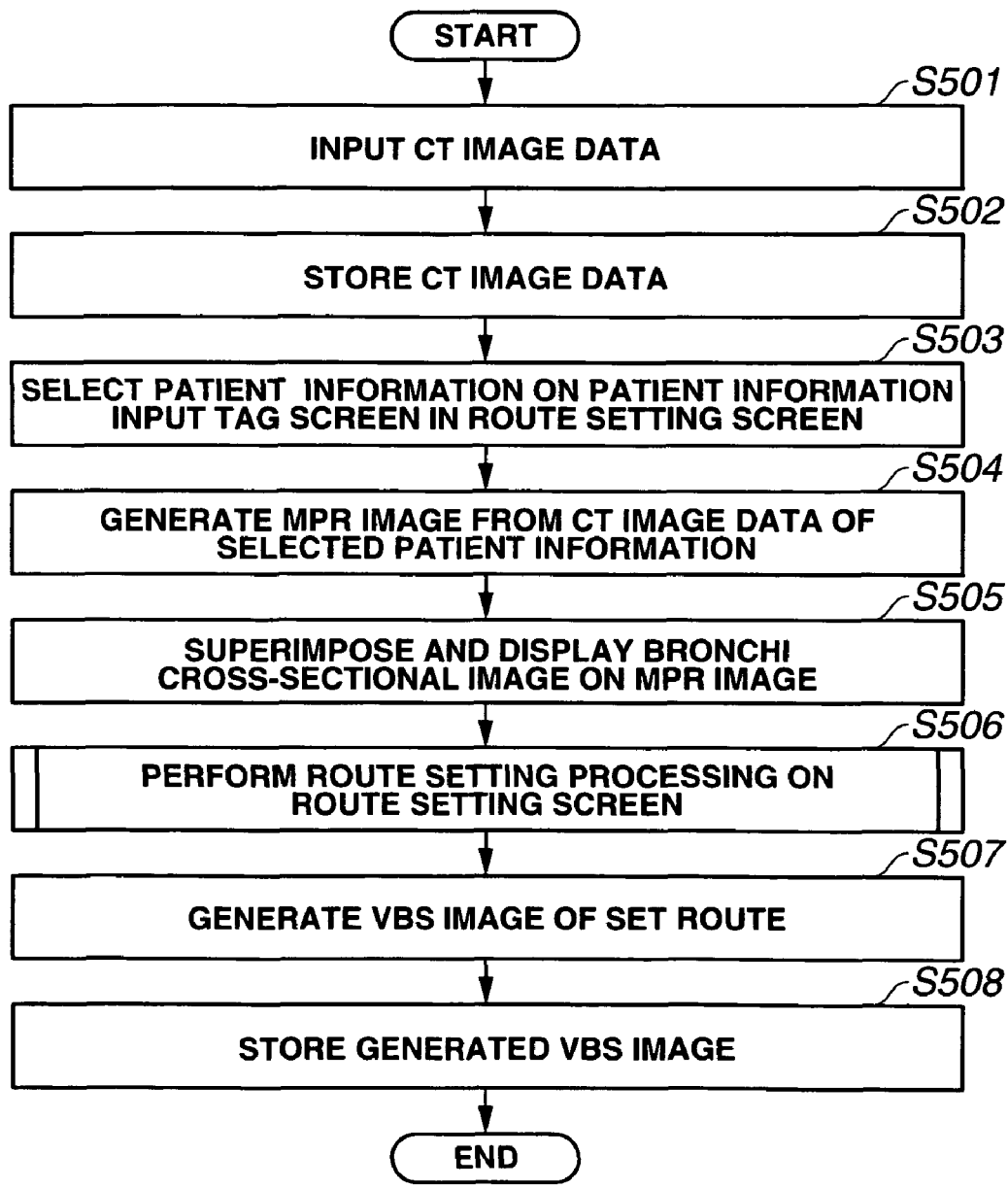
FIG. 40 is a flowchart illustrating a flow of an insertion support data generating processing performed by the insertion support apparatus of FIG. 39.

As illustrated in FIG. 40, prior to observation and treatment using the bronchoscope device 503, in the insertion support apparatus 505, the CT image data reading unit 511 reads the CT image data of the patient generated by the CT apparatus at Step S501. The thus read CT image data is stored in the CT image data storing unit 512 at Step S502.

Figure 41:
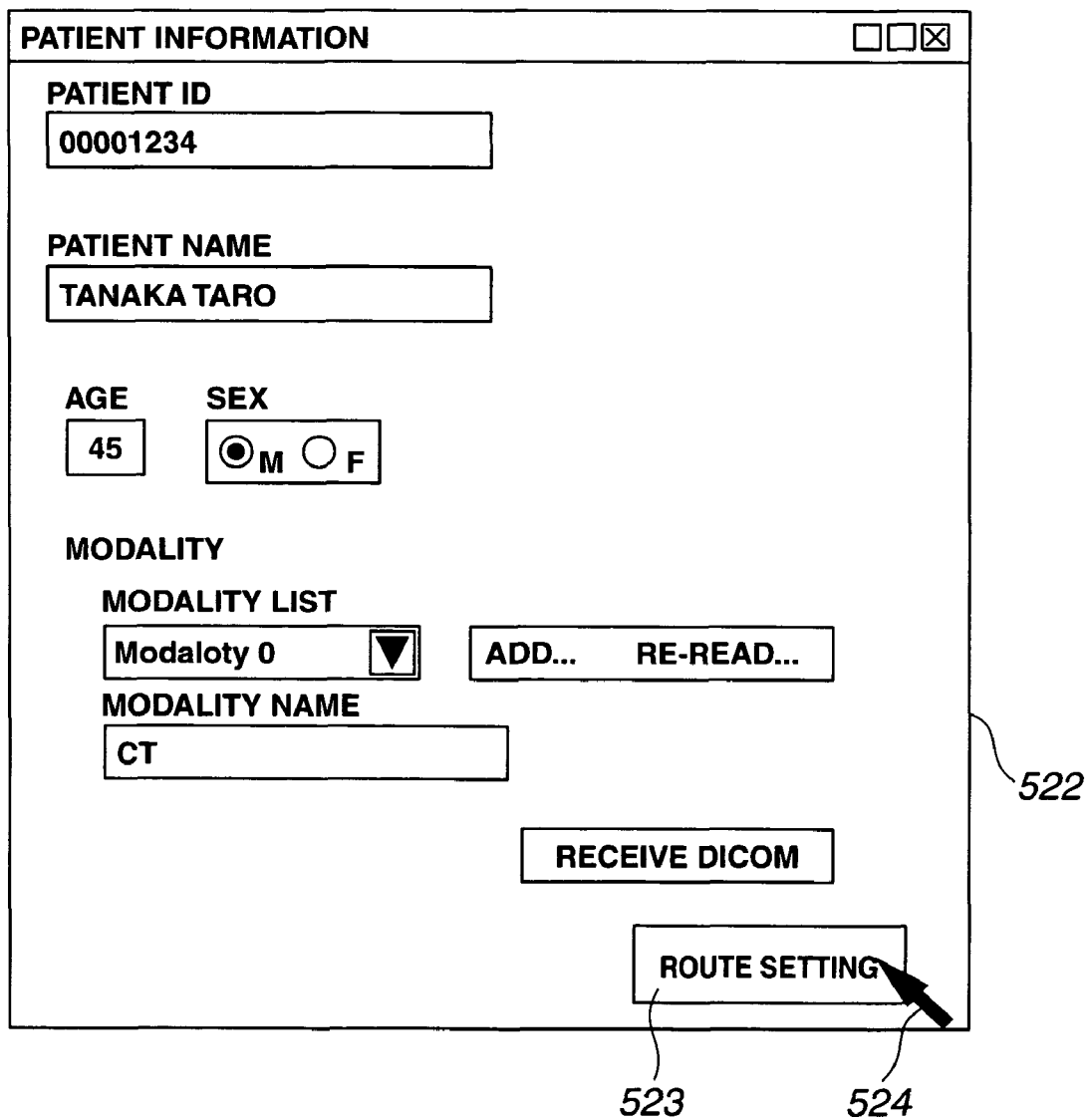
FIG. 41 is a diagram showing a patient information selection screen appearing in the processing of FIG. 40.
Figure 42:
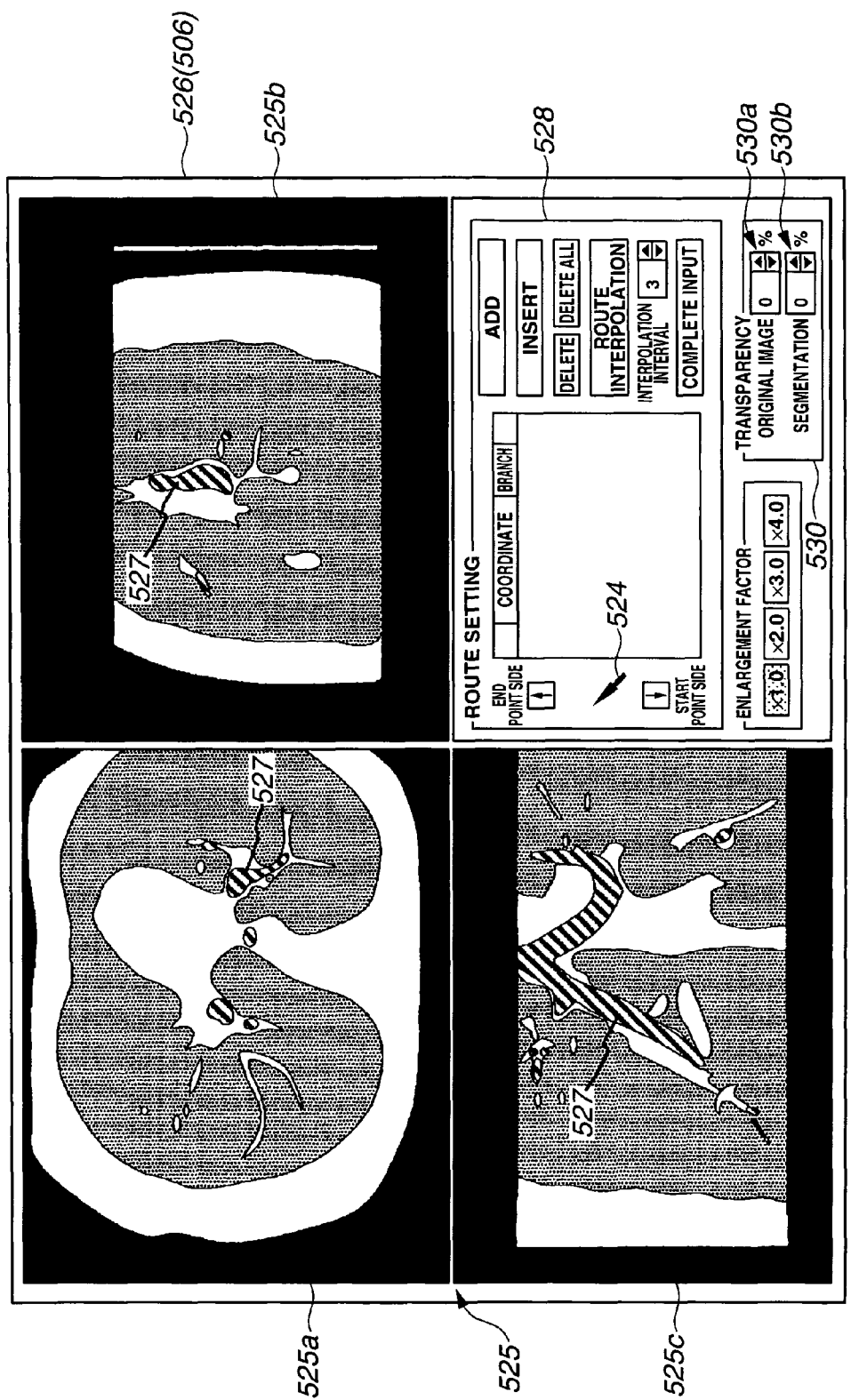
FIG. 42 is a diagram showing a route setting screen appearing in the processing of FIG. 40.

At Step S503, the route setting unit 514 displays a patient information selection screen 522 as shown in FIG. 41 on the monitor 506, and patient information is selected on the patient information selection screen 522. As a route setting button 523 on the patient information selection screen 522 is selected with a pointer 524 through the operation of the input device 519, the MPR image generating unit 513 generates MPR images including, for example, three different multi-planar images of the selected patient at Step S504. Thereby, a route setting screen 526 as shown in FIG. 42 is displayed on the monitor 506. The route setting screen 526 includes an MPR image 525 which includes an axial image 525a, a coronal image 525b, and a sagittal image 525c, and a route information screen 528 which displays route information.

The selection of the patient information by the route setting unit 514 on the patient information selection screen 522 is performed by inputting through the input device 519 a patient ID which identifies one of the patients.

Then, at Step S505, the organ extracting unit 520 extracts the bronchi that is a predetermined organ from the CT image data stored in the CT image data storing unit 512, and bronchi cross-sectional images 527 of the extracted bronchi are generated and output to the MPR image generating unit 513. Then, as illustrated in FIG. 42, the bronchi cross-sectional images 527 of the extracted bronchi are superimposed and displayed on the MPR image 325.

The axial image 525a, the coronal image 525b, and the sagittal image 525c forming the MPR image 525 are monochrome images, for example. Meanwhile, the bronchi cross-sectional images 527 superimposed on the MPR image 525 are blue images (i.e., hatched images in FIG. 42), for example. Thereby, the axial image 525a, the coronal image 525b, and the sagittal image 525c forming the MPR image 525 are displayed to be visually distinguished from the bronchi cross-sectional images 527.

Then, at Step S506, the route setting processing (later described) is performed on the route setting screen 521 to set a route for supporting insertion of the bronchoscope in the bronchi.

When the route for supporting the insertion has been set, successive VBS images of the entirety of the set route are generated in frame units by the VBS image generating unit 515 at Step S507. The generated VBS images are stored in the VBS image storing unit 516 at Step S508.

As the above processings of Steps S501 to S508 are performed, preparation for the insertion support performed by the insertion support apparatus 505 in the observation and treatment using the bronchoscope is completed.

With reference to FIGS. 42 to 46, a characteristic of a method of displaying the MPR image 525 and the bronchi cross-sectional images 527 superimposed thereon will now be described.

On the route setting screen 526 shown in FIG. 42, a transparency setting box 530 on the route information area 528 is operated with the pointer 524 by using the input device 519. Thereby, the transparency on the monitor 506 can be set for each of the MPR image 525 and the bronchi cross-sectional images 527 which are extracted luminal organ images superimposed on the MPR image 525. FIG. 42 illustrates an example display of the MPR image 525 and the bronchi cross-sectional images 527, in which the transparency is set to be 0% for both of the MPR image 525 and the bronchi cross-sectional images 527.

Specifically, the transparency setting box 530 includes an MPR image transparency adjusting button 530a and an extracted luminal organ image transparency adjusting button 530b. As the MPR image transparency adjusting button 530a and the extracted luminal organ image transparency adjusting button 330b are operated with the pointer 524 by using the input device 519, the transparency of the MPR image 525 and the bronchi cross-sectional images 527 can be increased or decreased.

Figure 43:
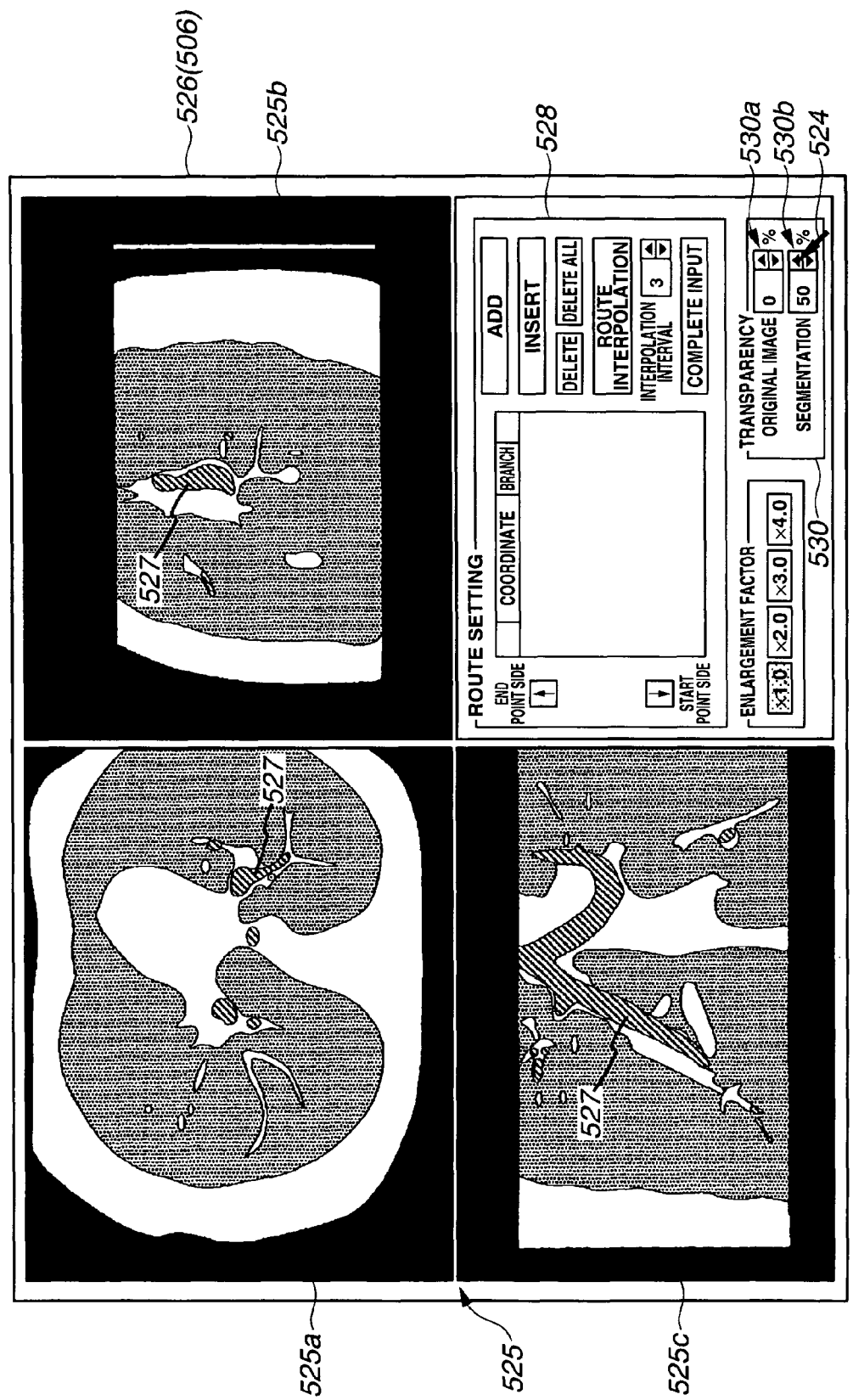
FIG. 43 is a first diagram illustrating a characteristic of a method of displaying the bronchi cross-sectional images and the MPR image of FIG. 42.
Figure 44:
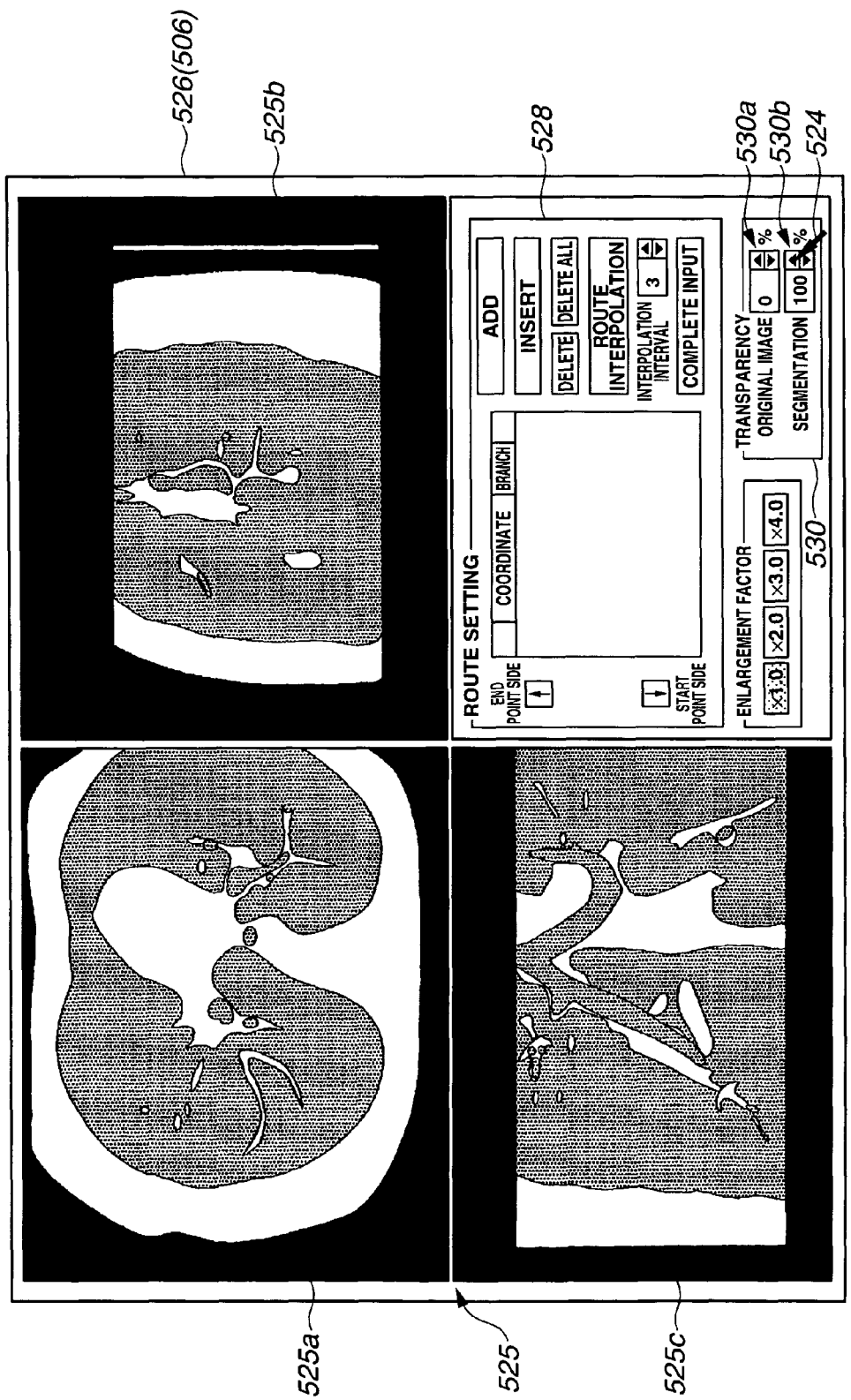
FIG. 44 is a second diagram illustrating the characteristic of the method of displaying the bronchi cross-sectional images and the MPR image of FIG. 42.

FIG. 43 illustrates an example display in which the transparency of the MPR image 525 is set to be 0% and the transparency of the bronchi cross-sectional images 527 is set to be 50%. FIG. 44 illustrates an example display in which the transparency of the MPR image 525 is set to be 0% and the transparency of the bronchi cross-sectional images 527 is set to be 100%. As illustrated in FIGS. 42 to 44, the bronchi cross-sectional images 527 can be enhanced against or assimilated into MPR image 525 by changing the transparency of the bronchi cross-sectional images 527.

Figure 45:
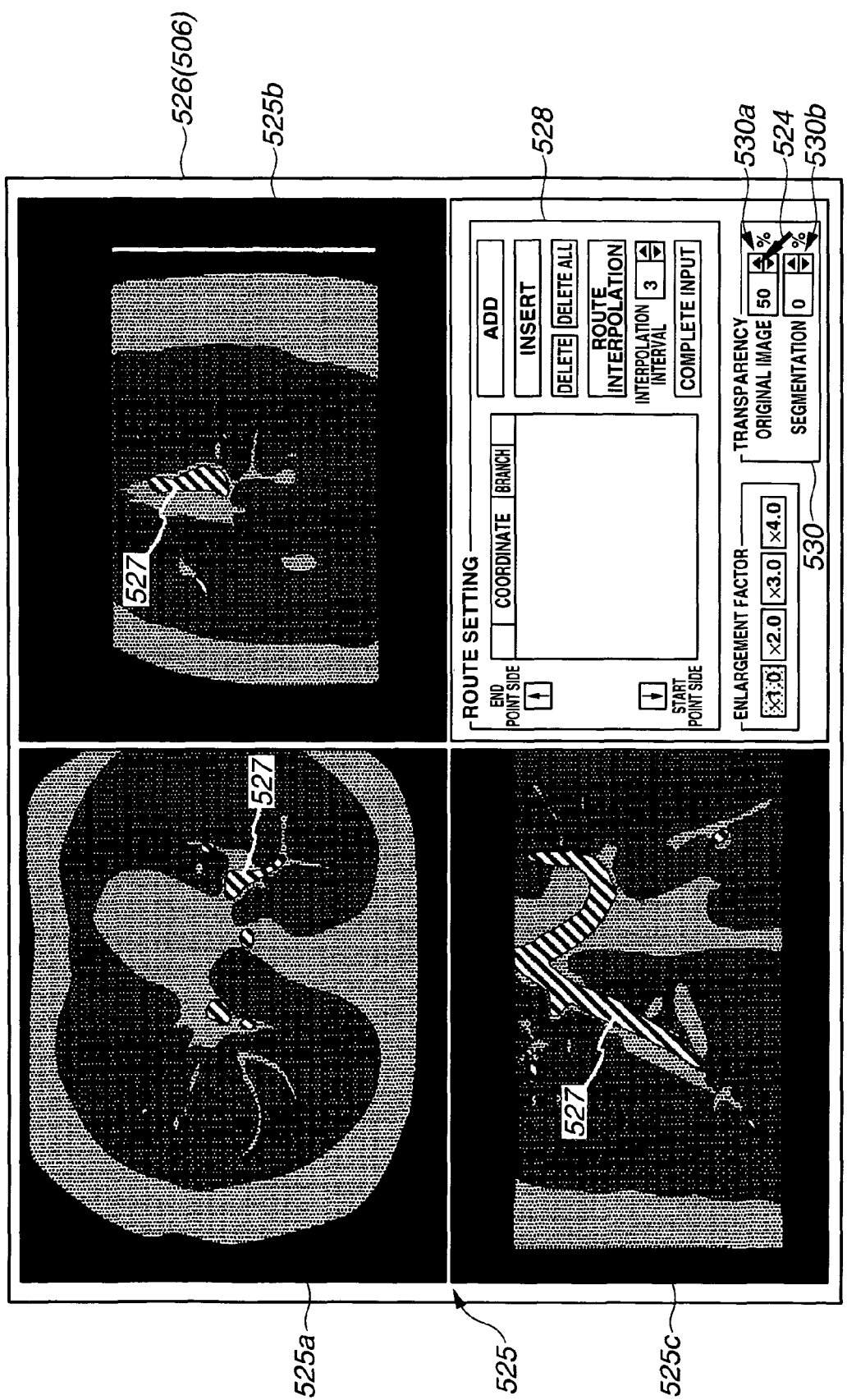
FIG. 45 is a third diagram illustrating the characteristic of the method of displaying the bronchi cross-sectional images and the MPR image of FIG. 42.
Figure 46:
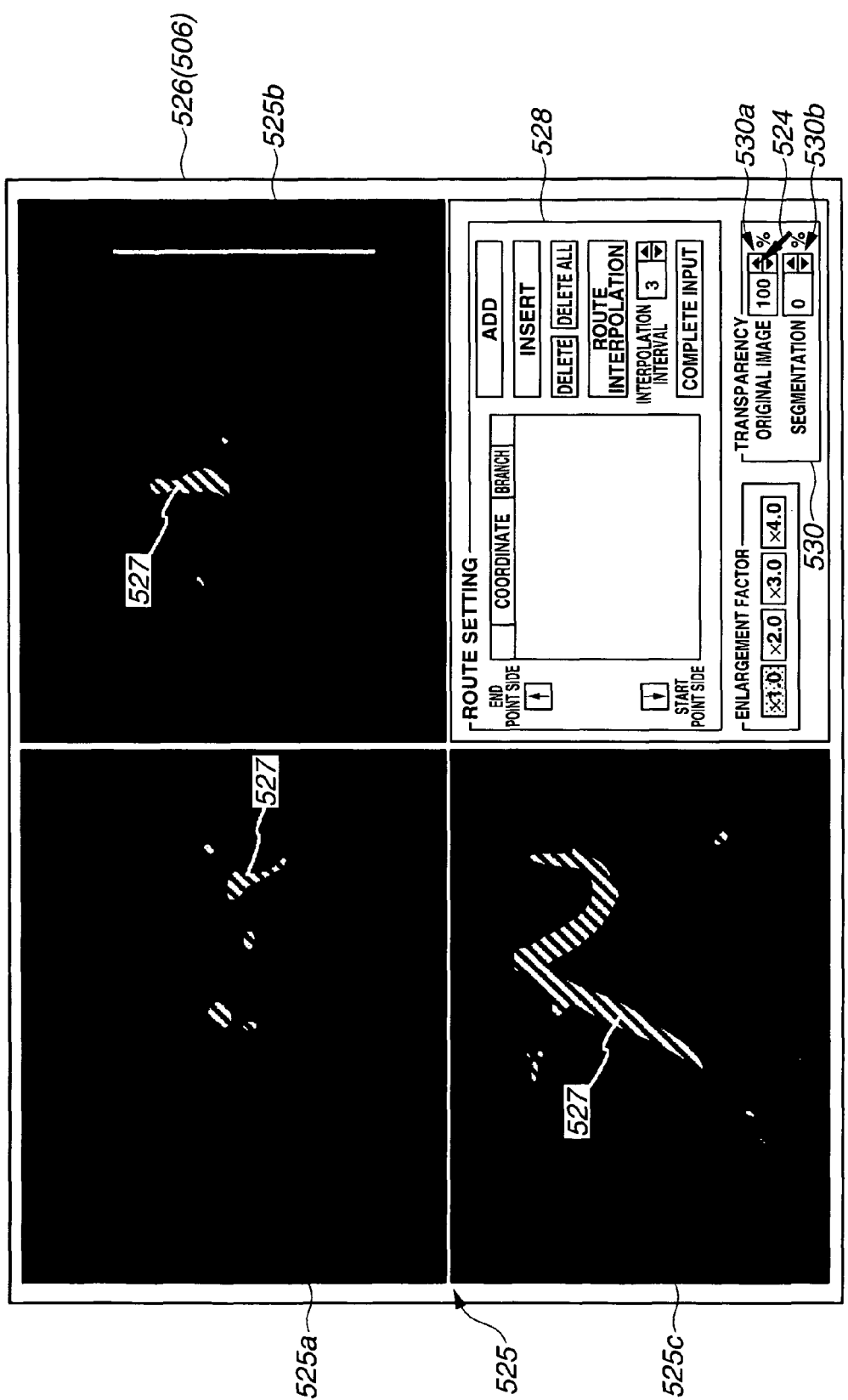
FIG. 46 is a fourth diagram illustrating the characteristic of the method of displaying the bronchi cross-sectional images and the MPR image of FIG. 42.

FIG. 45 illustrates an example display in which the transparency of the MPR image 525 is set to be 50% and the transparency of the bronchi cross-sectional images 527 is set to be 0%. FIG. 46 illustrates an example display in which the transparency of the MPR image 525 is set to be 100% and the transparency of the bronchi cross-sectional images 527 is set to be 0%. As illustrated in FIGS. 42, 45, and 46, only the bronchi cross-sectional images 527 can be displayed by changing the transparency of the MPR image 525.

As described above, as the MPR image transparency adjusting button 530a and the extracted luminal organ image transparency adjusting button 530b are operated, the transparency of the MPR image 525 and the bronchi cross-sectional images 527 can be arbitrarily increased or decreased. Further, since the bronchi cross-sectional images 527 obtained by the luminal organ extraction of the bronchi on the basis of the CT image data are superimposed and displayed on the MPR image 525 with a desired enhancement degree, a surgeon can check the location of the bronchi on the MPR image 525 while observing the ordinary MPR image 525.

The route setting processing of Step S506 performed by the route setting unit 514 will now be described with reference to FIGS. 47 to 57.

Figure 47:
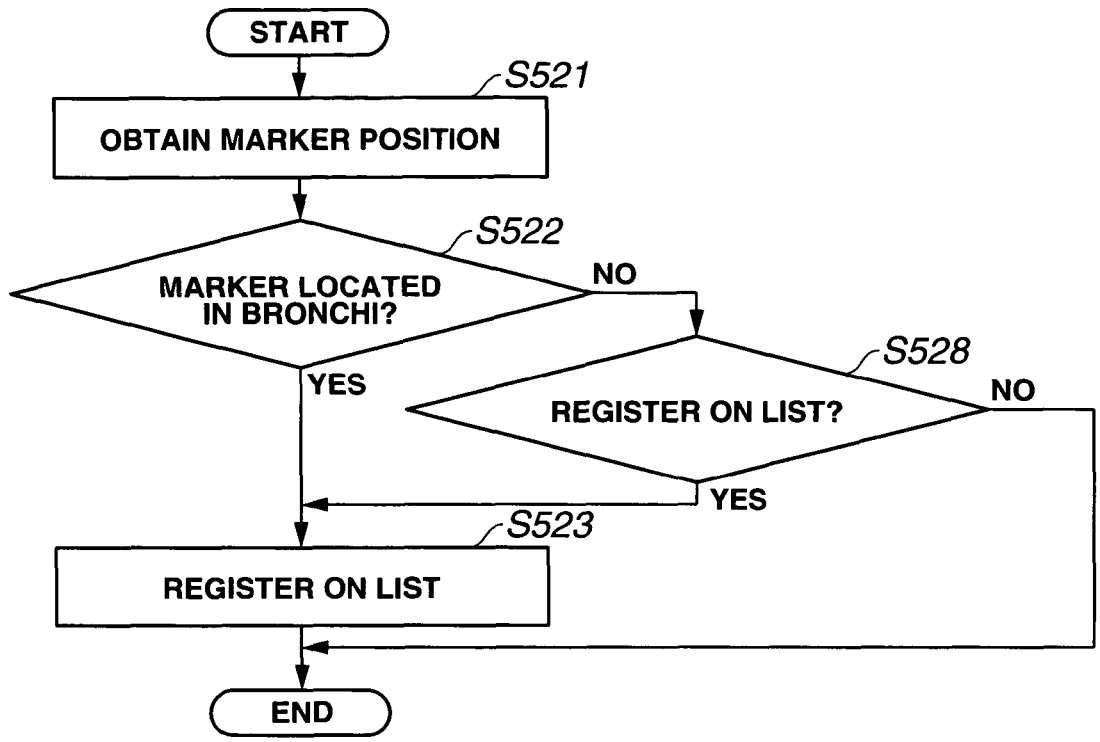
FIG. 47 is a first flowchart illustrating a flow of the route setting processing of FIG. 40.
Figure 49:
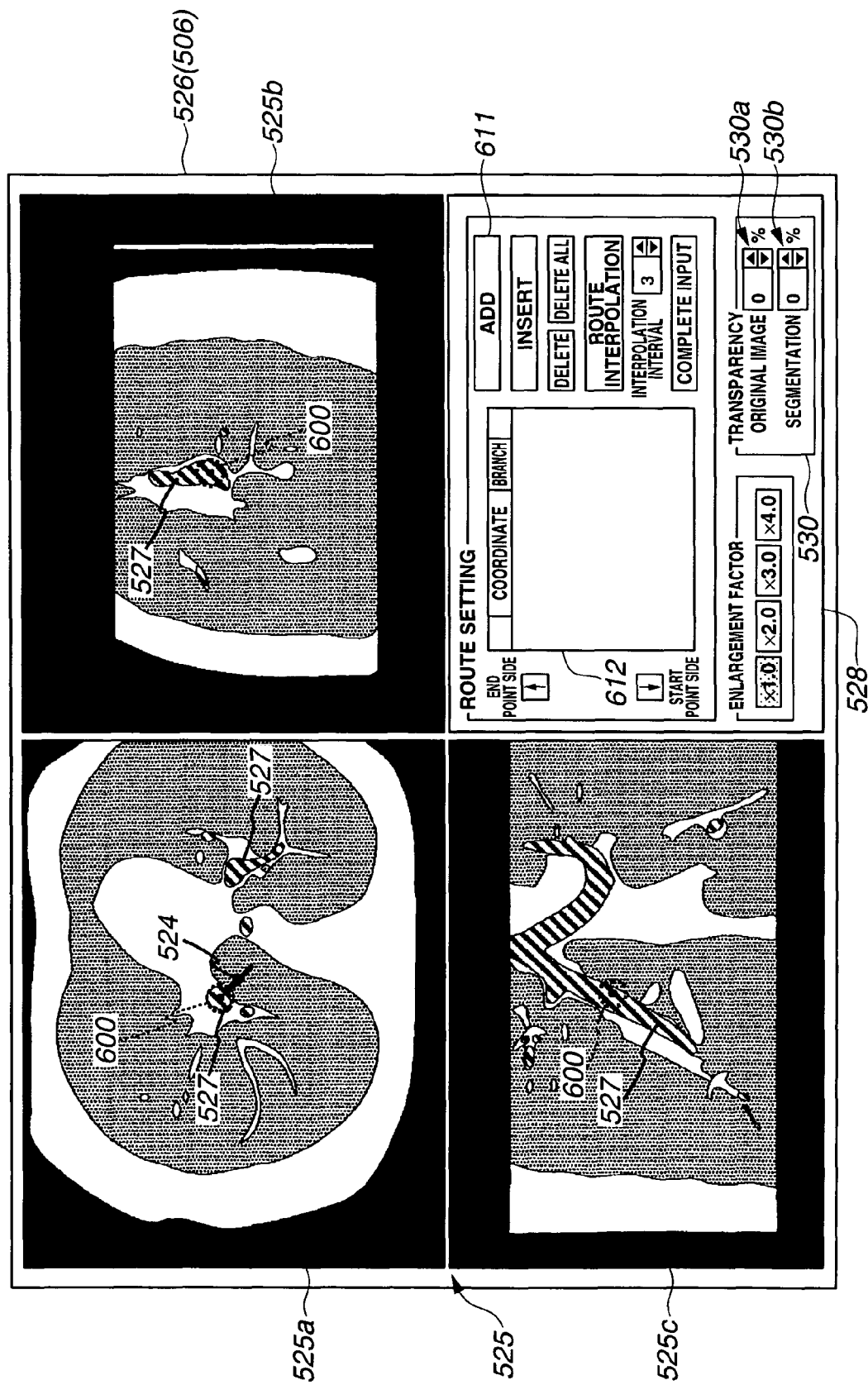
FIG. 49 is a first diagram illustrating the processings of FIGS. 47 and 48.

As illustrated in FIG. 47, a marker indicating the position of the end point of the insertion support into the bronchi is obtained on the MPR image at Step S521. Specifically, as illustrated in FIG. 49, if a position on the axial image 525a of the MPR image 525, for example, is clicked with the pointer 524, a marker 600 is displayed at the position at which the clicking has been performed. At the same time, the marker 600 is also displayed at a corresponding position in each of the coronal image 525b and the sagittal image 525c.

When an add button 611 on the route information area 528 is selected with the pointer 524, the route setting unit 514 obtains a three-dimensional coordinate of the marker 600 specified on the axial screen 525a, the coronal image 525b, and the sagittal image 525c.

Figure 50:
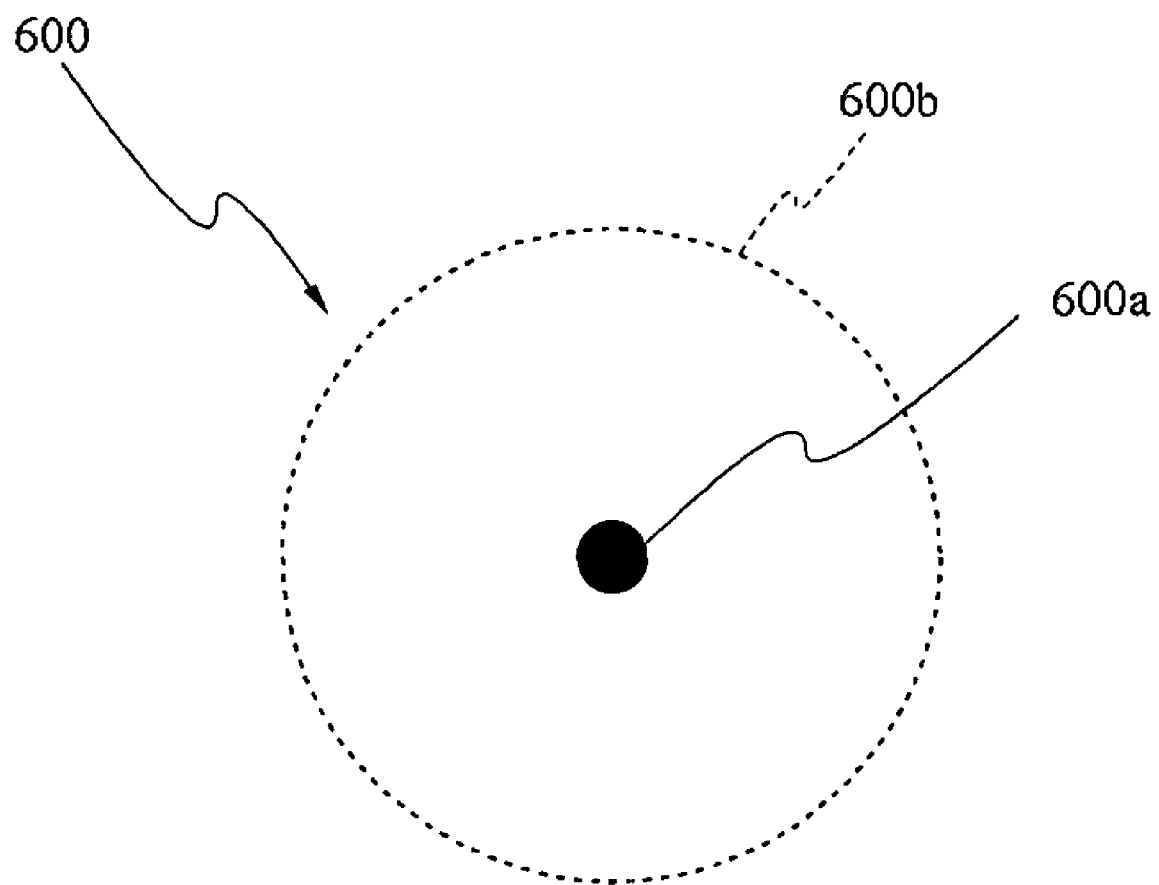
FIG. 50 is a second diagram illustrating the processings of FIGS. 47 and 48.

As illustrated in FIG. 50, the marker 600 includes a mark point 600a which indicates the point at which the clicking has been performed by the pointer 524, and a region line 600b which indicates a predetermined region including the mark point 600a such that the mark point 600a can be visually recognized on the MPR image 525. Therefore, the surgeon can easily check the position of the marker 600 by visually recognizing the region line 600b on the MPR image 525.

Figure 57:
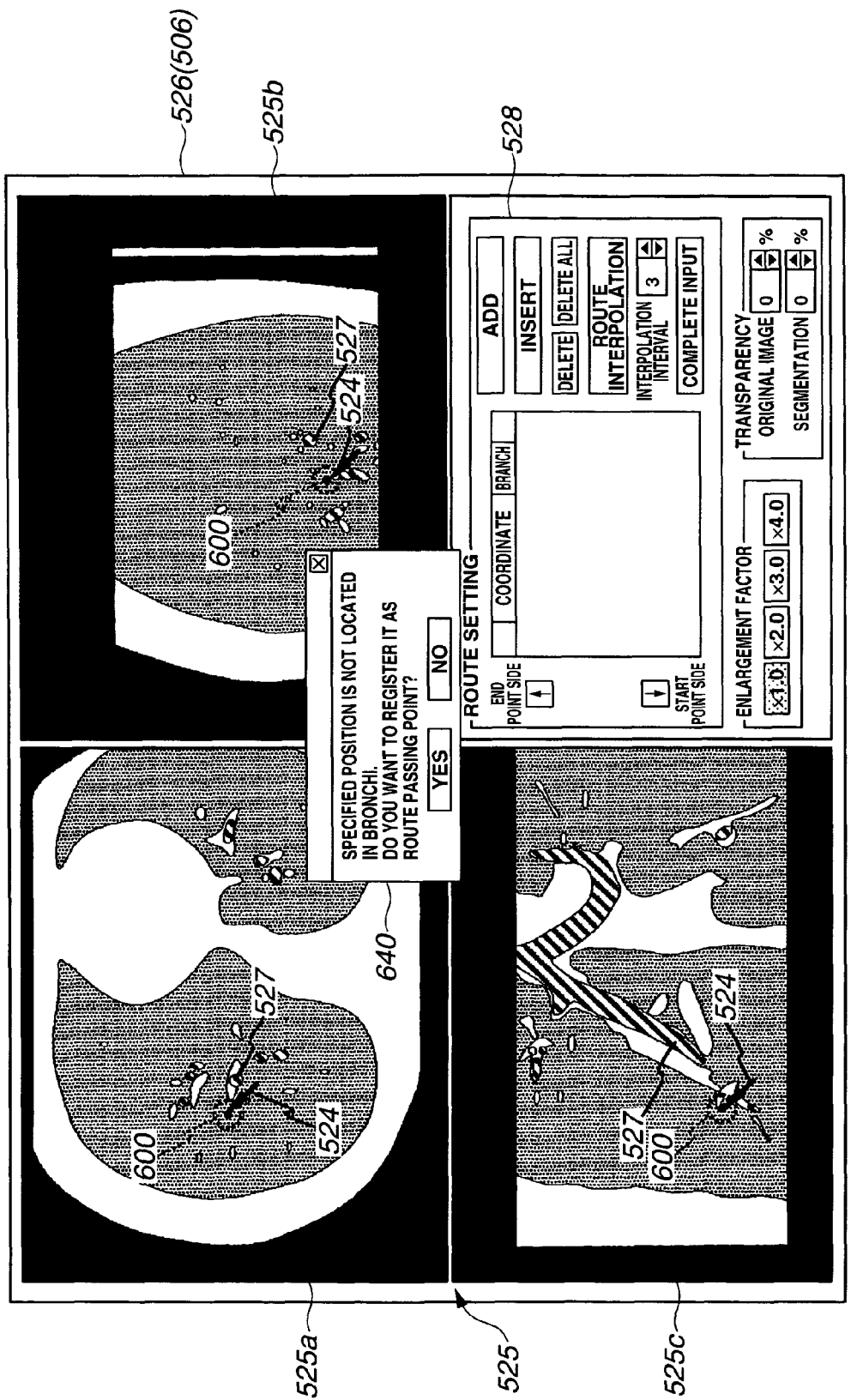
FIG. 57 is a ninth diagram illustrating the processings of FIGS. 47 and 48.

Then, at Step S522, it is determined whether the marker 600 is located within the bronchi. If it is determined that the marker 600 is located within the bronchi, a mark point is registered on a passing point list at Step S523. If it is determined that the marker 100 is not located within the bronchi, a confirmation window 640 as shown in FIG. 57 is displayed at Step S528. If the surgeon has specified the mark point outside the bronchi and selects "YES," the mark point is registered on the passing point list. The three-dimensional coordinate of the marker 600 registered on the passing point list is displayed with a number in a registered information area 612 (refer to FIGS. 49 and 52) on the route information area 528.

Figure 51:
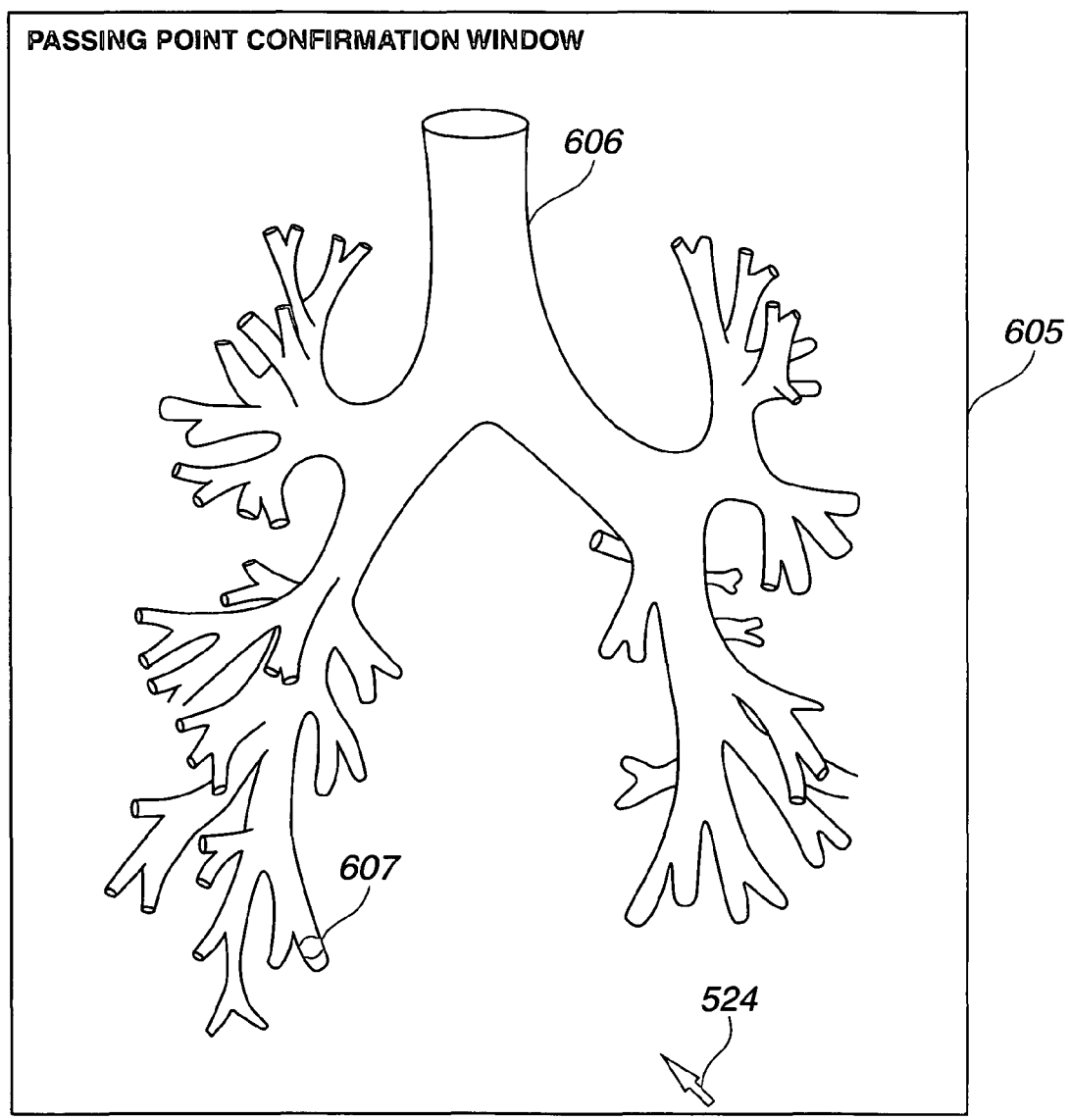
FIG. 51 is a third diagram illustrating the processings of FIGS. 47 and 48.

Further, a passing point confirmation window 605 as shown in FIG. 51 may be displayed. The passing point confirmation window 605 is a window used for confirming the marker 600 on a bronchi image 606 which is displayed three-dimensionally. With the passing point confirmation window 605, the surgeon determines whether the marker 600 has been placed at a predetermined position within the bronchi.

Then, a process of registering the marker 600 on the passing point list is repeated for each of passing points leading to a desired position.

Figure 52:
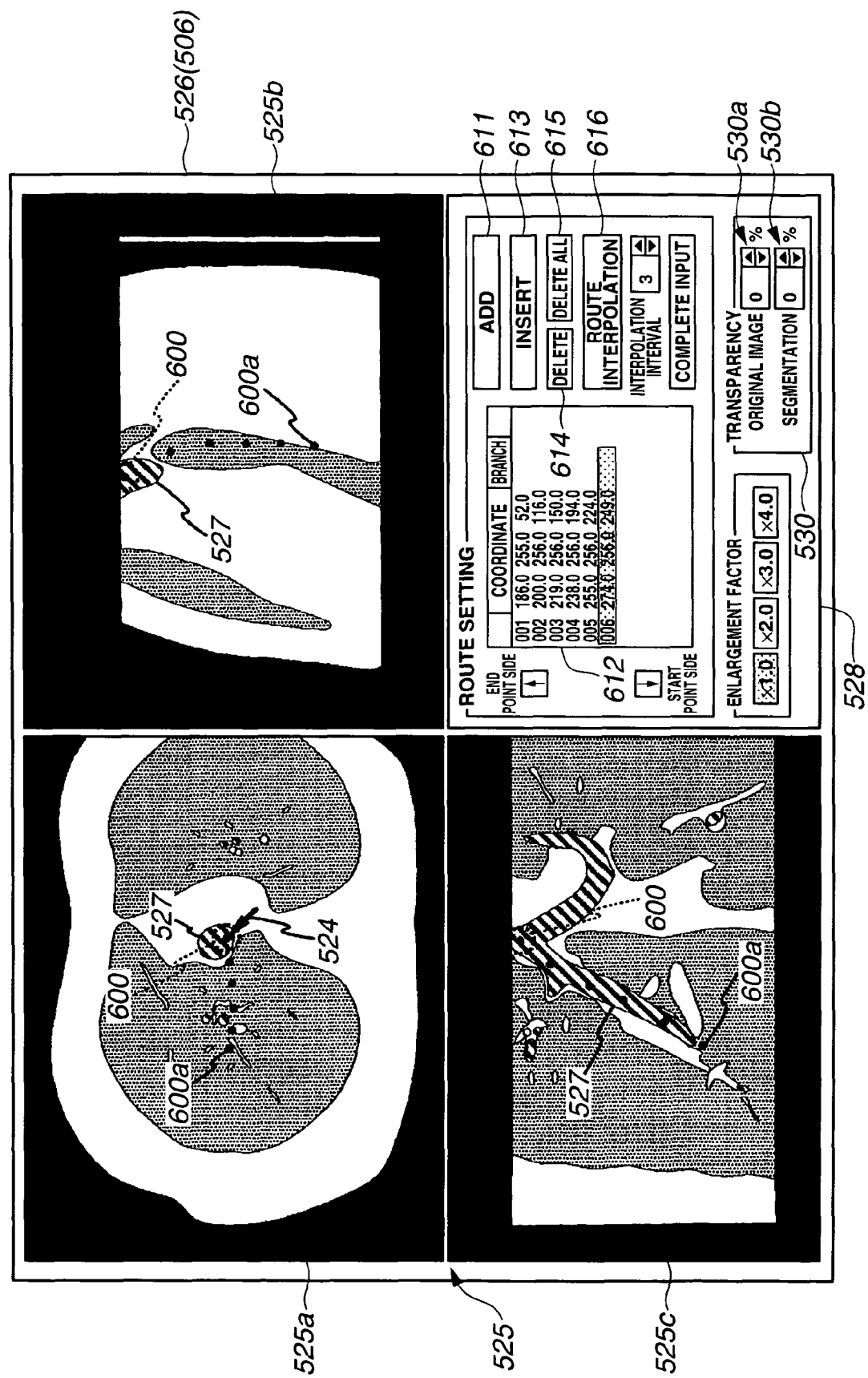
FIG. 52 is a fourth diagram illustrating the processings of FIGS. 47 and 48.
Figure 53:
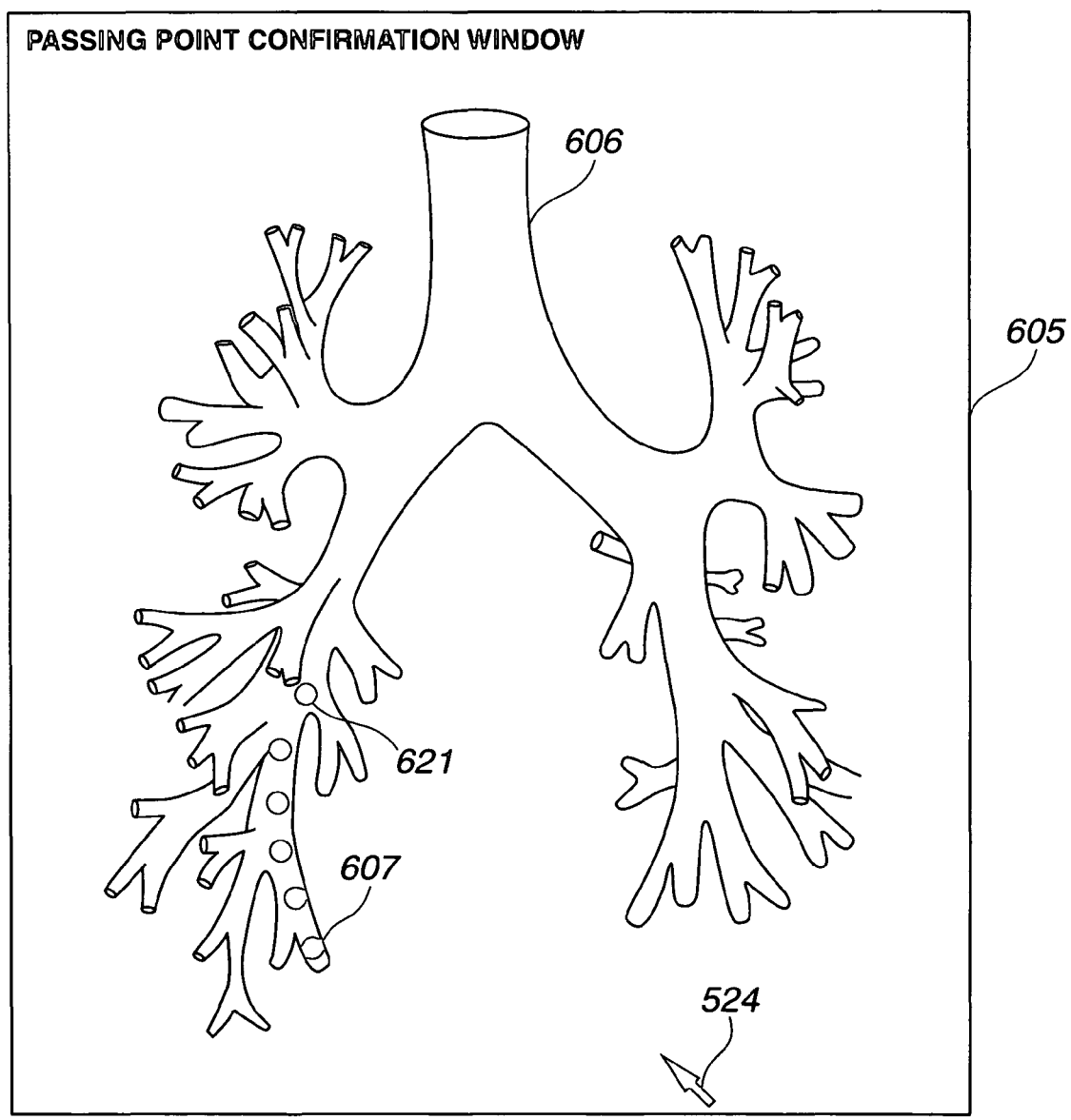
FIG. 53 is a fifth diagram illustrating the processings of FIGS. 47 and 48.

FIG. 52 illustrates a state in which a sixth passing point is newly specified by the marker 600 after five passing points have been registered. As illustrated on the MPR image 525 shown in FIG. 52, the already registered five passing points 600a are displayed as green points, for example. Further, in the passing point confirmation window 605, the already registered five passing points 600a are displayed as green points, while the sixth passing point 621 is displayed as a red point, for example.

Figure 54:
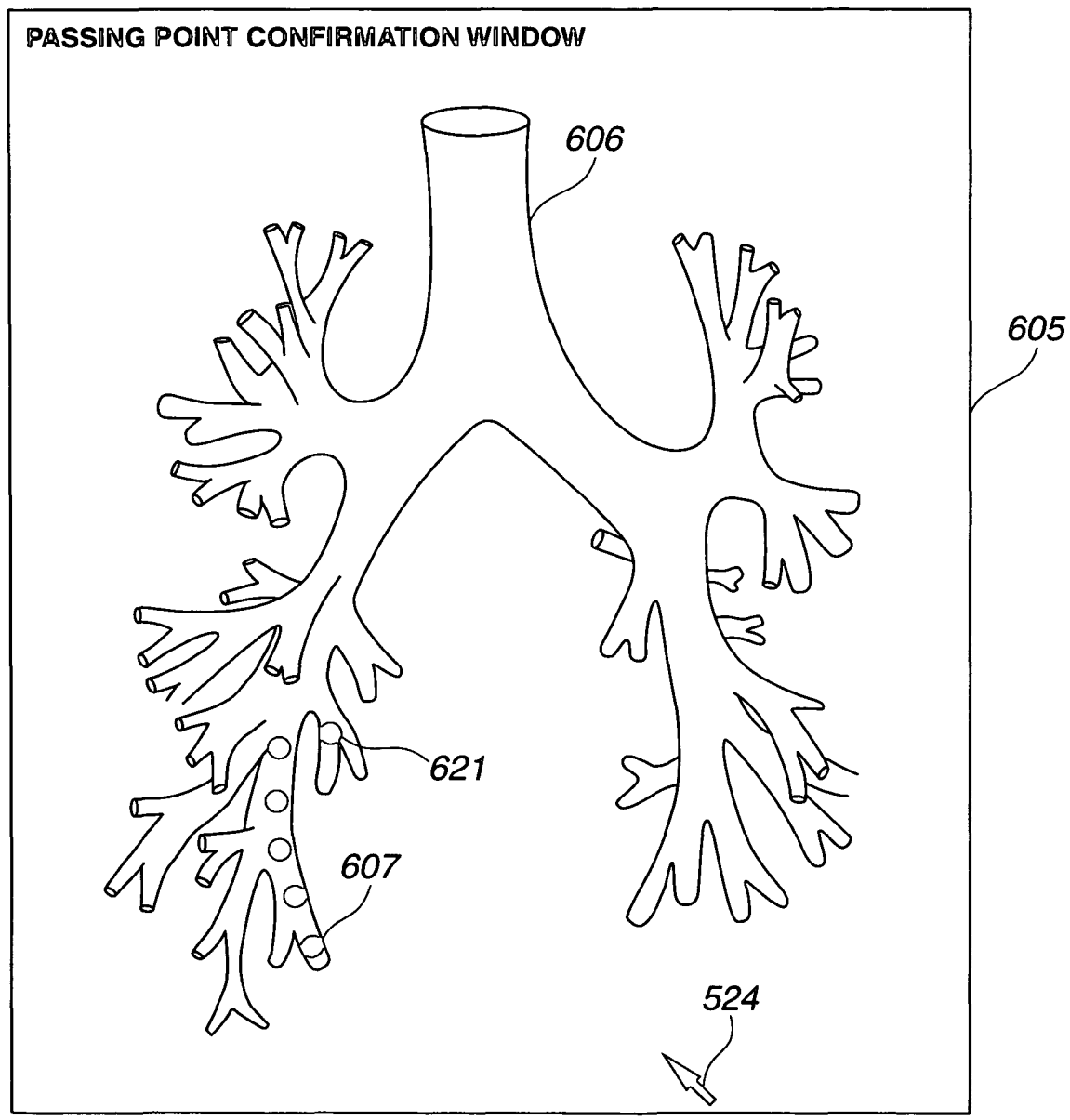
FIG. 54 is a sixth diagram illustrating the processings of FIGS. 47 and 48.

For example, in specifying the sixth passing point with the marker 600 on the MPR image 525 shown in FIG. 52, if it is determined with the passing point confirmation window 605 shown in FIG. 54 that a current passing point 621 has been marked at a position within the bronchi not suitable for the insertion support with respect to the previously specified passing point on the bronchi image 606, the specification of the marker 600 can be cancelled by selecting a delete button 614 on the route information area 528 shown in FIG. 52 with the pointer 524. If a delete-all button 615 is selected, all of the passing points including the current passing point 621 are deleted.

Figure 55:
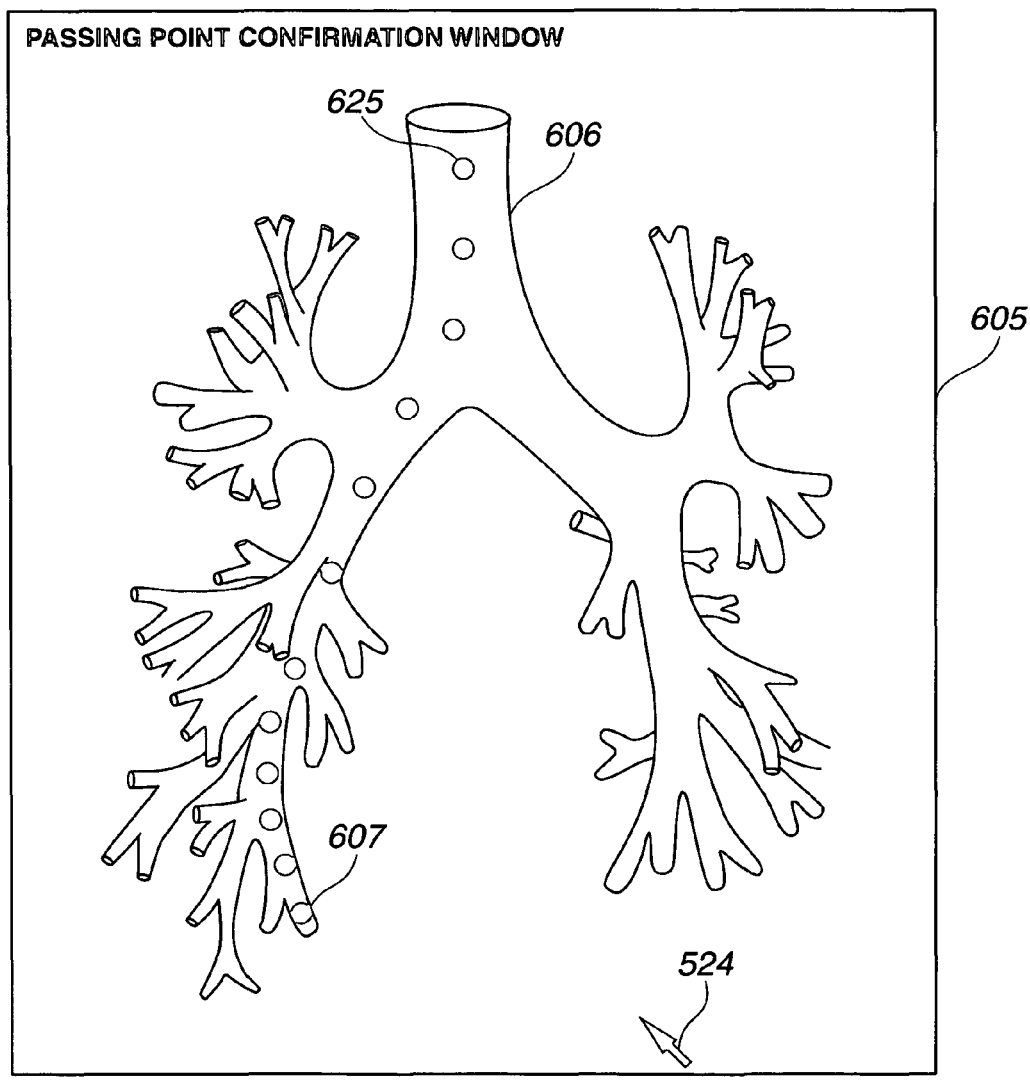
FIG. 55 is a seventh diagram illustrating the processings of FIGS. 47 and 48.
Figure 56:
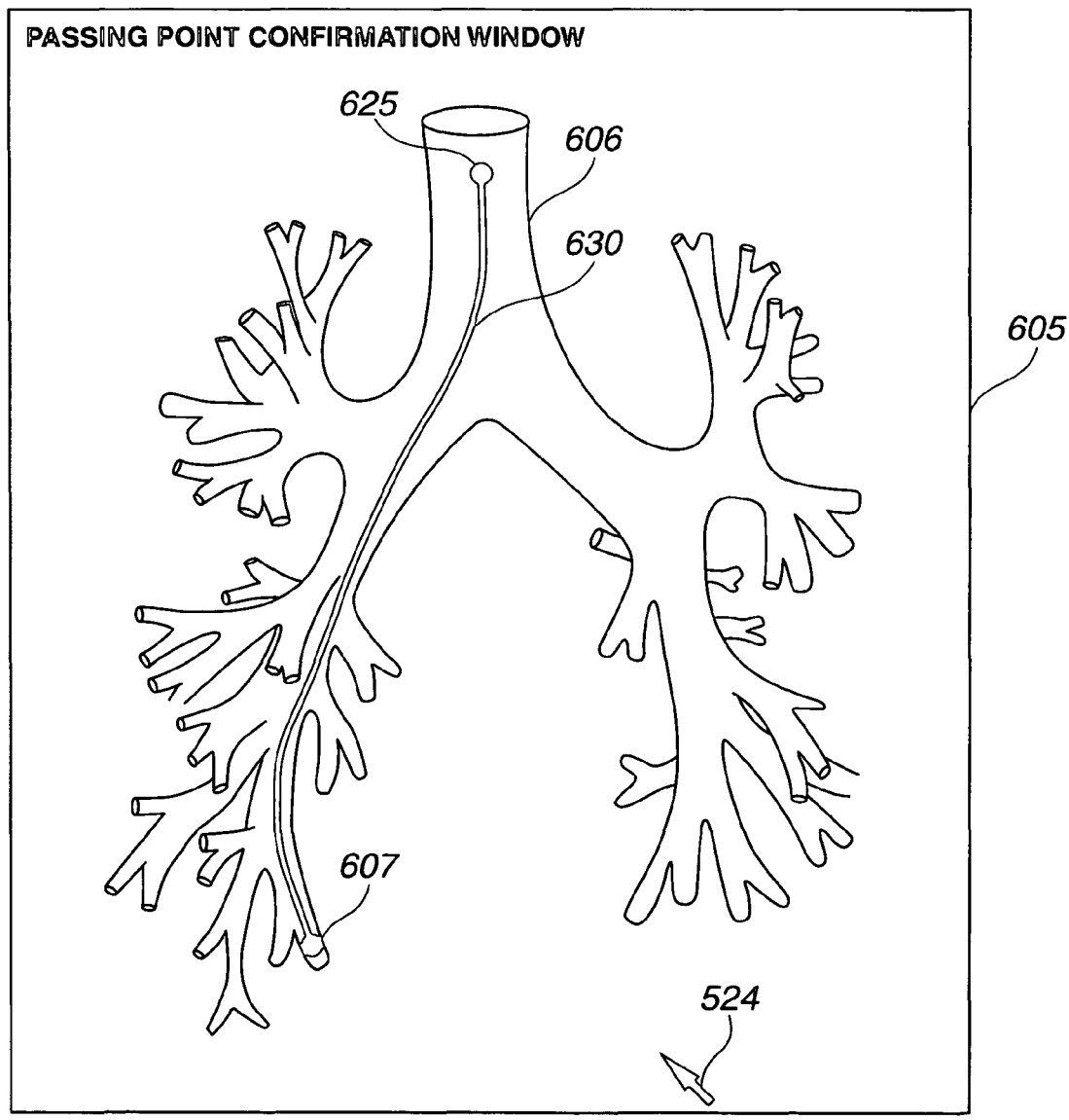
FIG. 56 is an eighth diagram illustrating the processings of FIGS. 47 and 48.

As illustrated in the passing point confirmation window 605 of FIG. 55, after the desired passing points connecting the end point 607 and the desired start point 625 at which the insertion support is started have been thus registered on the passing point list, the surgeon determines whether interpolation of the passing points needs to be performed.

Figure 48:
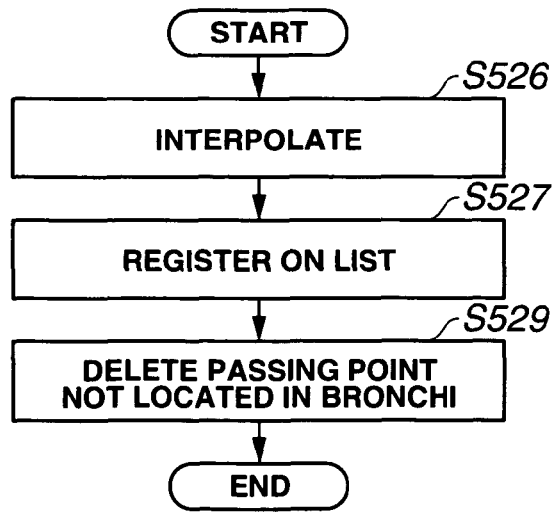
FIG. 48 is a second flowchart illustrating the flow of the route setting processing of FIG. 40.

If a route interpolation button 616 is selected, a predetermined interpolation processing (e.g., linear interpolation between the passing points) is performed at Step S526 of FIG. 48.

This interpolation processing is performed by interpolating a plurality of virtual points at predetermined intervals between the passing points in the bronchi. The interpolation interval of the virtual points can be arbitrarily set with an interpolation interval box 617 on the route information area 528.

Then, a route 630 formed by the passing points including the virtual points is registered on the passing point list at Step S527.

However, the passing points registered at Step S527 are not necessarily located within the bronchi. If the interpolation processing has been performed outside the bronchi, the passing point not located within the bronchi is deleted from the passing point list at Step S529 after the processing of Step S527 has been performed. Then, the interpolation processing is completed, and the route 630 is displayed on the passing point confirmation window 605 shown in FIG. 56.

After the route 630 has been thus set by the route setting unit 514, the flow moves to the processing of Step S507 of FIG. 40. As described above, the VBS image generating unit 515 generates the successive VBS images in frame units along the set route 630 at Step S507, and the thus generated VBS images are stored in the VBS image storing unit 516 at Step S508.

Description will now be made of an insertion support screen used in the insertion support performed, during the observation and the treatment, by the insertion support apparatus 505 and the bronchoscope device 503 for which the route has been set as described above. To simplify explanation, the following description will be made of a case in which the route has ten branch points, as one example.

When the bronchoscopic examination is started under the insertion support by the insertion support apparatus 505, an insertion support screen 651 as shown in FIG. 58 is displayed on the monitor 506.

The insertion support screen 651 includes an endoscope live image display area 652 for displaying a live image sent by the bronchoscope device 503, a VBS image display area 653 for displaying a VBS image 653a, and a branch thumbnail VBS image area 654 for displaying branch thumbnail VBS images 654(a) to 654(j) which are reduced size images of the VBS image 653a at all of the branch points along the route. The VBS image 653a of the first branch point of the route is displayed in the VBS image display area 653, and the branch thumbnail VBS images 654(a) to 654(j) of all of the branch points are displayed in the branch thumbnail VBS image area 654.

A navigation maker 655 is displayed on the VBS image 653a such that the navigation maker 655 is superimposed on a route hole leading into the route. Further, one of the branch thumbnail VBS images similar to the VBS image 653a displayed in the VBS image display area 653 is framed in color or by a bold line to be distinguished from the other branch thumbnail VBS images. Accordingly, the surgeon can easily recognize which one of the branch images corresponds to the VBS image displayed in the VBS image display area 653. In an initial stage, the branch thumbnail VBS image 654(a) is framed in color or by a bold line.

As described above, in the present embodiment, the route is set by specifying the passing points with the desired intervals for connecting the end point and the start point in the bronchi and by performing the interpolation processing for a specified segment of between the end point and one of the passing points, between the passing points, and between another one of the passing points and the start point. Accordingly, an optimal route for the insertion of the endoscope (i.e., insertion support route) connecting the start point and the end point along a duct in the bronchi can be obtained by calculation.

The present invention is not limited to the embodiments described above but can be modified or altered in various ways within a scope not changing the gist of the present invention.

What is claimed is:

1. A multi-planar reformatted image generating apparatus comprising:
    a three-dimensional image data storing unit for obtaining three-dimensional image data of a subject obtained by reformatting, on the basis of image data of a plurality of cross-sectional images in a three-dimensional region of the subject, the plurality of cross-sectional image data, and storing the obtained three-dimensional image data;
    a multi-planar reformatted image generating unit for generating at least one multi-planar reformatted image which is a two-dimensional image of the subject on the basis of image data of a three-dimensional region in the subject stored in the three-dimensional image data storing unit;
    a luminal organ information extracting unit for extracting information concerning the shape of the three-dimensional region of a predetermined luminal organ, on the basis of the image data of the three-dimensional region in the subject stored in the three-dimensional image data storing unit;
    an extracted luminal organ image superimposing unit for superimposing an extracted luminal organ image, in which a result of the luminal organ extraction obtained by the luminal organ information extracting unit is reflected, on a predetermined cross-sectional image in the at least one multi-planar reformatted image to correspond to the predetermined cross-sectional image in the multi-planar reformatted image; and
    a route setting unit for setting a route for inserting an endoscope in a duct of the luminal organ, on a superimposed two-dimensional image wherein the extracted luminal organ image is superimposed on the multi-planar reformatted image.

2. The multi-planar reformatted image generating apparatus according to claim 1, comprising:
    an extracted luminal organ image transparency changing unit for changing the transparency of the extracted luminal organ image superimposed on the multi-planar reformatted image.

3. The multi-planar reformatted image generating apparatus according to claim 2, comprising:
    a multi-planar reformatted image transparency changing unit for changing the transparency of the multi-planar reformatted image on which the extracted luminal organ image is superimposed.

4. The multi-planar reformatted image generating apparatus according to claim 1, comprising:
    a multi-planar reformatted image transparency changing unit for changing the transparency of the multi-planar reformatted image on which the extracted luminal organ image is superimposed.

5. The multi-planar reformatted image generating apparatus according to claim 1, further comprising:
    an insertion support system comprising:
    an input device for specifying, on the multi-planar reformatted image, an end point in a luminal organ in the subject and repeating to specify desired passing points up to a predetermined position; and
    the route setting unit further for repeating to obtain a coordinate of the endpoint and coordinates of the desired passing points in the three-dimensional region, determining whether or not the end point and the desired passing points are in the luminal duct, registering the desired passing points between the end point and a desired start point where insertion support is to be started in the duct, performing an interpolation processing by interpolating a plurality of virtual points between the desired passing points at predetermined intervals, and deleting passing points not existing in the duct.

6. The insertion support system according to claim 5, comprising:
    a luminal organ extracting unit for extracting segmentation, which is data of the shape of the three-dimensional region of the luminal organ, on the basis of the image data of the three-dimensional region in the subject; and
    a coordinate position identifying unit for determining whether either one of the coordinate of the three-dimensional region of the end point specified by the end point coordinate specifying unit and the coordinate of the three-dimensional region of the passing point specified by the passing point coordinate specifying unit is located within the three-dimensional region occupied by the segmentation extracted by the luminal organ extracting unit.

7. The insertion support system according to claim 6, further comprising:
    a luminal organ image generating unit for generating a three-dimensional image of the luminal organ on the basis of the segmentation extracted by the luminal organ extracting unit; and
    a plotting unit for plotting the end point and the passing point on the three-dimensional image of the luminal organ generated by the luminal organ image generating unit.

8. The insertion support system according to claim 7, comprising:
    an interpolation performing unit for performing interpolation between the end point and one of the passing points, between the passing points, and between another one of the passing points and the start point; and
    a route setting unit for setting a result of the processing performed by the interpolation performing unit as a route connecting the start point and the end point.

9. The insertion support system according to claim 8, wherein a marker indicating either one of the end point specified by the end point coordinate specifying unit and the passing point specified by the passing point coordinate specifying unit is superimposed on the multi-planar reformatted image.

10. The insertion support system according to claim 9, wherein the marker includes:
    a position mark portion for specifying the position of either one of the end point and the passing point; and
    a region mark portion for indicating a predetermined region including the position of either one of the end point and the passing point.

11. The insertion support system according to claim 7, wherein a marker indicating either one of the end point specified by the end point coordinate specifying unit and the passing point specified by the passing point coordinate specifying unit is superimposed on the multi-planar reformatted image.

12. The insertion support system according to claim 11, wherein the marker includes:
a position mark portion for specifying the position of either one of the end point and the passing point; and
a region mark portion for indicating a predetermined region including the position of either one of the end point and the passing point.

13. The insertion support system according to claim 6, comprising:
an interpolation performing unit for performing interpolation between the end point and one of the passing points, between the passing points, and between another one of the passing points and the start point; and
a route setting unit for setting a result of the processing performed by the interpolation performing unit as a route connecting the start point and the end point.

14. The insertion support system according to claim 13, wherein a marker indicating either one of the end point specified by the end point coordinate specifying unit and the passing point specified by the passing point coordinate specifying unit is superimposed on the multi-planar reformatted image.

15. The insertion support system according to claim 14, wherein the marker includes:
a position mark portion for specifying the position of either one of the end point and the passing point; and
a region mark portion for indicating a predetermined region including the position of either one of the end point and the passing point.

16. The insertion support system according to claim 6, wherein a marker indicating either one of the end point specified by the end point coordinate specifying unit and the passing point specified by the passing point coordinate specifying unit is superimposed on the multi-planar reformatted image.

17. The insertion support system according to claim 16, wherein the marker includes:
a position mark portion for specifying the position of either one of the end point and the passing point; and
a region mark portion for indicating a predetermined region including the position of either one of the end point and the passing point.

18. The insertion support system according to claim 6, wherein the multi-planar reformatted image generating unit is controlled to superimpose a segmentation image, in which the segmentation is reflected, on the multi-planar reformatted image.

19. The insertion support system according to claim 5, comprising:
an interpolation performing unit for performing interpolation between the end point and one of the passing points, between the passing points, and between another one of the passing points and the start point; and
a route setting unit for setting a result of the processing performed by the interpolation performing unit as a route connecting the start point and the end point.

20. The insertion support system according to claim 19, wherein a marker indicating either one of the end point specified by the end point coordinate specifying unit and the passing point specified by the passing point coordinate specifying unit is superimposed on the multi-planar reformatted image.

21. The insertion support system according to claim 20, wherein the marker includes:
a position mark portion for specifying the position of either one of the end point and the passing point; and
a region mark portion for indicating a predetermined region including the position of either one of the end point and the passing point.

22. The insertion support system according to claim 5, wherein a marker indicating either one of the end point specified by the end point coordinate specifying unit and the passing point specified by the passing point coordinate specifying unit is superimposed on the multi-planar reformatted image.

23. The insertion support system according to claim 22, wherein the marker includes:
a position mark portion for specifying the position of either one of the end point and the passing point; and
a region mark portion for indicating a predetermined region including the position of either one of the end point and the passing point.

* * * * *